United States Patent [19]

Bourgery et al.

[11] 4,178,442

[45] Dec. 11, 1979

[54] NOVEL CINNAMOYLES PIPERAZINES AND HOMOPIPERAZINES, THE METHOD OF PREPARING THEM AND THEIR APPLICATION IN THERAPEUTICS

[75] Inventors: Guy R. Bourgery, Colombes; Alain P. Lacour, La Varenne; Gerard H. Moinet, Orsay; Bernard M. Pourrias, Meudon la Foret; Anne-Marie P. Ruch, Paris, all of France

[73] Assignee: Delalande S. A., Courbevoie, France

[21] Appl. No.: 894,965

[22] Filed: Apr. 10, 1978

[30] Foreign Application Priority Data

Apr. 19, 1977 [FR] France .................................. 77 11707

[51] Int. Cl.$^2$ .................. C07D 241/04; C07D 243/08
[52] U.S. Cl. .................................. 542/440; 424/244; 424/250; 542/429; 542/436; 542/439; 542/431; 542/432; 544/377; 544/391
[58] Field of Search ................ 544/391, 377; 424/250; 542/440, 429, 436, 439, 431, 432

[56] References Cited

U.S. PATENT DOCUMENTS

| | | | |
|---|---|---|---|
| 3,268,407 | 8/1966 | Hofmann | 542/440 |
| 3,590,034 | 6/1971 | Fauran et al | 542/440 |
| 3,753,984 | 8/1973 | Fauran et al. | 542/440 |
| 3,940,386 | 2/1976 | Szabo et al. | 424/250 |
| 3,957,789 | 5/1976 | Jacquier | 424/250 |
| 3,997,666 | 12/1976 | Witte et al. | 424/250 |
| 4,016,154 | 4/1977 | Turin et al. | 542/440 |
| 4,029,650 | 6/1977 | Raynaud et al. | 542/440 |
| 4,038,279 | 7/1977 | Renth et al. | 424/250 |

OTHER PUBLICATIONS

Fauran et. al., Chim. Therapeutica 4 (#4) 1969 pp. 290–292.

*Primary Examiner*—Arthur P. Demers
*Attorney, Agent, or Firm*—Blanchard, Flynn, Thiel, Boutell & Tanis

[57] ABSTRACT

Cinnamoyl piperazine and homopiperazine derivatives which possess antiangorous activity and activities on the peripheral and cerebral circulation.

40 Claims, No Drawings

NOVEL CINNAMOYLES PIPERAZINES AND HOMOPIPERAZINES, THE METHOD OF PREPARING THEM AND THEIR APPLICATION IN THERAPEUTICS

The present invention relates to certain cinnamoyl piperazine and homopiperazine compounds.

The compounds of the invention have the formula (I)

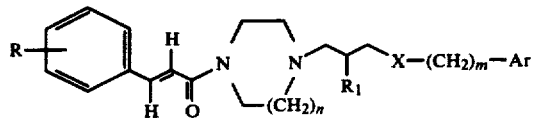

in which

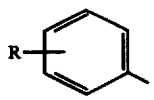

is selected from the group consisting of

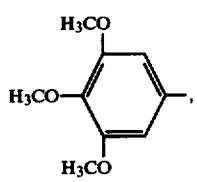

4-fluorophenyl, 3,5-dimethoxyphenyl, 3,4-methylenedioxyphenyl,

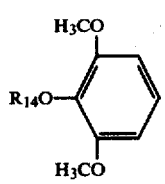

in which $R_{14}$ is hydrogen or linear or branched alkyl having 2 or 3 carbon atoms, and

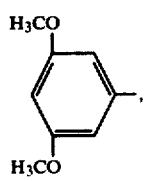

and in which
I. when

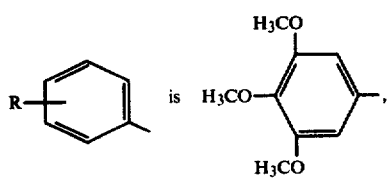

the parameters (n, $R_1$, X, m) are selected from the group consisting of (1, OH, oxygen, zero), (2, OH, oxygen, zero), (1, H, oxygen, zero), (1, OH, S, zero),

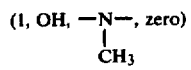

and (1, OH, oxygen, 1), and in which
A. when (n, $R_1$, X, m) is (1, OH, oxygen, zero), Ar is selected from the group consisting of

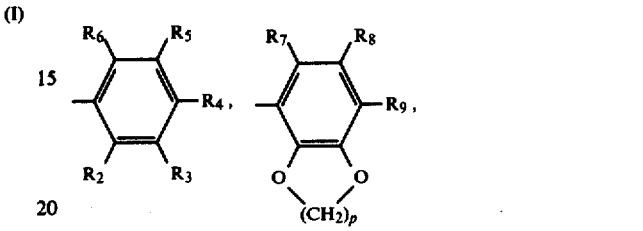

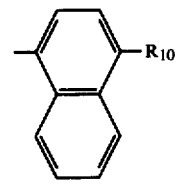

in which $R_{10}$ is acetyl, acetamido or N-methylcarbamoylamino,

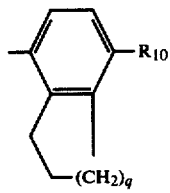

in which q is 1 or 2 and $R_{10}$ has the same meaning as defined above,

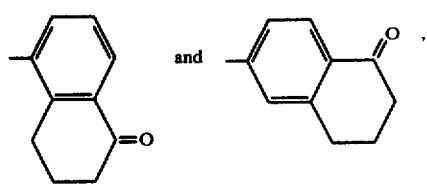

and in which
1. when Ar is

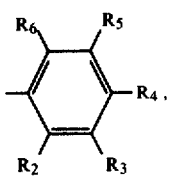

$R_2$, $R_3$, $R_4$, $R_5$ and $R_6$ are selected from the group consisting of
a. $R_3=R_4=R_5=R_6=H$, and $R_2$ is chloro, fluoro, acetamido, acetyl, cyano, methoxy, methyl, allyl or allyloxy, b. $R_2=R_4=R_5=R_6=H$, and $R_3$ is acetamido, methyl, acetyl, cyano, methoxy or chloro,
c. $R_2=R_3=R_5=R_6=H$, and $R_6$ is chloro, cyano, nitro, methylthio, benzoyl, ethyl carboxylate, methyl, linear or branched alkyl having from 3 to 5 carbon atoms, cyclohexyl, alkanoyl in which the alkyl has from 1 to 3 carbon atoms, alkanoylamino in which the alkyl has from 1 to 3 carbon atoms, carboxamido, N-methylcarboxamido, cyanomethyl, carboxamidomethyl or N-methylcarbamoylamino,
d. $R_3=R_5=R_6=H$, $R_2$ is fluoro and $R_4$ is acetyl,
e. $R_3=R_5=R_6=H$, $R_2$ is chloro and $R_4$ is nitro, acetyl, or N-methylcarbamoylamino,
f. $R_3=R_5=R_6=H$, $R_2$ is methyl and $R_4$ is chloro, acetyl, acetamido or N-methylcarbamoylamino,
g. $R_3=R_5=R_6=H$, $R_2$ is methoxy and $R_4$ is acetyl, propionyl, formyl, cyano, acetamido, or N-methylcarboxamido,
h. $R_4=R_5=R_6=H$, and $R_2$ and $R_3$ are methoxy,
i. $R_3=R_4=R_5=H$, and $R_2$ and $R_6$ are methoxy,
j. $R_2=R_4=R_6=H$, and $R_3$ and $R_5$ are methoxy,
k. $R_2=R_5=R_6=H$, and $R_3$ and $R_4$ together are methylenedioxy.
l. $R_2=R_5=R_6=H$, $R_3$ is methyl and $R_4$ is nitro, acetamido or N-methylcarbamoylamino,
m. $R_2=R_6=H$, and $R_3$, $R_4$ and $R_5$ are methoxy,
n. $R_2=R_6=H$, $R_3$ and $R_5$ are methyl, and $R_4$ is chloro,
o. $R_5=R_6=H$, $R_2$ and $R_3$ are methoxy and $R_4$ is N-methylcarbamoylamino,
p. $R_3=R_5=H$, $R_2$ and $R_6$ are chloro, and $R_4$ is acetyl or N-methylcarbamoylamino,
q. $R_3=R_5=H$, $R_2$ and $R_6$ are methoxy and $R_4$ is acetyl, ethyl carboxylate or N-methylcarbamoylamino, and
r. $R_6=H$, $R_3$, $R_4$ and $R_5$ are methoxy and $R_2$ is acetyl, and in which
2. when Ar is

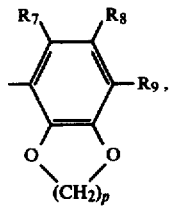

p, $R_7$, $R_8$ and $R_9$ are selected from the group consisting of
a. p=2, $R_7=R_8=H$, and $R_9$ is hydrogen, hydroxy, acetoxy, methoxy, methyl, ethyl, cyano, acetyl, n-butyroyl, alkoxycarbonyl in which the alkoxy is linear or branched and has from 2 to 5 carbon atoms, cyclohexyloxycarbonyl, carboxamido, N-methylcarboxamido, N-cyclohexylcarboxamido, N-phenylcarboxamido, alkanoylamino in which the alkyl is linear or branched and has from 1 to 5 carbon atoms, cyclohexylcarbonylamino, benzoylamino, N-alkylcarbamoylamino in which the alkyl is linear or branched alkyl and has from 1 to 5 carbon atoms, N-cyclohexylcarbamoylamino, N-phenylcarbamoylamino, N-(paramethoxy-phenyl)-carbamoylamino, N,N-dimethylcarbamoylamino, morpholinocarbonylamino, N,N'-dimethylcarbamoylamino, ethoxycarbonylamino, hydroxymethyl, cyanomethyl, ethyl acetate, carboxamidomethyl or N-methylcarboxamidomethyl,
b. p=2, $R_7=R_9=H$, and $R_8$ is acetyl,
c. p=2, $R_8=R_9=H$, and $R_7$ is acetamido,
d. p=1 or 3, $R_7=R_8=H$, and $R_9$ is hydrogen, acetyl, acetamido or N-methylcarbamoylamino, B. when (n, $R_1$, X, m) is (2, OH, oxygen, zero), Ar is selected from the group consisting of phenyl,

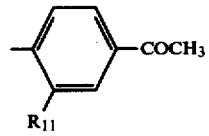

in which $R_{11}$ is hydrogen or methoxy, and

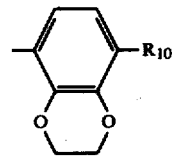

in which $R_{10}$ has the same meaning as previously,

C. when (n, $R_1$, X, m) is (1, H, oxygen, zero), Ar is

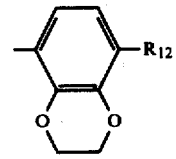

in which $R_{12}$ is acetyl, acetamido, N-methylcarboxamido or N-methylcarbamoylamino, D. when (n, $R_1$, X, m) is (1, OH, S, O), Ar is phenyl, metamethoxyphenyl, paratolyl,

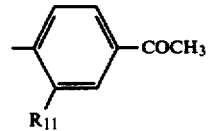

in which $R_{11}$ is hydrogen or methoxy, or

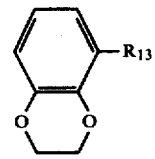

in which $R_{13}$ is hydrogen or acetyl,

E. when (n, $R_1$, X, m) is

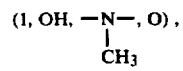

Ar is phenyl, and

F. when (n, R₁, X, m) is (1, OH, oxygen, 1), Ar is phenyl,

II. when

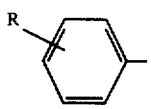

is 4-fluorophenyl, 3,5-dimethoxyphenyl, 3,4-methylenedioxyphenyl, or

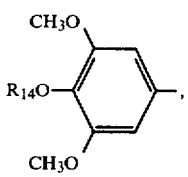

the parameters (n, R₁, X, m) are (1, OH, oxygen, zero) and Ar is

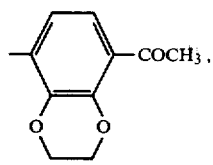

III. when

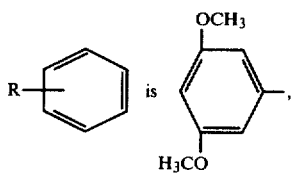

the parameters (n, R₁, X, m) are (1, OH, oxygen, zero) and Ar is

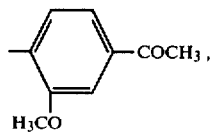

and the pharmacologically acceptable salts thereof.

The process for preparing the compounds of formula (I), except for the 7 following compounds of formula (I):

the compound of formula (I) in which

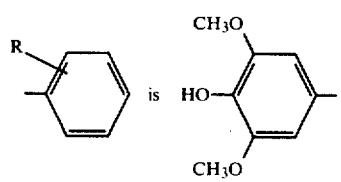

the compound of formula (I) in which X represents the methylamino group

the compound of formula (I) in which Ar is

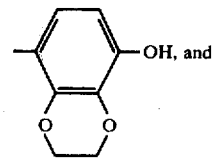

the four compounds of formula (I) in which R₁ represents the hydrogen atom, consists in condensing a piperazine or a homopiperazine of formula (II)

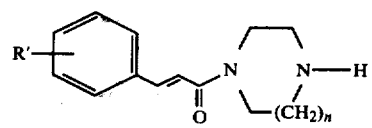

in which n assumes the values 1 and 2 and

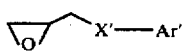

has the same meanings as

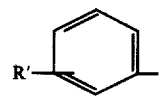

in formula (I) except for the value

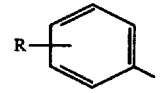

with an epoxy of formula (III):

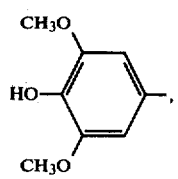

in which Ar' has the same meaning as Ar in formula (I), except for the value

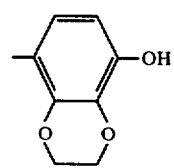

and X' represents oxygen or sulphur, or with 2,3-epoxy-1-benzyloxy propane, to obtain the compound of formula (I) in which m=1.

This condensation is carried out preferably in ethanol with reflux.

Following the same process as above, but from suitable reagents, the compound corresponding to formula (Ia):

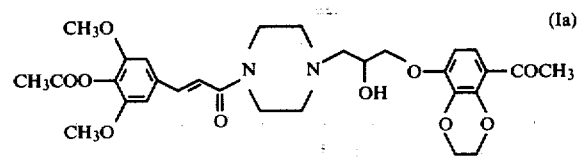

will be prepared.

The novel compounds of formula (II), particularly those corresponding to formulae (IIb) and (IIa).

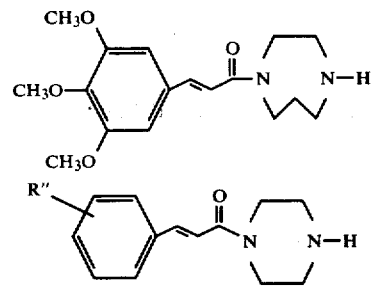

in which

represents the following aromatic groups

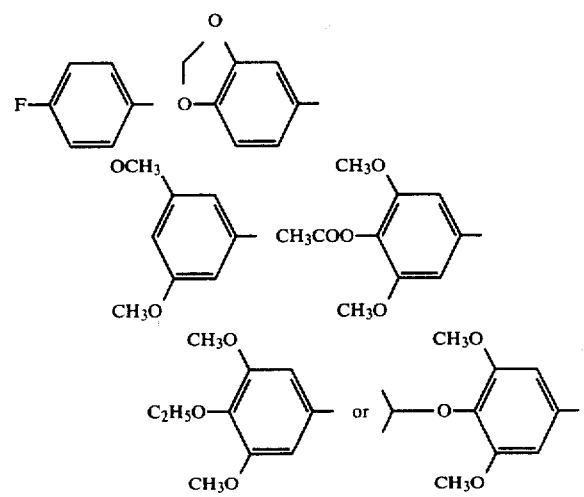

are obtained by condensation of the compounds of formulae (IV) and (IVa):

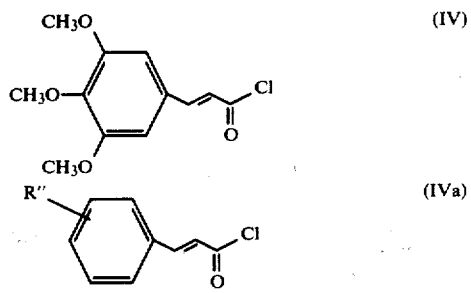

in which R" has the same meanings as in (IIa) respectively, with homopiperazine and piperazine. This condensation is carried out preferably in solution in acetic acid.

The compounds of formula (IVa), particularly those in which

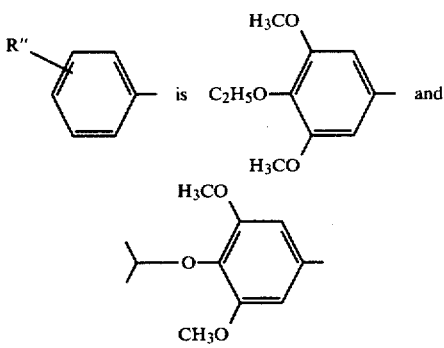

are obtained by action of thionyl chloride, in a toluen solution on corresponding cinnamoic acids of formula (V):

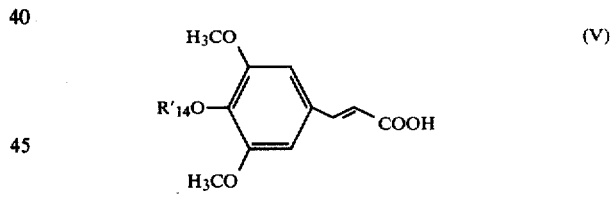

in which $R'_{14}$ represents the ethyl and isopropyl groups.

The compounds (V) are obtained by saponification of the ethyl esters of the corresponding cinnamoic acids of formula (VI):

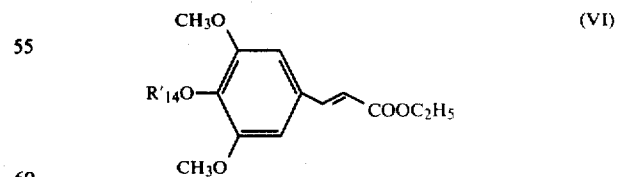

in which $R'_{14}$ has the same meaning as in (V).

The compounds of formula (VI) were used in the crude state and are prepared by action of ethyl iodide or of isopropyl iodide on the ethyl ester of sinapic acid, in solution in acetonitrile and in the presence of potassium carbonate.

The compounds of formula (III):

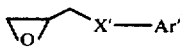
(III)

are partially novel and particularly those in which X' represents an oxygen atom and the Ar' radical represents:

(a) a mono or polysubstituted phenyl nucleus

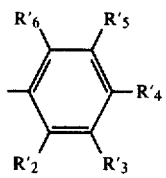

in which $R'_2$, $R'_3$, $R'_4$, $R'_5$ and $R'_6$ represent simultaneously the following values:
$R'_3=R'_5=R'_6=H$; $R'_2=F$; $R'_4=COCH_3$
$R'_3=R'_5=R'_6=H$; $R'_2=OCH_3$; $R'_4=COCH_3$, COEt
$R'_3=R'_5=R'_6=H$; $R'_2=Cl$; $R'_4=COCH_3$, $NO_2$
$R'_2=R'_5=R'_6=H$; $R=_3=CH_3$; $R'_4=NO_2$, NH—CONH—$CH_3$
$R'_5=R'_6=H$; $R'_2=R'_3=OCH_3$; $R'_4=NHCONH—CH_3$
$R'_3=R'_5=H$; $R'_2=R'_6=Cl$; $R'_4=COCH_3$, $NHCONHCH_3$
$R'_3=R'_5=H$; $R'_2=R'_6=OCH_3$; $R'_4=COCH_3$, COOEt, or $NHCONHCH_3$
$R'_6=H$; $R'_3=R'_4=R'_5=OCH_3$; $R'_2=COCH_3$
$R'_2=R'_3=R'_5=R'_6=H$; $R'_4=CH_2—CN$ (b) a heterocycle of formula

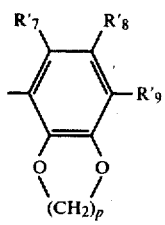

in which p, $R'_7$, $R'_8$ and $R'_9$ assume the following values:

p=2; $R'_7=R'_8=H$; $R'_9$ represents the methoxy, acetoxy, methyl, cyano, acetyl, n-butyroyl, alkoxycarbonyl in which the alkyl is linear or branched and comprises 2 to 5 carbon atoms, cyclohexyloxycarbonyl, carboxamido, N-methylcarboxamido, N-cyclohexylcarboxamido, N-phenylcarboxamido, alkanoylamino whose linear or branched alkyl has 1 to 4 carbon atoms, cyclohexylcarbonylamino, benzoylamino, N-alkylcarbamoylamino whose linear or branched alkyl has from 1 to 5 carbon atoms, N-cyclohexylcarbamoylamino, N-phenylcarbamoylamino, N-(paramethoxyphenyl)carbamoylamino, N,N-diethylcarbamoylamino, morpholino carbonylamino, N,N'-dimethyl carbamoylamino, ethoxycarbonylamino, hydroxymethyl, cyanomethyl, ethylacetate, carboxamidomethyl or N-methylcarboxamidomethyl.

p=2; $R'_7=R'_9=H$; $R'_8$ represents the acetyl group.
p=2; $R'_8=R'_9=H$; $R'_7$ represents the acetamido group.

p=1 or 3; $R'_7=R'_8=H$; $R'_9$ represents the acetyl, acetamido or N-methylcarbamoylamino groups.

(c) a naphthalene nucleus of the type

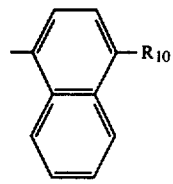

in which $R_{10}$ represents the acetyl, acetamido or N-methylcarbamoylamino groups.

(d) a heterocycle of the type

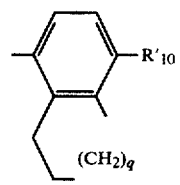

in which q and $R'_{10}$ assume simultaneously the following values:
q=1 in which case $R'_{10}$ represents the acetamido and N-methylcarbamoylamino groups
q=2 in which case $R'_{10}$ represents the acetyl, acetamido or N-methylcarbamoylamino groups.

(e) the group

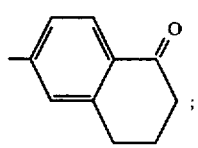

and
—X' represents a sulphur atom and the Ar' radical represents:

(f) an aromatic group

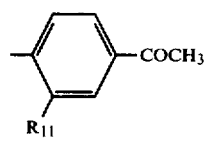

in which $R_{11}$ represents the hydrogen atom or the methoxy group.

(g) a heterocycle of the type

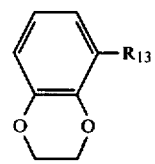

in which $R_{13}$ represents the hydrogen atom or the acetyl group.

The compounds of formula (III) result from the condensation of the phenols of formula (VII):

H—X'—Ar' (VII)

in which X' and Ar' have the same meanings as in formula (III), with epichlorohydrin or epibromohydrin. This condensation is carried out preferably with reflux in acetone or acetonitrile in the presence of potassium carbonate.

The compounds of formula (VII) above are partially novel and they are prepared following different methods according to the nature of X' and Ar.

More exactly:

(1) The compounds of formula (VII) corresponding to formulae (VIIa), (VIIb), (VIIc):

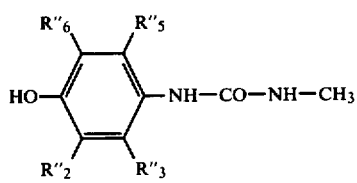
(VIIa)

in which $R''_2$, $R''_3$, $R''_5$ and $R''_6$ assume simultaneously the following values:
$R''_3=R''_5=R''_6=H$; $R''_2=CH_3$
$R''_5=R''_6=H$; $R''_2=R''_3=OCH_3$
$R''_3=R''_5=H$; $R''_2=R''_6=Cl$
$R''_3=R''_5=H$; $R''_2=R''_6=OCH_3$

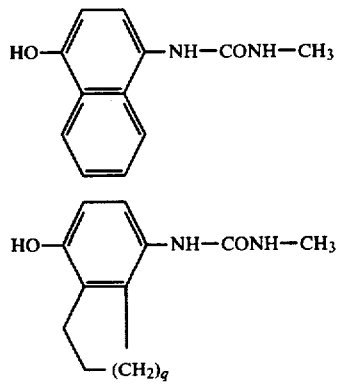
(VIIb)

(VIIc)

in which q assumes the values 1 or 2,
are obtained by action of methyl isocyanate, in a chloroform solution, respectively on the amino phenols of formulae:

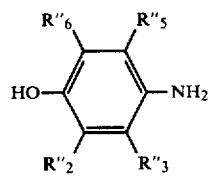
(VIIIa)

in which the values $R''_2$, $R''_3$, $R''_5$ and $R''_6$ have the same meanings as in (VIIa),

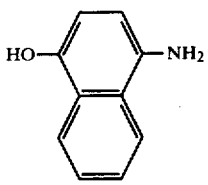
(VIIIb), and

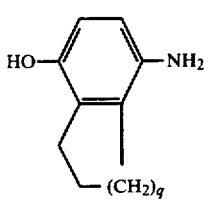
(VIIIc)

in which q assumes the values 1 or 2.

(2) The compounds (VII) corresponding to the formula (VIId):

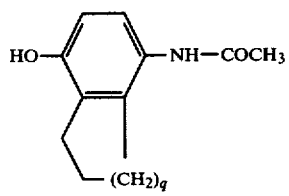
(VIId)

in which q assumes the values 1 or 2, are obtained by condensation of acetic anhydride on the (VIIIc) compounds in an aqueous solution.

(3) The compounds (VII) corresponding to formulae (VIIe) and (VIIf):

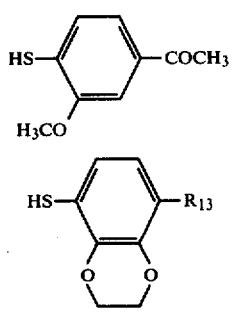
(VIIe)

(VIIf)

in which $R_{13}$ represents the hydrogen atom or the acetyl group are obtained by treatment with a solution of NaOH in methanol of compounds of formulae (IX) and (IXa)

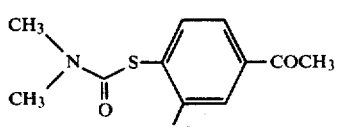
(IX)

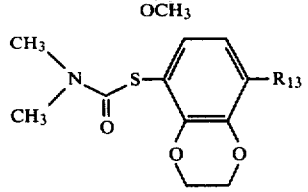
(IXa)

in which $R_{13}$ represents the hydrogen atom or the acetyl group.

The (IX) and (IXa) compounds are obtained by thermal transposition of compounds (X) and (Xa)

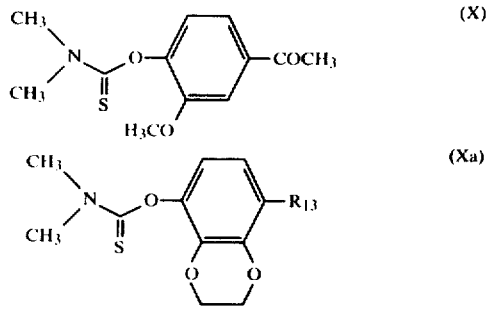

in which $R_{13}$ has the same meanings as in (IXa).

The (X) and (Xa) compounds are themselves obtained by condensatin of N,N-dimethylthiocarbamoyl chloride with phenols of formulae:

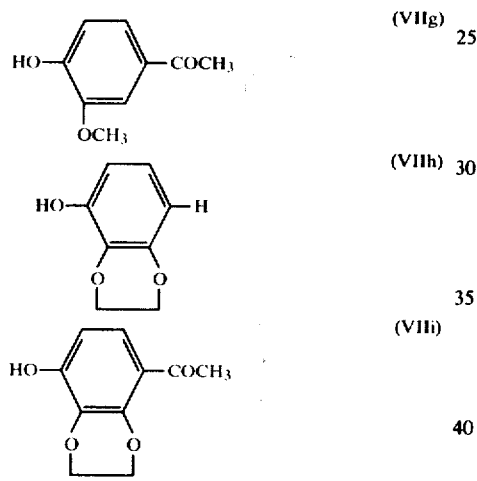

(4) The compounds of formula (VII) corresponding to formula (VIIk)

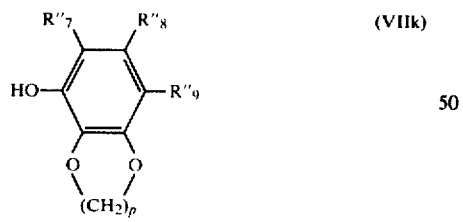

in which p, $R''_7$, $R''_8$ and $R''_9$ assume simultaneously the following values:

p=2; $R''_7=R''_8=H$; $R''_9$ represents the acetoxy, cyano, alkoxy carbonyl in which the alkyl is linear or branched and comprises 2 to 5 carbon atoms, cyclohexyloxy carbonyl, carboxamido, N-methyl carboxamido, N-cyclohexyl carboxamido, N-phenyl carboxamido, alkanoylamino whose alkyl is linear or branched and has 2 to 5 carbon atoms, cyclohexylcarbonylamino, benzoylamino, N-alkyl-carbamoylamino whose alkyl is linear or branched and has 1 to 5 carbon atoms, N-cyclohexylcarbamoylamino, N-phenylcarbamoylamino, N-paramethoxyphenyl carbamoylamino, N,N-dimethyl carbamoylamino, morpholinocarbonylamino, N,N'-dimethylcarbamoylamino, ethoxycarbonylamino, hydroxymethyl, cyanomethyl, ethyl acetate, carboxamidomethyl and N-methylcarboxamidomethyl, p=1 or 3; $R''_7=R''_8=H$; $R''_9$ then represents the acetyl, acetamino or N-methylcarbamoylamino groups, are obtained by hydrogenolysis, in the presence of palladium on charcoal, of compounds of formula (XI)

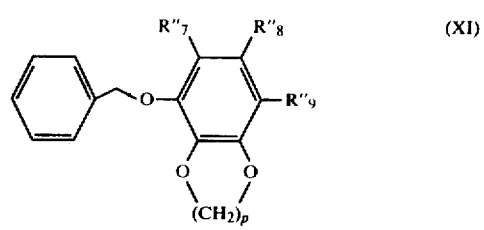

in which p, $R''_7$, $R''_8$ and $R''_9$ have the same meanings as in (VIIk).

(5) The (VII) compound corresponding to the formula (VIII)

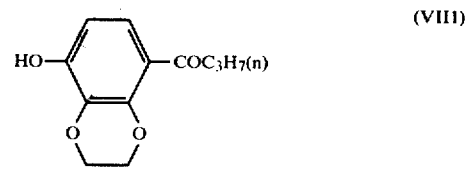

is obtained by the transposition of Fries of the compound of formula (XII)

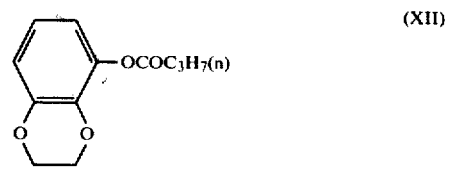

(6) The (VII) compound corresponding to formula (VIIm)

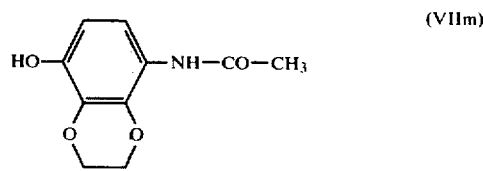

is obtained by a Beckmann rearrangement, in an acetic acid medium, in the presence of hydrochloric acid, of the compound of formula (XIII)

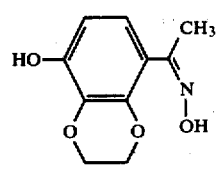

Compound (XIII) is itself obtained by action of hydroxylamine on the compound of formula (VIIi)

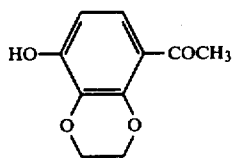

(7) The compound of formula (VII) corresponding to formula (VIIn)

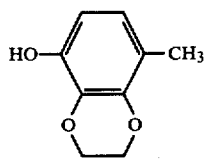

is obtained by hydrogenolysis, in the presence of palladium on 5% charcoal, of the compound of formula (XIp) used in the crude state

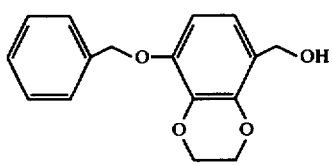

The compounds of formula (XI) above, necessary in the preparation of the compounds of formula (VIIk) are partly novel and are obtained by different processes depending on the nature of p, R''$_7$, R''$_8$ and R''$_9$.

Similarly, the compound of formula (XIa) is novel:

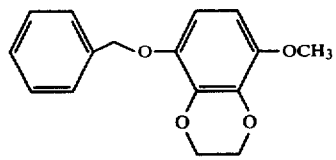

which can be used for the synthesis of a compound of formula (VIIk'), which is known:

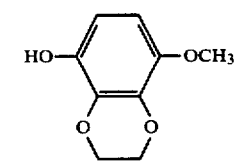

More exactly:

(1) The compound corresponding to formula (XIa)

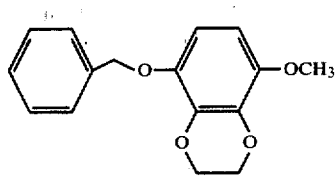

is obtained by action of methyl sulfate on the compound of formula (XIV)

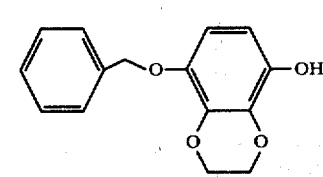

The compound (XIV) is obtained by action of potassium carbonate on the following compound (XIb)

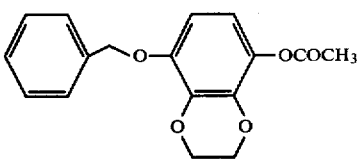

which is itself obtained by Baeyer Williger reaction on the compound of formula (XV)

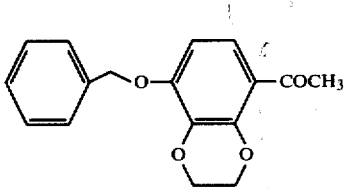

The novel compound (XV) is obtained by action of benzyl chloride, in solution in acetonitrile or acetone, in the presence of potassium carbonate, on the compound (VIIi):

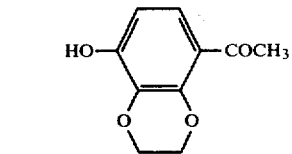

(2) The compounds (XI) corresponding to the formula (XIc):

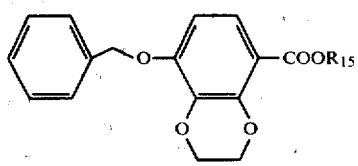

in which R$_{15}$ represents the ethyl, isopropyl, tertbutyl, n-pentyl, or cyclohexyl groups are obtained:

when in (XIc) $R_{15}$ represents the isopropyl, t-butyl, n-pentyl, and cyclohexyl groups, by a synthesis in two stages which consists in treating the compound of formula (XVI)

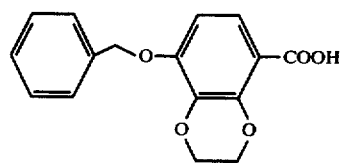
(XVI)

with thionyl chloride, then by reacting the crude product thus obtained with alcohols of formula (XVII):

 (XVII)

in which $R_{15}$ has the same meaning as in formula (XIc), except for the ethyl group, and when in (XIc) $R_{15}$ represents the ethyl group, by action of ethanol in the presence of hydrochloric acid, on the compound of formula (XVI).

The compound of formula (XVI), also novel, is obtained by oxidation by the iodine-pyridine complex, in the presence of soda, of the compound of formula (XV):

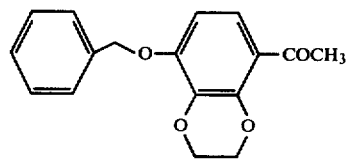
(XV)

(3) The (XI) compounds corresponding to the formula (XId):

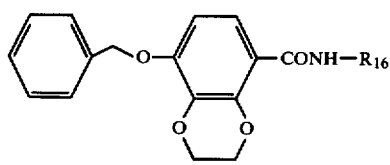
(XId)

in which $R_{16}$ represents either the hydrogen atom or the methyl, cyclohexyl or phenyl groups are obtained:

when $R_{16}$ assumes the above meanings, except for the methyl group, by a two-stage synthesis which consists in treating the compound of formula (XVI) with thionyl chloride, then in reacting on the crude product thus obtained the amines of formula (XVIII)

 (XVIII)

in which $R_{16}$ represents the hydrogen atom or a cyclohexyl or phenyl group, and when $R_{16}$ represents the methyl group, from the compound of formula (XVI) following the process of mixed anhydrides (with methylamine).

(4) The compounds (XI) corresponding to formula (XIe):

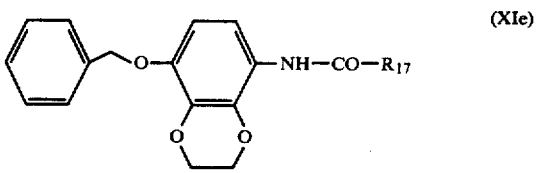
(XIe)

in which $R_{17}$ represents either a linear or branched alkyl group having from 2 to 5 carbon atoms, or the cyclohexyl group, or the phenyl group, are obtained by action of acid chlorides of formula (XIX):

 (XIX)

in which $R_{17}$ has the same meanings as in (XIe), on the compounds of formula (XX):

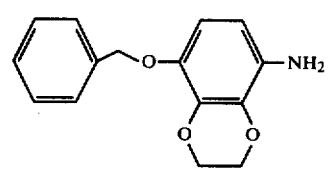
(XX)

in a tetrahydrofuran medium.

(5) The compounds of formula (XI) corresponding to formula (XIf):

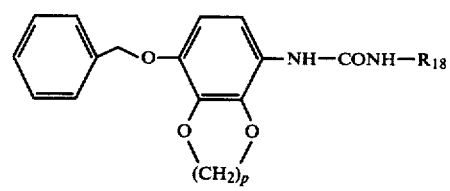
(XIf)

in which p and $R_{18}$ assume simultaneously the following values:

p=2; $R_{18}$ represents either a linear or branched alkyl group having 1 to 5 carbon atoms or the cyclohexyl, phenyl or paramethoxyphenyl groups, p=1 or 3; $R_{18}$ represents the methyl group, are obtained by action of isocyanates of formula (XXI):

 (XXI)

on the compounds of formula (XX) above and (XXa)

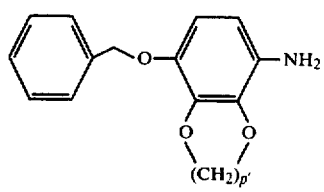
(XXa)

in which p' assumes the values 1 or 3.

(6) The compound (XI) corresponding to formula (XIg):

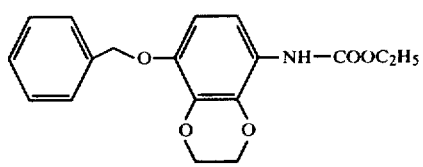
(XIg)

is obtained by action of ethyl chloroformate on the compound of formula (XX) above.

The compounds of formulae (XX) and (XXa) used in the synthesis given under items (4), (5) and (6) above are novel and are obtained by hydrolysis, with potash (KOH) in ethanol, of the compounds of formula (XIh)

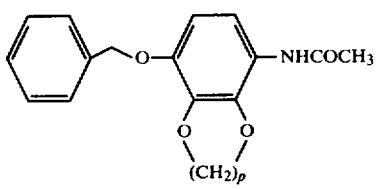
(XIh)

in which p assumes the values 1, 2 or 3.

The compounds of formula (XIh) are, for their part, obtained:
either by a Beckmann rearrangement, in an acid medium, of the compounds of formula (XXII):

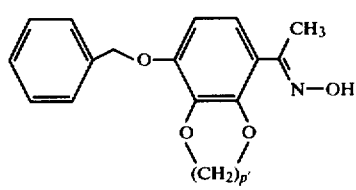
(XXII)

in which p' assumes the values 1 or 3.
or by action of benzyl chloride on the compound of formula (VIIm):

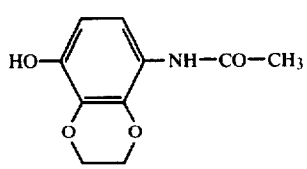
(VIIm)

in an acetone solution, in the presence of potassium carbonate.

The compounds of formula (XXII) above are obtained by action of hydroxylamine on the compounds of formula (XIi):

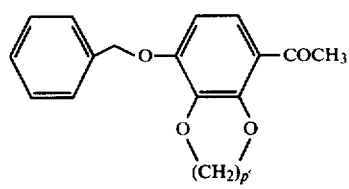
(XIi)

in which p' assumes the values 1 or 3.

The compounds of formula (XIi) are obtained by action of a di-iodated or dibrominated derivative of formula (XXIII):

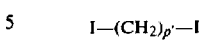

or

(XXIII)

in which p' assumes the value 1 or 3, on the compound of formula (XXIV):

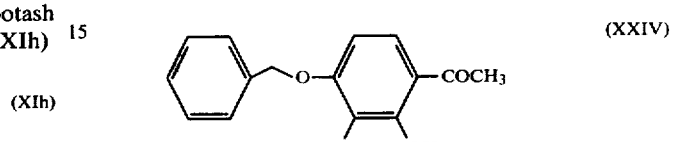
(XXIV)

in solution in dimethyl sulfoxide or N,N-dimethylformamide in the presence of potash (KOH).

Compound (XXIV) is obtained by action of benzyl chloride on gallacetophenone.

(7) The compound (XI) corresponding to formula (XIj):

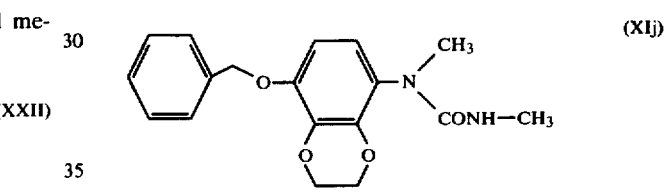
(XIj)

is obtained by action of methyl isocyanate on compound (XXV):

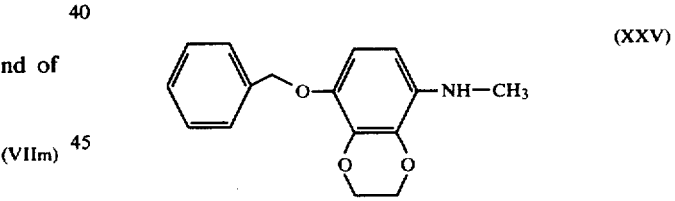
(XXV)

Compound (XXV) is obtained by a synthesis in two steps which consists in treating the compound of formula (XX) with a mixture of formaldehyde and 5,5-dimethylhydantoin in an ethanol solution, then in reacting on the crude reaction product, sodium borohydride in solution in dimethylsulfoxide, at a temperature of 100° C.

(8) Compound (XI) corresponding to formula (XIk):

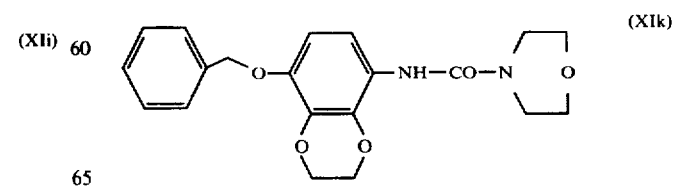
(XIk)

is obtained by action of morpholine at reflux on the compound of formula (XIg):

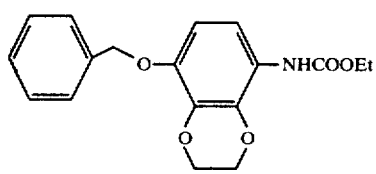 (XIg)

(9) Compound (XI) corresponding to formula (XII):

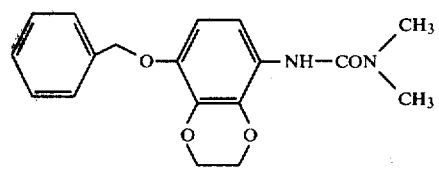 (XII)

is obtained by action of N,N-dimethylcarbamoyl chloride on the compound of formula (XX).

(10) Compound (XI) corresponding to formula (XIm):

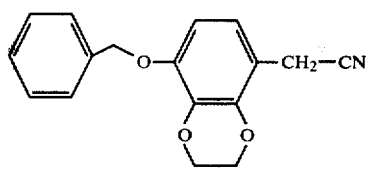 (XIm)

is obtained by action of sodium cyanide on the compound of formula (XXVI):

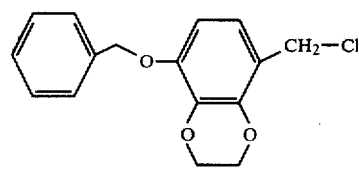 (XXVI)

Compound (XXVI) is obtained by action of thionyl chloride on compound (XIp), hereafter described.

(11) Compound (XI) corresponding to formula (XIn):

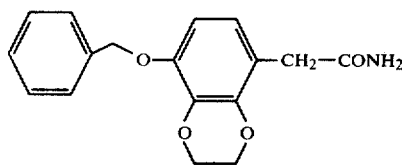 (XIn)

is obtained by treating compound (XIm):

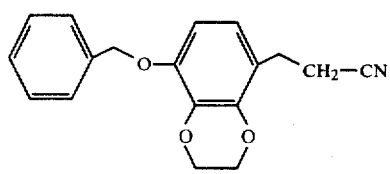 (XIm)

by potash (KOH) in solution in t-butanol.

(12) Compound (XI) corresponding to formula (XIo):

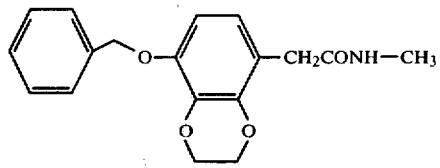 (XIo)

is obtained by action of methylamine following the mixed anhydride method on the compound of formula (XXVII):

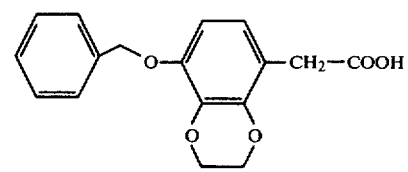 (XXVII)

Compound (XXVII) is obtained by saponification with an aqueous solution of NaOH of compound (XIm).

(13) Compound (XI) corresponding to formula (XIp):

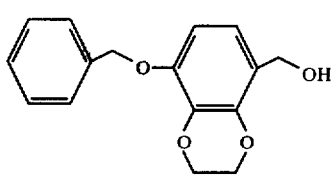 (XIp)

is obtained by reduction with the double hydride of lithium and aluminum of the compound of formula (XIc), in which $R_{15}$ represents the ethyl group.

(14) Compound (XI) corresponding to formula (XIq):

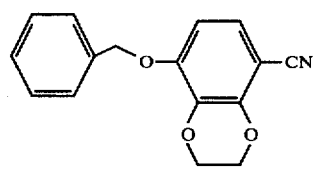 (XIq)

is obtained by action of phosphorous pentachloride on the compound (XId) in which $R_{16}$ represents the hydrogen atom.

(15) Compound (XI) corresponding to formula (XIr):

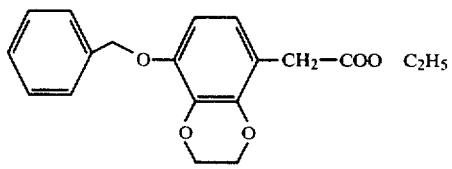 (XIr)

is obtained by action of ethanol, in the presence of hydrochloric acid, on the compound of formula (XXVII):

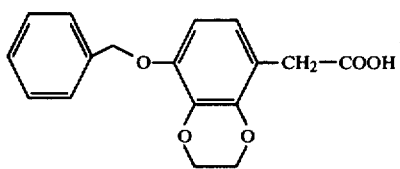
(XXVII)

The process for the preparation of the compounds of formula (I) in which:

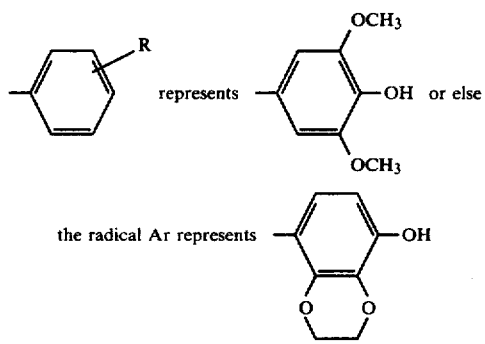

consists in hydrolyzing the acetoxy group of compounds of formulae (Ia) and (Ib)

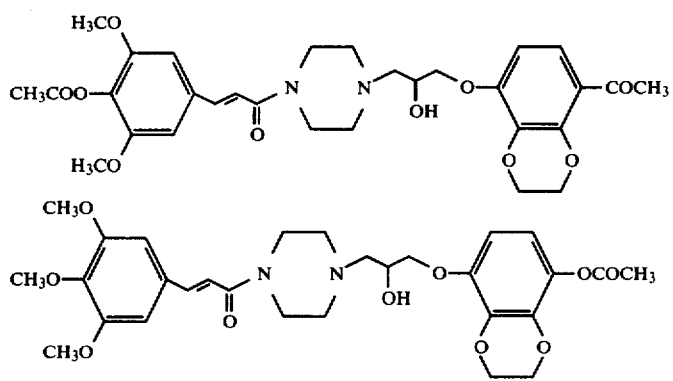

with an alcohol solution of sodium bicarbonate.

The compounds of formulae (Ia) and (Ib) are obtained by a process identical to that used for the synthesis of compounds of formula (I) previously described.

The process for the preparation of the compounds of formula (I) in which X represents the methylamino group:

consists in condensing an epoxy of formula (IIIh):

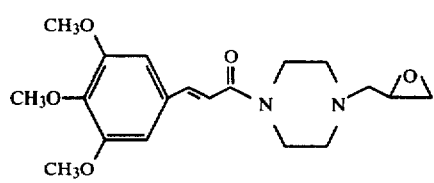
(IIIh)

with N-methylaniline in an alcohol medium.

The compound of formula (IIIh) is obtained by condensing epibromohydrin on 3,4,5-trimethoxy cinnamoylpiperazine of formula (IIc):

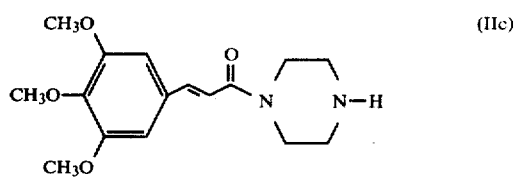
(IIc)

in solution in acetonitrile, in the presence of potassium carbonate.

The process for the preparation of compounds of formula (I), in which $R_1$ represents the hydrogen atom consists in condensing piperazine of formula (IIc) above with a chlorinated derivative of formula (XXVIII):

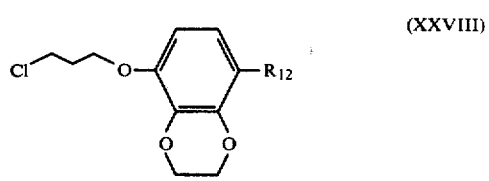
(XXVIII)

in which $R_{12}$ represents the acetyl, acetamido, N-methyl carboxamido or N-methylcarbamoylamino groups in solution in acetonitrile, in the presence of potassium carbonate.

The novel compounds of formula (XXVIII) are obtained by condensation of 1-bromo-3-chloropropane with the phenols of formula (VII):

H—X'—Ar'  (VII)

in which X' represents the oxygen atom and Ar' is

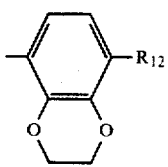

in which $R_{12}$ has the same meanings as in formula (XXVIII).

The following preparations are given by way of example to illustrate the invention.

EXAMPLE 1

1-[3-(2-methyl-4-acetyl)phenyl-2-hydroxy]-propyl-4-(3,4,5-trimethoxy cinnamoyl)piperazine chlorhydrate (I)

Code number: 770 993

A mixture of 9.2 g of 3,4,5-trimethoxy cinnamoyl piperazine and 6.2 g of 1-(2-methyl-4-acetylphenyl)-2,3-epoxy propane in 65 ml of ethanol was brought to reflux for 4 hours. The solvent was evaporated and the residue was chromatographed on a silica column eluted by chloroform-methanol: 98%/2% mixture and 12 g of an oil was obtained which was dissolved in acetone. Then, a gaseous current of dry hydrochloric acid was passed until an acid pH was obtained, then the precipitate obtained was filtered.

Yield: 45%
Melting Point: 140° C.
Empirical formula: $C_{28}H_{37}ClN_2O_7$
Molecular weight: 549.05

| Elementary analysis: | C | H | N |
| --- | --- | --- | --- |
| Calculated % | 61.25 | 6.79 | 5.10 |
| Obtained % | 61.12 | 6.62 | 5.04 |

By the same process, but from corresponding reagents, the compounds of formula I, given in the following Table I, were obtained, except for the compounds of formula I in which $R_1=H$ which are obtained with the process of Example 3, for the compounds of code number 770 274 and 780 120 (obtained in Example 2) and 770 495 (obtained in Example 4).

TABLE I

[Structure: Ar-CH=CH-C(O)-N-piperazine-N-CH2-CH(R1)-X-(CH2)m-Ar' with R substituent on phenyl] (I)

| Code Number | R | n | R₁ | X | m | -Ar | Form | Empirical Formula | Molecular weight | Melting point (°C.) | Yield % | ELEMENTARY ANALYSIS | C | H | N |
|---|---|---|---|---|---|---|---|---|---|---|---|---|---|---|---|
| 770993 | [3,4,5-trimethoxyphenyl: OCH₃, CH₃O, OCH₃] | 1 | OH | Oxygen | 0 | [phenyl with COCH₃ and OCH₃] | HCl | $C_{28}H_{37}ClN_2O_7$ | 549.05 | 140 | 45 | Cal. %<br>Obt. % | 61.25<br>61.12 | 6.79<br>6.62 | 5.10<br>5.04 |
| 770194 | [methylenedioxyphenyl] | " | " | " | " | [benzodioxole with COCH₃] | oxalate | $C_{29}H_{32}N_2O_{12}$ + 3/2 H₂O | 627.59 | 118 | 71 | Cal. %<br>Obt. % | 55.50<br>55.85 | 5.62<br>5.48 | 4.46<br>4.71 |
| 770199 | [4-fluorophenyl: F] | " | " | " | " | " | " | $C_{28}H_{31}FN_2O_{10}$ + 4/5 H₂O | 588.96 | 136 | 79 | Cal. %<br>Obt. % | 57.10<br>56.97 | 5.58<br>5.28 | 4.76<br>4.88 |
| 770504 | [trisubstituted: OCH₃, C₂H₅O, OCH₃] | " | " | " | " | " | " | $C_{32}H_{40}N_2O_{13}$ | 660.56 | 191 | 58 | Cal. %<br>Obt. % | 58.17<br>57.87 | 6.10<br>6.13 | 4.24<br>4.29 |
| 770538 | [3,5-dimethoxyphenyl: OCH₃, OCH₃] | " | " | " | " | " | Base | $C_{28}H_{34}N_2O_8$ | 526.57 | 168 | 63 | Cal. %<br>Obt. % | 63.86<br>63.56 | 6.51<br>6.41 | 5.32<br>5.01 |

TABLE I-continued $$\text{Structure: } R\text{-phenyl-CH=CH-C(O)-N(piperazine)-N-CH}_2\text{-CHR}_1\text{-X-(CH}_2)_m\text{-A}_r \quad (I)$$

with $(CH_2)_n$ on piperazine nitrogen

| Code Number | R | n | $R_1$ | X | m | $-A_r$ | Form | Empirical Formula | Molecular weight | Melting point (°C) | Yield % | Elementary Analysis C / H / N |
|---|---|---|---|---|---|---|---|---|---|---|---|---|
| 770727 | 3,5-(OCH$_3$)$_2$-4-O-iPr | " | " | " | " | " | HCl | C$_{31}$H$_{41}$ClN$_2$O$_9$ + 5/3 H$_2$O | 651.14 | 145 | 27 | Cal. % 57.18 / 6.86 / 4.30<br>Obt. % 57.45 / 6.42 / 4.39 |
| 770276 | 3,5-(OCH$_3$)$_2$-4-OCH$_3$ | " | " | " | 1 | phenyl | HCl | C$_{26}$H$_{35}$ClN$_2$O$_6$ + 2/3 H$_2$O | 519.02 | 170 | 90 | Cal. % 60.16 / 7.06 / 5.40<br>Obt. % 60.04 / 6.75 / 5.55 |
| 770307 | " | " | " | " | 0 | benzodioxole-NHCONH—C$_2$H$_5$ | HCl | C$_{30}$H$_{41}$ClN$_4$O$_3$ + H$_2$O | 655.133 | 172 | 65 | Cal. % 55.00 / 6.62 / 8.55<br>Obt. % 54.80 / 6.57 / 8.49 |
| 770312 | " | " | " | " | " | benzodioxole-CH$_2$—COOC$_2$H$_5$ | HCl | C$_{31}$H$_{41}$ClN$_2$O$_{10}$ + 2/3 H$_2$O | 649.111 | 156 | 94 | Cal. % 57.36 / 6.57 / 4.32<br>Obt. % 57.45 / 6.60 / 4.11 |
| 770382 | " | " | " | " | " | benzodioxole-CH$_2$—CONH—CH$_3$ | HCl | C$_{30}$H$_{40}$ClN$_3$O$_9$ + 1 1/6 H$_2$O | 643.120 | 180 | 87 | Cal. % 56.02 / 6.64 / 6.53<br>Obt. % 55.99 / 6.54 / 6.45 |

TABLE I-continued

Structure (I):

$$R-C_6H_4-C(=O)-N\text{-piperazine-}N-CHR_1-CH_2-X-(CH_2)_m-A_r$$

| Code Number | n | $R_1$ | X | m | $-A_r$ | Form | Empirical Formula | Molecular weight | Melting point (°C.) | Yield % | Elementary Analysis C | H | N |
|---|---|---|---|---|---|---|---|---|---|---|---|---|---|
| 770386 | " | " | " | " | benzodioxole-CH₃, CH₂—CONH₂ | HCl | $C_{29}H_{38}ClN_3O_9$ + 1.5 H₂O | 635.099 | 180 | 65 | Cal. % 54.84 Obt. % 55.00 | 6.51 6.27 | 6.62 6.61 |
| 770458 | " | " | " | " | phenyl-CH₃, COCH₃ | HCl | $C_{27}H_{35}ClN_2O_7$ | 535.02 | 132 | 59 | Cal. % 60.61 Obt. % 60.67 | 6.59 6.53 | 5.24 5.18 |
| 770483 | " | " | " | " | benzodioxole-CH₃, NH—CONH—C₃H₇n | Oxalate | $C_{33}H_{44}N_4O_{13}$ | 704.714 | 200 | 95 | Cal. % 56.24 Obt. % 55.96 | 6.29 6.29 | 7.95 7.86 |
| 770487 | " | " | " | " | phenyl-CH₃, NH—COCH₃, OCH₃ | Oxalate | $C_{30}H_{39}N_3O_{12}$ + 1/2 H₂O | 642.64 | 170 | 36 | Cal. % 56.07 Obt. % 55.94 | 6.28 6.08 | 6.54 6.52 |
| 770488 | " | " | " | " | phenyl-CH₃, CH₂—CN | " | $C_{29}H_{36}N_3O_{10}$ + 3/5 H₂O | 596.40 | 115 | 36 | Cal. % 58.40 Obt. % 58.53 | 6.12 5.75 | 7.05 7.13 |
| 770525 | " | " | " | " | benzodioxole-CH₃, NH—COOC₂H₅ | Oxalate | $C_{32}H_{41}N_3O_{14}$ + 1/2 H₂O | 700.68 | 162 | 96 | Cal. % 54.85 Obt. % 55.02 | 6.04 5.97 | 6.00 5.89 |

TABLE I-continued

| Code Number | n | $R_1$ | X | m | $-A_r$ | Form | Empirical Formula | Molecular weight | Melting point (°C.) | Yield % | ELEMENTARY ANALYSIS | | |
|---|---|---|---|---|---|---|---|---|---|---|---|---|---|
| | | | | | | | | | | | C | H | N |
| 770529 | " | " | " | " | NH—CO—(phenyl), methyl-benzodioxole | " | $C_{36}H_{41}N_3O_{13}$ + 3/5 $H_2O$ | 734.521 | 177 | 93 | Cal. % 58.86  Obt. % 59.05 | 5.79  5.40 | 5.72  5.96 |
| 770533 | " | " | " | " | NH—CO—(cyclohexyl), methyl-benzodioxole | " | $C_{36}H_{47}N_3O_{13}$ + 3/4 $H_2O$ | 743.372 | 195 | 98 | Cal. % 58.17  Obt. % 58.15 | 6.58  6.40 | 5.65  5.72 |
| 770545 | " | " | " | " | NH—CO—$C_2H_5$, methyl-benzodioxole | " | $C_{32}H_{41}N_3O_{13}$ + 2/5 $H_2O$ | 682.878 | 165 | 100 | Cal. % 56.28  Obt. % 55.98 | 6.17  6.00 | 6.15  6.18 |
| 770581 | " | " | " | " | $CONH_2$, methyl-benzodioxane | Oxalate | $C_{29}H_{36}N_3O_{11}$ + 1/5 $H_2O$ | 629.626 | 178 | 52.5 | Cal. % 52.32  Obt. % 55.14 | 6.24  6.31 | 6.67  6.66 |
| 770585 | " | " | " | " | CN, methyl-benzodioxane | Base | $C_{28}H_{33}N_3O_8$ | 539.568 | 154 | 82.5 | Cal. % 62.32  Obt. % 62.25 | 6.16  6.26 | 7.79  7.80 |

TABLE I-continued

| Code Number | n | R₁ | X | m | −Ar | Form | Empirical Formula | Molecular weight | Melting point (°C.) | Yield % | | ELEMENTARY ANALYSIS | | | |
|---|---|---|---|---|---|---|---|---|---|---|---|---|---|---|---|
| | | | | | | | | | | | | C | H | N | |
| 770590 | " | " | " | " | COCH₃ (benzodioxane, methyl) | Oxalate | C₃₁H₃₈N₂O₁₃ + 3/5 H₂O | 657.44 | 172 | 18 | Cal. % Obt. % | 56.63 56.86 | 6.01 5.85 | 4.26 4.13 |
| 770601 | " | " | " | " | NH—CO—C₄H₉n (benzodioxane, methyl) | " | C₃₄H₄₅N₃O₁₃ + 4/5 H₂O | 718.136 | 177 | 97.5 | Cal. % Obt. % | 56.86 57.06 | 6.54 6.32 | 5.85 5.72 |
| 770610 | " | " | " | " | NH—COC₃H₇n (benzodioxane, methyl) | " | C₃₃H₄₃N₃O₁₃ + 1/5 H₂O | 693.301 | 190 | 100 | Cal. % Obt. % | 57.17 57.42 | 6.31 6.17 | 6.06 6.05 |
| 770614 | " | " | " | " | NH—CO—C(CH₃)₃ (benzodioxane, methyl) | " | C₃₄H₄₅N₃O₁₃ | 707.724 | 203 | 100 | Cal. % Obt. % | 58.03 57.74 | 6.45 6.25 | 5.97 5.91 |
| 770622 | " | " | " | 2 | COCH₃ (benzodioxane, methyl) | HCl | C₃₀H₃₉ClN₂O₉ + 1/5 H₂O | 639.51 | 85 | 17 | Cal. % Obt. % | 56.34 56.10 | 6.71 6.78 | 4.38 4.14 |

TABLE I-continued $$\text{Structure (I):} \quad R\text{-}C_6H_4\text{-}CH=CH\text{-}CO\text{-}N(\text{piperazine})\text{-}CH_2\text{-}CHR_1\text{-}CH_2\text{-}X\text{-}(CH_2)_m\text{-}A_r \quad (I)$$

with $(CH_2)_n$ substituent.

| Code Number | R | n | R₁ | X | m | −Aᵣ | Form | Empirical Formula | Molecular weight | Melting point (°C.) | Yield % | | ELEMENTARY ANALYSIS | | |
|---|---|---|---|---|---|---|---|---|---|---|---|---|---|---|---|
| | | | | | | | | | | | | | C | H | N |
| 770630 | " | 1 | " | " | " | 8-methyl-benzodioxane-NH–CO–NH–CH(CH₃)₂ | Oxalate | C₃₃H₄₄N₄O₁₃ | 704.714 | 198 | 90 | Cal. %<br>Obt. % | 56.24<br>55.93 | 6.29<br>6.37 | 7.95<br>8.14 |
| 770634 | " | " | " | " | " | 8-methyl-benzodioxane-NH–CONH–C₄H₉ⁿ | Oxalate | C₃₄H₄₆N₄O₁₃ + 3/5 H₂O | 729.549 | 175 | 90 | Cal. %<br>Obt. % | 55.97<br>55.75 | 6.52<br>6.33 | 7.68<br>7.59 |
| 770692 | " | " | " | " | " | 8-methyl-benzodioxane-NH–CO–CH(CH₃)₂ | Oxalate | C₃₃H₄₃N₃O₁₃ + 2/3 H₂O | 701.709 | 192 | 99 | Cal. %<br>Obt. % | 56.48<br>56.48 | 6.37<br>6.34 | 5.99<br>5.90 |
| 770711 | " | " | " | " | " | 8-methyl-benzodioxane-NH–CONH–C(CH₃)₃ | Oxalate | C₃₄H₄₆N₄O₁₃ | 718.740 | 168 | 65 | Cal. %<br>Obt. % | 56.81<br>56.86 | 6.45<br>6.56 | 7.80<br>7.96 |
| 770738 | " | " | " | " | " | 2-methyl-phenyl-NHCOCH₃ | Oxalate | C₂₇H₃₅N₃O₇ + 1.78 (COOH)₂ + 1.75 H₂O | 699.96 | 119 | 23 | Cal. %<br>Obt. % | 52.23<br>52.11 | 6.04<br>5.69 | 6.00<br>5.84 |

TABLE I-continued

General structure: R-phenyl-CH=CH-C(O)-N(piperazine)-N-(CH₂)ₙ-CHR₁-X-(CH₂)ₘ-Ar  (I)

| Code Number | n | R₁ | X | m | —Ar | Form | Empirical Formula | Molecular weight | Melting point (°C.) | Yield % | | ELEMENTARY ANALYSIS | | |
|---|---|---|---|---|---|---|---|---|---|---|---|---|---|---|
| | | | | | | | | | | | | C | H | N |
| 770855 | " | " | " | " | 3-OCH₃-4-CH₃-phenyl-CONH-CH₃ | HCl | C₂₈H₃₈ClN₃O₈ + 2 H₂O | 616.10 | 173 | 73 | Cal. % / Obt. % | 54.58 / 54.56 | 6.60 / 6.49 | 7.24 / 6.92 |
| 770858 | " | " | " | " | 4-isopropylphenyl | HCl | C₂₈H₃₉ClN₂O₆ | 535.06 | 204 | 68 | Cal. % / Obt. % | 62.85 / 63.09 | 7.35 / 7.54 | 5.24 / 5.20 |
| 770859 | " | " | " | " | 4-tert-butylphenyl | HCl | C₂₉H₄₁ClN₂O₆ + 1/6 H₂O | 552.09 | 210 | 94 | Cal. % / Obt. % | 63.09 / 63.13 | 7.55 / 7.47 | 5.02 / 5.29 |
| 770898 | " | " | " | " | 2-CH₃-4-(NH-CONH-CH₃)-phenyl | Base | C₂₈H₃₈N₄O₇ + 3/5 H₂O | 553.42 | 136 | 41 | Cal. % / Obt. % | 60.76 / 60.40 | 7.14 / 7.38 | 10.12 / 9.21 |
| 770831 | " | " | " | " | cyclohexyl-CONH-benzodioxane | Oxalate | C₃₆H₄₇N₃O₁₃ | 729.760 | 207 | 54 | Cal. % / Obt. % | 59.25 / 59.08 | 6.49 / 6.38 | 5.76 / 6.08 |
| 770844 | " | " | " | " | 3-(NH-COCH₃)-phenyl | Base | C₂₇H₃₅N₃O₇ + 1 H₂O | 531.59 | 103 | 46 | Cal. % / Obt. % | 61.00 / 60.81 | 7.02 / 7.25 | 7.91 / 8.08 |

TABLE I-continued

Structure (I):

R-C₆H₄-CH=CH-C(O)-N[piperazine]-(CH₂)ₙ-CH(R₁)-CH₂-X-(CH₂)ₘ-Ar    (I)

| Code Number | R | n | R₁ | X | m | —Ar | Form | Empirical Formula | Molecular weight | Melting point (°C.) | Yield % | | ELEMENTARY ANALYSIS C | H | N |
|---|---|---|---|---|---|---|---|---|---|---|---|---|---|---|---|
| 770848 | (as above) | " | " | " | " | 8-methyl-2,3-dihydro-1,4-benzodioxin-5-yl-CONH | Oxalate | C₃₆H₄₁N₃O₁₃ + 1/3 H₂O | 729.717 | 173 | 100 | Cal. % Obt. % | 59.25 58.97 | 5.76 5.69 | 5.76 5.48 |
| 770854 | " | " | " | " | " | 4-(CO-C₂H₅)-C₆H₄ | HCl | C₂₈H₃₇ClN₂O₇ + 9/4 H₂O | 589.58 | 114 | 45 | Cal. % Obt. % | 57.04 57.12 | 7.10 6.81 | 4.75 4.77 |
| 770963 | " | " | " | " | " | 2-methyl-4-nitrophenyl | HCl | C₂₆H₃₃N₃O₈ + 6/5 HCl + 3/5 H₂O | 570.11 | 155 | 53 | Cal. % Obt. % | 54.77 54.76 | 6.26 5.93 | 7.37 7.22 |
| 770966 | " | " | " | " | " | 4-chloro-2-methylphenyl | " | C₂₆H₃₄Cl₂N₂O₆ | 541.46 | 122 | 52 | Cal. % Obt. % | 57.67 57.63 | 6.33 6.26 | 5.17 4.90 |
| 770992 | " | " | " | " | " | 2,3-dimethoxy-4-methyl-(NH-CONH-CH₃)-phenyl | Base | C₂₉H₄₀N₄O₉ | 588.64 | 172 | 44 | Cal. % Obt. % | 59.17 58.91 | 6.85 6.55 | 9.52 9.35 |
| 771014 | " | " | " | " | " | 2-chloro-3,5-dimethylphenyl | HCl | C₂₇H₃₄Cl₂N₂O₆ | 552.46 | 191 | 70 | Cal. % Obt. % | 58.38 58.06 | 6.53 6.39 | 5.04 5.03 |

TABLE I-continued

Structure (I):

R—C₆H₄—C(=O)—CH=CH—N(piperazine with (CH₂)ₙ and R₁)—CH₂—X—(CH₂)ₘ—Aᵣ  (I)

| Code Number | n | R₁ | X | m | —Aᵣ | Form | Empirical Formula | Molecular weight | Melting point (°C.) | Yield % | | Elementary Analysis C | H | N |
|---|---|---|---|---|---|---|---|---|---|---|---|---|---|---|
| 771031 | " | " | " | " | 1-(NH—CONH—CH₃)-4-methylnaphthyl | Oxalate | $C_{33}H_{40}N_4O_{11}$ + 1/6 $H_2O$ | 671.685 | 204 | 67 | Cal. % Obt. % | 59.01 58.71 | 6.05 5.96 | 8.34 8.40 |
| 771036 | " | " | " | " | 1-(NH—COCH₃)-4-methylnaphthyl | HCl | $C_{31}H_{38}ClN_3O_7$ | 600.095 | 225 | 84 | Cal. % Obt. % | 62.04 61.93 | 6.38 6.09 | 7.00 7.11 |
| 771076 | " | " | " | " | 4-(CH₂—CONH₂)phenyl | Base | $C_{27}H_{36}N_3O_7$ + 2/3 $H_2O$ | 525.58 | 80 | 29 | Cal. % Obt. % | 61.70 62.25 | 6.96 7.05 | 7.80 7.87 |
| 771077 | " | " | " | " | 2-methyl-4-(NHCOCH₃)phenyl | " | $C_{28}H_{37}N_3O_7$ | 545.61 | 92 | 83 | Cal. % Obt. % | 61.63 61.94 | 7.21 7.01 | 7.70 7.70 |
| 771124 | " | " | " | " | 3-chloro-4-methyl-nitrophenyl | Base | $C_{25}H_{30}ClN_3O_8$ | 535.97 | 152 | 82 | Cal. % Obt. % | 56.02 55.71 | 5.64 5.71 | 7.84 7.53 |

TABLE I-continued

Structure formula:

$$\text{R} - \underset{\text{benzene ring}}{\bigcirc} - \text{CH}=\text{CH} - \text{C}(\text{O}) - \text{N} \underset{\text{piperazine}}{\bigcirc} \text{N} - \text{CH}_2 - \text{CH}(\text{R}_1) - (\text{CH}_2)_n - \text{X} - (\text{CH}_2)_m - \text{A}_r \quad (I)$$

| Code Number | n | R₁ | X | m | −Aᵣ | Form | Empirical Formula | Molecular weight | Melting point (°C.) | Yield % | Elementary Analysis C | H | N |
|---|---|---|---|---|---|---|---|---|---|---|---|---|---|
| 771149 | " | " | " | " | 8-methyl-benzodioxane with NH—CO—N(morpholino) | HCl | C₃₂H₄₃ClN₄O₁₀ + 2 H₂O | 715.185 | 182 | 98 | Cal. % 53.74  Obt. % 54.11 | 6.02  6.48 | 7.83  7.52 |
| 771153 | " | " | " | " | 7-methyl-indane with NH—CONH—CH₃ | " | C₃₀H₄₁ClN₄O₇ + 4/5 H₂O | 619.529 | 200 | 85 | Cal. % 58.16  Obt. % 57.95 | 6.93  6.86 | 9.04  9.33 |
| 771157 | " | " | " | " | 5-methyl-tetralin with NH—CONH—CH₃ | Oxalate | C₃₃H₄₄N₄O₁₁ + 2/5 H₂O | 679.920 | 200 | 76 | Cal. % 58.29  Obt. % 58.32 | 6.64  6.49 | 8.24  8.14 |
| 771233 | " | " | " | " | 8-methyl-benzodioxane with NH—CO—N(CH₃)₂ | Oxalate | C₃₂H₄₂N₄O₁₃ + 5/6 H₂O | 705.701 | 168 | 45 | Cal. % 54.46  Obt. % 54.55 | 6.24  5.93 | 7.94  7.72 |
| 771238 | " | " | " | " | 8-methyl-benzodioxane with N(CH₃)—CONH—CH₃ | HCl | C₃₀H₄₁ClN₄O₉ + 7/6 H₂O | 658.136 | 188 | 36 | Cal. % 54.75  Obt. % 54.74 | 6.64  6.55 | 8.51  8.21 |

TABLE I-continued

Structure (I):
R-C₆H₄-CH=CH-C(O)-N(piperazine with (CH₂)ₙ)-N-CH₂-CR₁H-X-(CH₂)ₘ-Ar

| Code Number | n | R₁ | X | m | −Ar | Form | Empirical Formula | Molecular weight | Melting point (°C.) | Yield % | ELEMENTARY ANALYSIS | | |
|---|---|---|---|---|---|---|---|---|---|---|---|---|---|
| | | | | | | | | | | | | C | H | N |
| 771281 | " | " | " | " | 3-methyl-5-cyano-phenyl (CN, OCH₃) | " | C₂₇H₃₄ClN₃O₇ + H₂O | 566.04 | 186 | 78 | Cal. % / Obt. % | 57.29 / 57.24 | 5.41 / 6.10 | 7.42 / 7.34 |
| 771306 | " | " | " | " | 4-methyl-7-(NHCOCH₃)-indane | " | C₃₀H₄₀ClN₃O₇ + 5/3 H₂O | 620.128 | 185 | 78 | Cal. % / Obt. % | 58.10 / 57.81 | 7.04 / 6.72 | 6.78 / 6.63 |
| 780044 | " | " | " | " | 8-methyl-5-OCOCH₃-benzodioxane | HCl | C₂₉H₃₇ClN₂O₁₀ + 4/6 H₂O | 630.078 | 205 | 28 | Cal. % / Obt. % | 55.28 / 55.35 | 6.13 / 5.95 | 4.45 / 4.44 |
| 780009 | " | " | " | " | 8-methyl-5-OCH₃-benzodioxane | " | C₂₈H₃₇ClN₂O₉ + 4/5 H₂O | 595.461 | 178 | 38 | Cal. % / Obt. % | 56.47 / 56.51 | 6.53 / 6.58 | 4.70 / 4.43 |
| 7800044 | " | " | " | " | 5-methyl-8-(NH-CO-CH₃)-tetralin | " | C₃₁H₄₂ClN₃O₇ + 3/2 H₂O | 631.151 | 185 | 56 | Cal. % / Obt. % | 58.99 / 59.19 | 7.19 / 6.81 | 6.66 / 6.66 |

TABLE I-continued
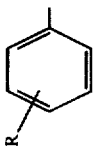
| Code Number | R | n | $R_1$ | X | m | $-A_r$ | Form | Empirical Formula | Molecular weight | Melting point (°C.) | Yield % | ELEMENTARY ANALYSIS C H N | | | |
|---|---|---|---|---|---|---|---|---|---|---|---|---|---|---|---|
| 780128 | " | " | " | " | " | 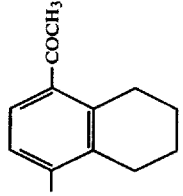 | " | $C_{31}H_{41}ClN_2O_7$ + 4/5 $H_2O$ | 603.523 | 150 | 60 | Cal. % Obt. % | 61.69 61.79 | 7.12 6.79 | 4.64 4.68 |
| 771309 | " | " | " | " | " | 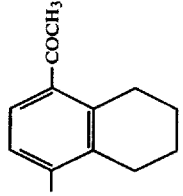 | Oxalate | $C_{30}H_{40}N_4O_{11}$ + 0.95 $H_2O$ | 649.77 | 184 | 48 | Cal. % Obt. % | 55.45 55.80 | 6.50 6.35 | 8.62 8.56 |
| 771315 | " | " | " | " | " | 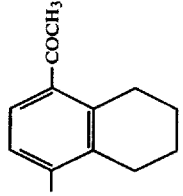 | HCl | $C_{31}H_{37}N_2O_7Cl$ + $H_2O$ | 603.095 | 210 | 30 | Cal. % Obt. % | 61.73 61.86 | 6.52 6.20 | 4.65 4.64 |
| 771318 | " | " | " | " | " | 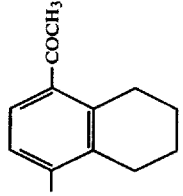 | Oxalate | $C_{32}H_{36}N_2O_7$ + 1.17(COOH)$_2$ | 665.97 | 170 | 23 | Cal. % Obt. % | 61.93 61.91 | 6.11 5.84 | 4.21 4.12 |
| 771348 | " | " | " | " | " | 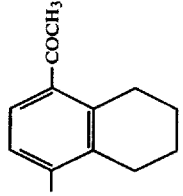 | " | $C_{30}H_{39}N_3O_{11}$ + 3/5 $H_2O$ | 628.45 | 180 | 51 | Cal. % Obt. % | 57.33 57.06 | 6.45 6.14 | 6.69 6.70 |

TABLE I-continued

| Code Number | R | n | R₁ | X | m | −Ar | Form | Empirical Formula | Molecular weight | Melting point (°C.) | Yield % | ELEMENTARY ANALYSIS C H N |
|---|---|---|---|---|---|---|---|---|---|---|---|---|
| 780138 | | " | " | " | " | (2,3-methylenedioxy-methylphenyl) | HCl | $C_{26}H_{33}ClN_2O_8$ | 536.998 | 199 | 30 | Cal. % 58.15 6.19 5.22<br>Obt. % 58.03 6.39 5.47 |
| 780150 | | " | " | " | " | (methylenedioxy-methylphenyl ethylenedioxy) | Oxalate | $C_{30}H_{38}N_2O_{12}$ | 618.62 | 212 | 71 | Cal. % 58.24 6.19 4.53<br>Obt. % 58.43 6.46 4.69 |
| 780189 | | " | " | " | " | NH—CONH—CH₃ (chloro-methylphenyl) | " | $C_{27}H_{35}ClN_4O_7$<br>+ 6/5(COOH)₂<br>+ 1/2 H₂O | 680.09 | 120 | 37 | Cal. % 51.92 5.64 8.23<br>Obt. % 51.34 5.58 8.08 |
| 780223 | | " | " | " | " | NH—CO—NH—(methoxyphenyl)(ethylenedioxy-methylphenyl) | HCl | $C_{35}H_{43}ClN_4O_{10}$<br>+ 0.6 H₂O | 725.992 | 155 | 30 | Cal. % 57.90 6.14 7.72<br>Obt. % 57.96 6.19 7.60 |
| 780225 | | " | " | " | " | NH—COCH₃ (ethylenedioxy-methylphenyl) | Oxalate | $C_{29}H_{37}N_3O_9$<br>+ 0.5(COOH)₂<br>+ H₂O | 634.654 | 154 | 40 | Cal. % 56.77 6.35 6.62<br>Obt. % 56.87 6.38 6.86 |

TABLE I-continued
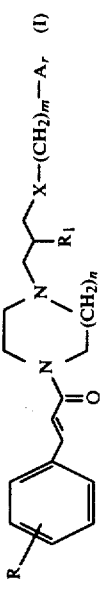
| Code Number | n | R₁ | X | m | −Ar | Form | Empirical Formula | Molecular weight | Melting point (°C.) | Yield % | ELEMENTARY ANALYSIS | | |
|---|---|---|---|---|---|---|---|---|---|---|---|---|---|
| | | | | | | | | | | | | C | H | N |
| 780241 | " | " | " | " | 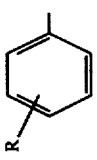 | HCl | $C_{30}H_{39}ClN_2O_9$ + $H_2O$ | 625.101 | 183 | 81 | Cal. % 57.64 6.61 4.48<br>Obt. % 57.90 6.50 4.35 |
| 780267 | " | " | " | " | −C₃H₇n (p-propylphenyl) | Base | $C_{28}H_{38}N_2O_6$ | 498.600 | 110 | 59 | Cal. % 67.44 7.68 5.62<br>Obt. % 67.17 7.77 5.78 |
| 780269 | 2 | " | " | " | 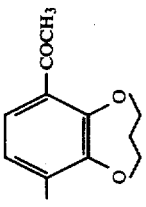 | HCl | $C_{29}H_{39}ClN_2O_8$ + 3/4 $H_2O$ | 592.59 | 106 | 46 | Cal. % 58.77 6.89 4.73<br>Obt. % 58.55 6.43 4.53 |
| 780272 | " | " | " | " | 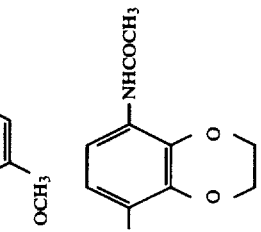 | Oxalate | $C_{32}H_{41}N_3O_{13}$ + 5/6 $H_2O$ | 690.686 | 130 | 30 | Cal. % 55.64 6.23 6.08<br>Obt. % 55.75 6.33 5.90 |
| 780292 | 1 | " | " | " | 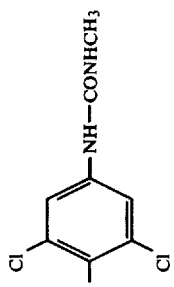 | " | $C_{29}H_{36}Cl_2N_4O_{11}$ | 687.52 | 200 | 30 | Cal. % 50.66 5.28 8.15<br>Obt. % 50.38 5.49 8.18 |

TABLE I-continued

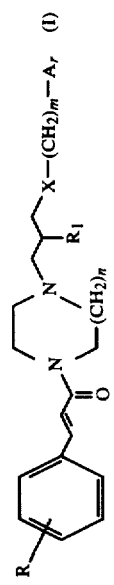

| Code Number | R | n | $R_1$ | X | m | -Ar | Form | Empirical Formula | Molecular weight | Melting point (°C.) | Yield % | Elementary Analysis C H N | | | |
|---|---|---|---|---|---|---|---|---|---|---|---|---|---|---|---|
| 780301 | " | " | " | " | " | 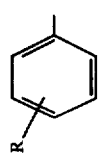COOC₅H₁₁n (benzo-dioxane) | " | C₃₅H₄₆N₂O₁₄ | 718.734 | 146 | 93 | Cal. % Obt. % | 58.48 58.58 | 6.45 6.48 | 3.90 3.92 |
| 780302 | " | " | " | " | " | COC₃H₇n (phenyl) | HCl | C₂₉H₃₉ClN₂O₇ | 563.17 | 158 | 19 | Cal. % Obt. % | 61.84 61.56 | 6.98 6.95 | 4.97 5.11 |
| 780346 | " | " | " | " | " | NH—COCH₃ (benzodioxole) | HCl | C₂₈H₃₆ClN₃O₉ + 3/5 H₂O | 604.858 | 168 | 43 | Cal. % Obt. % | 55.60 55.82 | 6.20 6.21 | 6.95 7.12 |
| 780353 | " | " | " | " | " | COCH₃ (F-phenyl) | Oxalate | C₂₉H₃₅FN₂O₁₁ + 3/5 H₂O | 617.39 | 125 | 33 | Cal. % Obt. % | 56.41 56.33 | 5.91 5.79 | 4.54 4.76 |
| 780357 | " | " | " | " | " | NH—CONH—CH₃ (3,5-di-OCH₃ phenyl) | " | C₃₁H₄₂N₄O₁₃ | 678.68 | 125 | 12 | Cal. % Obt. % | 54.85 55.06 | 6.24 6.55 | 8.26 8.25 |

TABLE I-continued

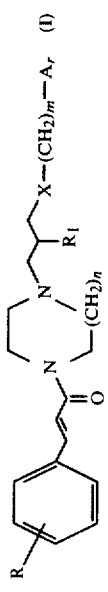

| Code Number | n | R₁ | X | m | —Ar | Form | Empirical Formula | Molecular weight | Melting point (°C.) | Yield % | ELEMENTARY ANALYSIS | | |
|---|---|---|---|---|---|---|---|---|---|---|---|---|---|
| | | | | | | | | | | | | C | H | N |
| 780359 | " | " | " | " | 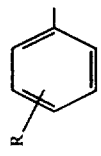 (3,5-di-OCH₃, 4-CH₃, COCH₃) | " | C₃₁H₄₀N₂O₁₃ + 1/5 H₂O | 652.25 | 188 | 34 | Cal. % 57.08 6.24 4.29 Obt. % 56.94 6.13 4.21 |
| 780308 | " | " | " | " | (4-COCH₃ benzodioxole, CH₃) | HCl | C₂₈H₃₅ClN₂O₉ + 0.33 H₂O | 585.038 | 192 | 70 | Cal. % 57.48 6.15 4.79 Obt. % 57.53 6.32 4.64 |
| 780329 | " | " | " | " | (CHO, OCH₃, CH₃) | Base | C₂₇H₃₄N₂O₈ | 514.55 | 135 | 21 | Cal. % 63.02 6.66 5.44 Obt. % 62.70 6.85 5.51 |
| 780333 | " | " | " | " | (cyclohexyl-OOC-benzodioxane-CH₃) | Oxalate | C₃₆H₄₆N₂O₁₄ + 1/2 H₂O | 739.752 | 172 | 97 | Cal. % 58.45 6.40 3.79 Obt. % 58.41 6.35 3.89 |
| 780339 | " | " | " | " | (3,5-di-Cl, 4-CH₃, COCH₃) | " | C₂₉H₃₄Cl₂N₂O₁₁ | 657.49 | 175 | 39 | Cal. % 52.97 4.91 4.26 Obt. % 53.06 4.85 4.12 |

TABLE I-continued

| Code Number | n | $R_1$ | X | m | $-A_r$ | Form | Empirical Formula | Molecular weight | Melting point (°C.) | Yield % | ELEMENTARY ANALYSIS C H N |
|---|---|---|---|---|---|---|---|---|---|---|---|
| 780361 | " | " | " | " | (3,5-dimethoxy-4-methylphenyl, COOEt) | Oxalate | $C_{32}H_{42}N_2O_{14}$ + $H_2O$ | 696.69 | 200 | 40 | Cal. % 55.16 6.37 4.02<br>Obt. % 55.45 6.15 3.71 |
| 780369 | " | " | " | " | (benzodioxane, COO-tBu) | HCl | $C_{32}H_{43}ClN_2O_{10}$ + $H_2O$ | 675.158 | 195 | 90 | Cal. % 56.92 6.82 4.15<br>Obt. % 56.64 6.50 3.84 |
| 780373 | " | " | " | " | (benzodioxane, COO-iPr) | Oxalate | $C_{33}H_{42}N_2O_{14}$ + 0.9 $H_2O$ | 706.896 | 130 | 80 | Cal. % 56.07 6.24 3.96<br>Obt. % 56.35 5.91 3.95 |
| 780374 | 2 | " | " | " | (benzodioxane, NH-CONH-CH$_3$) | HCl | $C_{30}H_{41}ClN_4O_9$ + 1.9 $H_2O$ | 671.347 | 185 | 65 | Cal. % 53.67 6.73 8.35<br>Obt. % 53.43 6.52 8.30 |
| 780384 | 1 | " | Sulfur | " | (benzodioxane, COCH$_3$) | HCl | $C_{29}H_{37}ClN_2O_8S$ + 3/5 $H_2O$ | 619.934 | 192 | 73 | Cal. % 56.18 6.21 4.52<br>Obt. % 56.45 6.10 4.52 |

TABLE I-continued

Structure (I): R-C₆H₄-C(=O)-CH=CH-N[piperazine with (CH₂)ₙ]-CH(R₁)-CH₂-X-(CH₂)ₘ-Ar

| Code Number | n | R₁ | X | m | –Ar | Form | Empirical Formula | Molecular weight | Melting point (°C.) | Yield % | ELEMENTARY ANALYSIS C / H / N |
|---|---|---|---|---|---|---|---|---|---|---|---|
| 780389 | " | " | " | " | 2,3-dihydro-1,4-benzodioxin-methyl | " | C₂₇H₃₅ClN₂O₇S | 567.089 | 171 | 50 | Cal. % 57.18 6.22 4.94 / Obt. % 56.96 6.55 4.90 |
| 780393 | " | " | Oxygen | " | methylbenzodioxole-NH–COCH₃ | " | C₃₀H₄₀ClN₃O₉ + 2/5 H₂O | 629.307 | 180 | 94 | Cal. % 57.25 6.53 6.68 / Obt. % 56.96 6.23 6.41 |
| 780401 | " | " | " | " | Cl-methylphenyl-COCH₃ | Oxalate | C₂₉H₃₅ClN₂O₁₁ | 623.04 | 135 | 42 | Cal. % 55.90 5.66 4.50 / Obt. % 55.77 5.69 4.53 |
| 780409 | " | " | " | " | methylbenzodioxole-NH–CONH–CH₃ | HCl | C₂₈H₃₇ClN₄O₉ + H₂O | 627.081 | 156 | 62 | Cal. % 53.62 6.11 8.94 / Obt. % 53.67 6.19 9.04 |
| 780411 | " | " | " | " | cyclohexyl-methylphenyl | Oxalate | C₃₃H₄₄N₂O₁₀ | 628.698 | 194 | 43 | Cal. % 63.04 7.05 4.46 / Obt. % 62.78 7.09 4.76 |
| 780415 | 2 | " | " | " | methylphenyl-COCH₃ | HCl | C₂₈H₃₇ClN₄O₇ | 549.05 | 232 | 52 | Cal. % 61.25 6.79 5.10 / Obt. % 61.28 6.58 4.83 |

TABLE I-continued

| Code Number | R | n | $R_1$ | X | m | $-A_r$ | Form | Empirical Formula | Molecular weight | Melting point (°C.) | Yield % | ELEMENTARY ANALYSIS C H N | | |
|---|---|---|---|---|---|---|---|---|---|---|---|---|---|---|
| 780448 | " | 1 | " | " | " | 4-CO-C$_2$H$_5$, 3-OCH$_3$ phenyl | Oxalate | C$_{31}$H$_{46}$N$_2$O$_{12}$ | 632.65 | 165 | 64 | Cal. % 58.85 6.37 4.43 Obt. % 58.63 6.29 4.32 | | |
| 780452 | " | " | " | " | " | 6-methyl-tetralone | Oxalate | C$_{30}$H$_{37}$N$_2$O$_9$ | 569.61 | 185 | 56 | Cal. % 63.25 6.54 4.92 Obt. % 63.10 6.76 5.01 | | |
| 780455 | " | " | " | S | " | 4-COCH$_3$ phenyl | " | C$_{29}$H$_{36}$N$_2$O$_{10}$S + H$_2$O | 622.68 | 152 | 56 | Cal. % 55.93 6.15 4.50 Obt. % 56.08 5.98 4.71 | | |
| 780456 | " | " | " | Oxygen | " | NH—CONH—CH$_3$ methylenedioxyphenyl | HCl | C$_{30}$H$_{41}$ClN$_4$O$_9$ + 2 H$_2$O | 673.149 | 177 | 85 | Cal. % 53.52 6.74 8.32 Obt. % 53.57 6.28 8.11 | | |
| 780474 | " | " | " | S | " | 4-COCH$_3$, 3-OCH$_3$ phenyl | Oxalate | C$_{30}$H$_{38}$N$_2$O$_{11}$S + 3/5 H$_2$O | 645.49 | 157 | 22 | Cal. % 55.82 6.12 4.34 Obt. % 56.10 6.36 4.66 | | |
| 760382 | " | " | " | Oxygen | " | 4-COO-C$_2$H$_5$ phenyl | HCl | C$_{28}$H$_{37}$ClN$_2$O$_8$ | 565.05 | 170 | 63 | Cal. % 59.51 6.60 4.96 Obt. % 59.77 6.66 5.09 | | |

TABLE I-continued $$\text{R}-\text{C}_6\text{H}_4-\text{CH}=\text{CH}-\text{C(O)}-\text{N(piperazine)}-\text{CH}_2-\text{CR}_1\text{H}-(\text{CH}_2)_n-\text{X}-(\text{CH}_2)_m-A_r \quad (I)$$

| Code Number | R | n | R₁ | X | m | —Aᵣ | Form | Empirical Formula | Molecular weight | Melting point (°C.) | Yield % | | Elementary Analysis C | H | N |
|---|---|---|---|---|---|---|---|---|---|---|---|---|---|---|---|
| 760385 | | " | " | " | " | 4-CH₃-C₆H₄-COCH₃ | HCl | C₂₇H₃₅ClN₄O₇ + 2 H₂O | 571.05 | 130 | 59 | Cal. % Obt. % | 56.78 56.76 | 6.88 6.68 | 4.91 4.96 |
| 760389 | | " | " | " | " | 2-CN-C₆H₄- | HCl | C₂₆H₃₃ClN₃O₆ + 1/2 H₂O | 528.01 | 130 | 64 | Cal. % Obt. % | 59.14 59.29 | 6.49 6.49 | 7.96 8.18 |
| 760390 | | " | " | " | " | 3-OCH₃-C₆H₄- | HCl | C₂₆H₃₅ClN₂O₇ + 3/4 H₂O | 536.55 | 163 | 70 | Cal. % Obt. % | 58.25 58.15 | 6.73 6.60 | 5.22 5.03 |
| 760392 | | " | " | " | " | 2-OCH₃-C₆H₄- | HCl | C₂₆H₃₅ClN₂O₇ + H₂O | 541.03 | 197 | 45 | Cal. % Obt. % | 57.72 57.79 | 6.89 6.68 | 5.18 4.92 |
| 760393 | | " | " | " | " | 2,6-(OCH₃)₂-C₆H₃- | " | C₂₇H₃₇ClN₂O₈ + H₂O | 571.05 | 120 | 77 | Cal. % Obt. % | 56.78 56.80 | 6.88 6.93 | 4.90 4.86 |
| 760394 | | " | " | " | " | (benzodioxane-COCH₃) | Oxalate | C₃₁H₃₈N₂O₁₃ + 1/3 H₂O | 652.63 | 195 | 47 | Cal. % Obt. % | 57.05 57.13 | 5.97 5.85 | 4.29 4.24 |

TABLE I-continued

Structure (I):
$$\text{R—C}_6\text{H}_4\text{—CH=CH—C(O)—N(piperazine)—CH}_2\text{—CR}_1\text{H—X—(CH}_2)_m\text{—A}_r \quad (I)$$

with $(CH_2)_n$ on piperazine.

| Code Number | R | n | R$_1$ | X | m | —A$_r$ | Form | Empirical Formula | Molecular weight | Melting point (°C.) | Yield % | ELEMENTARY ANALYSIS C | H | N |
|---|---|---|---|---|---|---|---|---|---|---|---|---|---|---|
| 760455 | " | " | " | " | " | 2-COCH$_3$-C$_6$H$_4$ | HCl | C$_{27}$H$_{35}$ClN$_2$O$_7$ + H$_2$O | 554.03 | 117 | 74 | Cal. % 58.53  Obt. % 58.33 | 6.91  6.30 | 5.06  5.23 |
| 760476 | " | " | " | " | " | 4-Cl-C$_6$H$_4$ | HCl | C$_{25}$H$_{32}$Cl$_2$N$_2$O$_6$ | 527.44 | 158 | 77 | Cal. % 56.93  Obt. % 56.80 | 6.12  6.30 | 5.31  5.16 |
| 760501 | " | " | " | " | " | 4-CN-C$_6$H$_4$ | Base | C$_{26}$H$_{31}$N$_3$O$_6$ | 481.53 | 137 | 50 | Cal. % 64.85  Obt. % 64.62 | 6.49  6.52 | 8.73  8.61 |
| 760506 | " | " | " | " | " | 3,4,5-(OCH$_3$)$_3$-C$_6$H$_2$ | HCl | C$_{28}$H$_{39}$ClN$_2$O$_9$ + 1/2 H$_2$O | 592.07 | 215 | 55 | Cal. % 56.80  Obt. % 56.71 | 6.81  6.53 | 4.73  4.97 |
| 760507 | " | " | " | " | " | 4-SCH$_3$-C$_6$H$_4$ | HCl | C$_{26}$H$_{35}$ClN$_2$O$_6$S + 1/4 H$_2$O | 543.58 | 195 | 51 | Cal. % 57.44  Obt. % 57.44 | 6.58  6.52 | 5.15  5.44 |
| 760519 | " | " | " | " | " | benzo-1,4-dioxan-yl | HCl | C$_{27}$H$_{35}$ClN$_2$O$_8$ + H$_2$O | 569.04 | 190 | 80 | Cal. % 56.89  Obt. % 57.34 | 6.55  6.62 | 4.92  4.80 |

TABLE I-continued

Structure:

$$\text{R}-\bigcirc-\overset{\text{O}}{\underset{\|}{\text{C}}}-\text{CH=CH}-\text{N}\underset{(CH_2)_n}{\overset{(CH_2)_n}{\diagdown}}\text{N}-\overset{R_1}{\underset{|}{\text{CH}_2}}-\text{X}-(CH_2)_m-A_r \quad (I)$$

| Code Number | R | n | $R_1$ | X | m | $-A_r$ | Form | Empirical Formula | Molecular weight | Melting point (°C.) | Yield % | Elementary Analysis | C | H | N |
|---|---|---|---|---|---|---|---|---|---|---|---|---|---|---|---|
| 760520 | " | " | " | " | " | 2-Cl-phenyl | HCl | $C_{25}H_{32}Cl_2N_2O_6$ + $H_2O$ | 545.45 | 152 | 48 | Cal. % / Obt. % | 55.05 / 54.90 | 6.28 / 6.29 | 5.14 / 4.95 |
| 760529 | " | " | " | " | " | benzo[1,3]dioxole | HCl | $C_{26}H_{33}ClN_2O_8$ + 1/3 $H_2O$ | 536.99 | 178 | 25 | Cal. % / Obt. % | 57.51 / 57.53 | 6.25 / 6.51 | 5.16 / 5.15 |
| 760538 | " | " | " | " | " | 4-$NO_2$-phenyl | HCl | $C_{25}H_{32}ClN_3O_8$ + 2/5 $H_2O$ | 545.19 | 195 | 40 | Cal. % / Obt. % | 55.07 / 54.72 | 6.06 / 5.95 | 7.71 / 7.59 |
| 760542 | " | " | " | " | " | 4-(NH—COCH$_3$)-phenyl | Base | $C_{27}H_{35}N_3O_7$ + 2 $H_2O$ | 549.61 | 115 | 31 | Cal. % / Obt. % | 59.00 / 59.03 | 7.15 / 6.64 | 7.65 / 7.68 |
| 760580 | " | " | " | " | " | 2,6-di-OCH$_3$-3-CH$_3$-phenyl | HCl | $C_{27}H_{37}ClN_2O_8$ + 1/2 $H_2O$ | 562.05 | 190 | 76 | Cal. % / Obt. % | 57.69 / 57.74 | 6.82 / 6.69 | 4.97 / 4.96 |
| 760619 | " | " | " | " | " | 2-F-phenyl | HCl | $C_{24}H_{32}ClFN_2O_6$ + 1/2 $H_2O$ | 519.99 | 197 | 67 | Cal. % / Obt. % | 57.74 / 58.00 | 6.40 / 6.38 | 5.39 / 5.09 |
| 760620 | " | " | " | " | " | 3,5-di-OCH$_3$-phenyl | HCl | $C_{25}H_{37}ClN_2O_8$ + 4/5 $H_2O$ | 567.45 | 184 | 85 | Cal. % / Obt. % | 57.15 / 57.37 | 6.86 / 6.75 | 4.94 / 5.03 |

TABLE 1-continued

Structure (I):

$$R\text{—}C_6H_4\text{—}CH\!=\!CH\text{—}C(\!=\!O)\text{—}N\big(\text{piperazine}(CH_2)_n\big)\text{—}CH(R_1)\text{—}CH_2\text{—}X\text{—}(CH_2)_m\text{—}A_r \quad (I)$$

| Code Number | R | n | $R_1$ | X | m | $-A_r$ | Form | Empirical Formula | Molecular weight | Melting point (°C.) | Yield % | Elementary Analysis |  |  |  |
|---|---|---|---|---|---|---|---|---|---|---|---|---|---|---|---|
|  |  |  |  |  |  |  |  |  |  |  |  |  | C | H | N |
| 760700 | OCH₃, CH₃O, OCH₃ | 1 | OH | Oxygen | 0 | benzodioxane-COO—C₂H₅ | HCl | C₃₀H₃₉ClN₂O₁₀ + H₂O | 641.10 | 175 | 62.5 | Cal. % Obt. % | 56.20 56.26 | 6.45 6.37 | 4.37 4.29 |
| 760705 | " | " | " | " | " | benzodioxane-CH₂—OH | Base | C₂₈H₃₆N₂O₉ | 544.58 | 100 | 12 | Cal. % Obt. % | 61.75 61.44 | 6.66 6.57 | 5.14 4.84 |
| 760710 | " | " | " | " | " | benzodioxane-CONH—CH₃ | Oxalate | C₃₁H₃₉N₃O₁₃ + 5/4 H₂O | 684.17 | 160 | 37 | Cal. % Obt. % | 54.42 54.65 | 6.11 6.00 | 6.14 6.10 |
| 760781 | " | " | " | " | " | phenyl-OCH₃, OCH₃, OCH₃, COCH₃ | HCl | C₃₀H₄₁ClN₂O₁₀ + 4/3 H₂O | 649.12 | 138 | 62 | Cal. % Obt. % | 55.91 55.10 | 6.78 6.45 | 4.32 4.40 |
| 760784 | " | " | " | " | " | phenyl-CN | HCl | C₂₆H₃₃ClN₃O₆ + 1/2 H₂O | 528.01 | 130 | 64 | Cal. % Obt. % | 59.14 59.29 | 6.49 6.49 | 7.96 8.18 |

TABLE I-continued

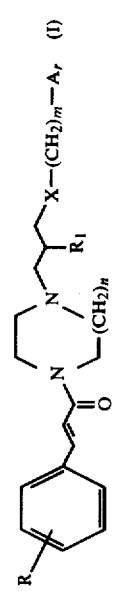

| Code Number |  | n | R$_1$ | X | m | —A$_r$ | Form | Empirical Formula | Molecular weight | Melting point (°C.) | Yield % | | ELEMENTARY ANALYSIS | | |
|---|---|---|---|---|---|---|---|---|---|---|---|---|---|---|---|
| | | | | | | | | | | | | | C | H | N |
| 760847 | " | " | " | " | " |  | Oxalate | C$_{30}$H$_{38}$N$_2$O$_{12}$ + 2/5 H$_2$O | 625.83 | 148 | 72 | Cal. % | 57.57 | 6.25 | 4.48 |
| | | | | | | | | | | | | Obt. % | 57.55 | 6.04 | 4.46 |
| 760852 | " | " | " | " | " |  | HCl | C$_{30}$H$_{39}$ClN$_2$O$_7$ + 3/4 H$_2$O | 588.59 | 130 | 43 | Cal. % | 61.12 | 6.72 | 4.72 |
| | | | | | | | | | | | | Obt. % | 61.21 | 6.94 | 4.76 |
| 760866 | " | " | " | " | " |  | " | C$_{31}$H$_{41}$ClN$_2$O$_9$ + H$_2$O | 640.93 | 142 | 49 | Cal. % | 58.09 | 6.78 | 4.37 |
| | | | | | | | | | | | | Obt. % | 57.91 | 6.72 | 4.17 |
| 760868 | " | " | " | " | " | NH—COCH$_3$ (dioxane-methyl) | Oxalate | C$_{31}$H$_{39}$N$_3$O$_{13}$ + 3/2 H$_2$O | 724.28 | 136 | 70 | Cal. % | 53.03 | 5.84 | 5.80 |
| | | | | | | | | | | | | Obt. % | 53.10 | 5.75 | 5.94 |
| 760892 | " | " | " | " | " | NH—COC$_3$H$_{7n}$ (tolyl) | Base | C$_{29}$H$_{39}$N$_3$O$_7$ + 2/3 H$_2$O | 553.64 | 108 | 40 | Cal. % | 62.91 | 7.34 | 7.59 |
| | | | | | | | | | | | | Obt. % | 62.99 | 7.28 | 7.53 |

TABLE I-continued

Structural formula (I):

R—(phenyl)—CH=CH—C(=O)—N(piperazine ring with (CH$_2$)$_n$)—CH(R$_1$)—CH$_2$—X—(CH$_2$)$_m$—A$_r$

| Code Number | R | n | R$_1$ | X | m | —A$_r$ | Form | Empirical Formula | Molecular weight | Melting point (°C.) | Yield % | | ELEMENTARY ANALYSIS | | |
|---|---|---|---|---|---|---|---|---|---|---|---|---|---|---|---|
| | | | | | | | | | | | | | C | H | N |
| 760986 | " | " | " | " | " | 5-methyl-tetralone | HCl | C$_{29}$H$_{37}$ClN$_2$O$_7$ + 4/5 H$_2$O | 575.47 | 168 | 11 | Cal. % | 60.52 | 6.76 | 4.87 |
| | | | | | | | | | | | | Obt. % | 60.38 | 6.61 | 4.86 |
| 770056 | " | " | " | " | " | 4-(NH—CO—NH—CH$_3$)phenyl | Base | C$_{27}$H$_{36}$N$_4$O$_7$ | 528.59 | >200 | 12 | Cal. % | 61.35 | 6.86 | 10.60 |
| | | | | | | | | | | | | Obt. % | 61.06 | 7.00 | 10.25 |
| 770058 | " | " | " | " | " | 4-CONH$_2$-phenyl | HCl | C$_{26}$H$_{34}$ClN$_3$O$_7$ + 1/2 H$_2$O | 545.02 | 143 | 48 | Cal. % | 57.29 | 6.47 | 7.71 |
| | | | | | | | | | | | | Obt. % | 57.23 | 6.36 | 7.49 |
| 770059 | " | " | " | S | " | 4-CH$_3$-phenyl | " | C$_{26}$H$_{35}$ClN$_2$O$_5$S | 523.08 | 200 | 55 | Cal. % | 59.70 | 6.74 | 5.36 |
| | | | | | | | | | | | | Obt. % | 59.61 | 6.82 | 5.34 |
| 770060 | " | " | " | " | " | phenyl | " | C$_{25}$H$_{33}$ClN$_2$O$_5$S | 509.05 | 154 | 56 | Cal. % | 58.98 | 6.53 | 5.50 |
| | | | | | | | | | | | | Obt. % | 58.68 | 6.55 | 5.59 |
| 770073 | " | " | " | Oxygen | " | 3-COCH$_3$-4-OCH$_3$-phenyl | Oxalate | C$_{30}$H$_{38}$N$_2$O$_{12}$ + 1/3 H$_2$O | 625.83 | 155 | 65 | Cal. % | 57.68 | 6.24 | 4.49 |
| | | | | | | | | | | | | Obt. % | 57.60 | 6.17 | 4.30 |

TABLE I-continued

Structure (I):
$$R-C_6H_4-C(=O)-N(\text{piperazine ring with }(CH_2)_n)-CH(R_1)-X-(CH_2)_m-A_r \quad (I)$$

| Code Number | R | n | $R_1$ | X | m | $-A_r$ | Form | Empirical Formula | Molecular weight | Melting point (°C.) | Yield % | ELEMENTARY ANALYSIS | | |
|---|---|---|---|---|---|---|---|---|---|---|---|---|---|---|
| | | | | | | | | | | | | | C | H | N |
| 770077 | | " | " | " | " | 2,3-dihydro-1,4-benzodioxin-5-yl-NH—CONH—CH₃ | Base | $C_{29}H_{38}N_4O_9$ + 1/2 $H_2O$ | 595.63 | 155 | 50 | Cal. % 58.47 6.60 9.41<br>Obt. % 58.45 6.48 9.27 |
| 770081 | " | " | " | " | " | 2,3-dihydro-1,4-benzodioxin-5-yl-NH—CONH—cyclohexyl | HCl | $C_{34}H_{47}ClN_4O_9$ + 3/4 $H_2O$ | 704.72 | 168 | 42 | Cal. % 57.94 6.94 7.95<br>Obt. % 57.90 6.85 7.91 |
| 770085 | " | " | " | " | " | 2,3-dihydro-1,4-benzodioxin-5-yl-NH—CO—NH—phenyl | " | $C_{34}H_{41}ClN_4O_9$ + 4/5 $H_2O$ | 699.57 | 168 | 32 | Cal. % 58.37 6.14 8.01<br>Obt. % 58.54 5.89 8.13 |
| 770112 | " | " | " | S | " | 3-methoxyphenyl ($OCH_3$) | " | $C_{25}H_{35}ClN_2O_6S$ | 539.08 | 152 | 83 | Cal. % 57.92 6.54 5.20<br>Obt. % 57.68 6.38 5.08 |
| 770135 | " | " | " | Oxygen | " | 4-(CONH—CH₃)-phenyl | Base | $C_{27}H_{35}N_3O_7$ + 4/5 $H_2O$ | 527.99 | 130 | 56 | Cal. % 61.42 6.99 7.96<br>Obt. % 61.39 6.91 8.02 |

TABLE I-continued

Structure (I):

$$\text{R-C}_6\text{H}_4\text{-C(=O)-CH=... -N(piperazine)-N-CH}_2\text{-CH(R}_1\text{)-(CH}_2)_n\text{... X-(CH}_2)_m\text{-A}_r \quad (I)$$

| Code Number | n | R₁ | X | m | —Aᵣ | Form | Empirical Formula | Molecular weight | Melting point (°C.) | Yield % | | ELEMENTARY ANALYSIS C H N |
|---|---|---|---|---|---|---|---|---|---|---|---|---|
| 770142 | " | " | " | " | 2,3-dihydro-1,4-benzodioxin-5-yl, 8-C₂H₅ | Oxalate | C₃₁H₄₀N₂O₁₂ | 632.65 | 200 | 47 | Cal. % Obt. % | 58.85  6.37  4.43 / 58.94  6.35  4.55 |
| 770188 | " | " | " | " | 2,3-dihydro-1,4-benzodioxin-5-yl, 8-CH₂—CN | HCl | C₂₉H₃₆ClN₃O₈ | 590.05 | 140 | 52 | Cal. % Obt. % | 59.03  6.15  7.12 / 59.12  5.83  6.99 |
| 760939 | " | H | " | " | 2,3-dihydro-1,4-benzodioxin-5-yl, 8-COCH₃ | Base | C₂₉H₃₆N₂O₈ | 540.59 | 134 | 18.5 | Cal. % Obt. % | 64.43  6.71  5.18 / 64.10  6.77  5.00 |
| 771163 | " | H | " | " | 2,3-dihydro-1,4-benzodioxin-5-yl, 8-CONH—CH₃ | Oxalate | C₃₁H₃₉N₃O₁₂ + 1/2 H₂O | 654.654 | 211 | 50 | Cal. % Obt. % | 56.87  6.16  6.42 / 57.07  6.13  6.34 |
| 771172 | " | " | " | " | 2,3-dihydro-1,4-benzodioxin-5-yl, 8-NH—COCH₃ | " | C₃₁H₃₉N₃O₁₂ | 645.646 | 195 | 83 | Cal. % Obt. % | 57.66  6.09  6.51 / 57.35  6.12  6.64 |

TABLE I-continued

| Code Number | R | n | R₁ | X | m | -Ar | Form | Empirical Formula | Molecular weight | Melting point (°C.) | Yield % | ELEMENTARY ANALYSIS C H N |
|---|---|---|---|---|---|---|---|---|---|---|---|---|
| 780040 | (3,5-diOCH₃-phenyl) | " | " | " | " | (benzodioxane-NH-CONH-CH₃) | HCl | $C_{29}H_{39}ClN_4O_8$ + 7/4 $H_2O$ | 638.619 | 145 | 60 | Cal. % 54.53 6.70 8.77<br>Obt. % 54.24 6.36 8.66 |
| 780404 | (3,5-diOCH₃-phenyl) | " | OH | " | " | (3-OCH₃-4-CH₃-phenyl COCH₃) | Base | $C_{27}H_{34}N_2O_7$ + 3/5 $H_2O$ | 509.37 | 60 | 71 | Cal. % 63.66 6.97 5.50<br>Obt. % 63.70 6.96 5.83 |
| 760388 | (2,3,4-triOCH₃-phenyl) | 2 | " | " | " | (phenyl) | HCl | $C_{26}H_{35}ClN_2O_6$ | 507.01 | 175 | 20 | Cal. % 61.59 6.95 5.53<br>Obt. % 61.09 7.07 5.74 |
| 760502 | " | 1 | " | " | " | (2-CH₃-phenyl) | " | $C_{26}H_{35}ClN_2O_6$ + 3/4 $H_2O$ | 520.52 | 150 | 78 | Cal. % 59.99 6.87 5.38<br>Obt. % 60.32 7.12 5.50 |
| 760503 | " | " | " | " | " | (2-(O-allyl)-phenyl) | " | $C_{29}H_{37}ClN_2O_7$ + 1/2 $H_2O$ | 588.06 | 138 | 65 | Cal. % 60.26 6.88 5.02<br>Obt. % 60.56 6.86 5.00 |

TABLE I-continued $$\text{[structure: R-phenyl-CH=CH-C(O)-N-piperazine-N-CH}_2\text{-CHR}_1\text{-(CH}_2)_n\text{-X-(CH}_2)_m\text{-Ar]} \quad (I)$$

| Code Number | R | n | R₁ | X | m | —Ar | Form | Empirical Formula | Molecular weight | Melting point (°C.) | Yield % | ELEMENTARY ANALYSIS C H N |
|---|---|---|---|---|---|---|---|---|---|---|---|---|
| 760504 | | " | " | " | " | 3-Cl-phenyl | " | C₂₅H₃₂Cl₂N₂O₆ + 2/3 H₂O | 539.45 | 160 | 67 | Cal. % 55.66 6.23 5.19<br>Obt. % 55.40 6.33 5.25 |
| 760505 | | " | " | " | " | 4-CH₃-phenyl | HCl | C₂₆H₃₅ClN₂O₆ + H₂O | 525.03 | 180 | 81 | Cal. % 59.47 7.10 5.34<br>Obt. % 59.70 7.00 5.24 |
| 760518 | | " | " | " | " | 2-CH₃-phenyl (with CH₂) | " | C₂₈H₃₇ClN₂O₆ + 1/2 H₂O | 542.06 | 163 | 85 | Cal. % 62.04 7.07 5.17<br>Obt. % 62.13 7.35 5.02 |
| 760521 | | " | " | " | " | 3-CH₃-phenyl | " | C₂₆H₃₅ClN₂O₆ + H₂O | 525.03 | 184 | 78 | Cal. % 59.47 7.10 5.34<br>Obt. % 59.55 6.74 5.08 |

EXAMPLE 2

1-[3-(4-acetyl-2,3-ethylenedioxy)phenoxy-2-hydroxy]-propyl-4-(3,5-dimethoxy-4-hydroxycinnamoyl)piperazine oxalate (I)

Code number: 770 274

A mixture of 9.6 g (0.0155 mole) of 1-[3-(4-acetyl-2,3-ethylenedioxy)phenoxy-2-hydroxy]propyl-4-(3,5-dimethoxy-4-acetoxy cinnamoyl)piperazine (Ib) (used in the crude state) and of 3.9 g (0.0465 mole) of sodium bicarbonate in 60 cm$^3$ of ethanol was brought to reflux for 5 hours. Then, the solvent was evaporated, the residue was taken up in acetone and a solution of 1.4 g (0.0155 mole) of oxalic acid in acetone was added. After filtering 6.3 g of product were obtained.
Yield: 65%
Melting point: 110° C.
Empirical formula: $C_{30}H_{36}N_2O_{13} + \frac{3}{4} H_2O$
Molecular weight: 646.12

Elementary Analysis:

|  | C | H | N |
|---|---|---|---|
| Calculated % | 55.76 | 5.85 | 4.34 |
| Obtained % | 55.81 | 5.74 | 4.07 |

By the same process, but from the compound of formula (Ib)

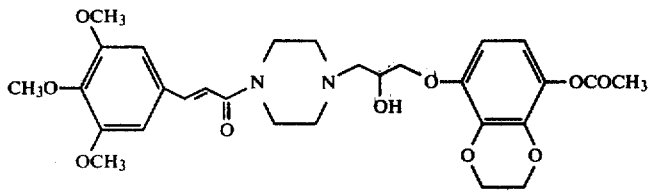

(Ib)

Code No. 780 004, 1-[3-(4-hydroxy-2,3-ethylenedioxy)phenoxy-2-hydroxy]propyl-4-(3,4,5-trimethoxy-cinnamoyl)piperazine, hydrated chlorhydrate was obtained.
Code Number: 780 120
Yield: 22%
Melting Point: 174° C.
Empirical formula: $C_{27}H_{37}ClN_2O_{10}$
Molecular weight: 585.04

Elementary analysis:

|  | C | H | N |
|---|---|---|---|
| Calculated % | 55.43 | 6.37 | 4.79 |
| Obtained % | 55.25 | 6.22 | 5.00 |

EXAMPLE 3

1-[3-(4-acetyl-2,3-ethylenedioxy)phenoxy]-propyl-4-(3,4,5-trimethoxycinnamoyl)piperazine (I)

Code number: 760 939

1st step: 3-(4-acetyl-2,3-ethylenedioxy)phenoxy-1-chloropropane (XXVIII)

This compound was obtained following the same working method as 3-(4-acetamido-2,3-ethylenedioxy)phenoxy-1-chloropropane of code number 771 171 for which:

A mixture of 25 g of 5-acetamido-8-hydroxy-benzodioxan, of 50 g of potassium carbonate and of 35.5 ml of 1-bromo-1-chloropropane in 500 ml of acetonitrile was brought to reflux for three hours. After filtering, evaporating and recrystallizing in ethanol, 30 g of product were obtained.
Yield: 88%
Melting point: 163° C.
NMR spectrum (DMSO) δ ppm:
6.51, d; 7.22, d; 4.20, s:
6 benzodioxan protons 9.31, s and 2.00. s: NH-COCH$_3$

| 4.00, t (J = 6Hz) | 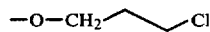 |
| 3.74, t (J = 6Hz) |  |
| 2.07, t (J = 6Hz) | 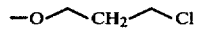 |

IR spectrum: NHCOCH$_3$ bands at 1660-1555 and 3380 cm$^{-1}$.

By the same process, but from the corresponding reagents, the compounds of formula (XXVIII) shown in Table II below are obtained.

TABLE II

XXVIII

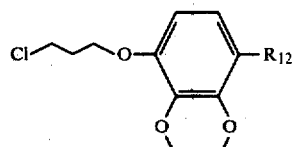

| Code number | —R$_{12}$ | Melting point °C. | Yield % | NMR spectrum or elementary analysis |
|---|---|---|---|---|
| 771 162 | —CONH—CH$_3$ | 103 | 100 | NMR (DMSO δ ppm: 7.4 d (J = 10Hz); 6.5 d (J = 10Hz) and 4.3 s (6 benzodioxan protons) 7.8 (m) and 2.88 d (J = |

TABLE II-continued

XXVIII

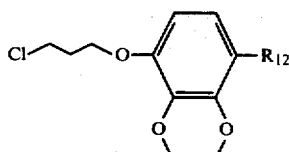

| Code number | $-R_{12}$ | Melting point °C. | Yield % | NMR spectrum or elementary analysis |
|---|---|---|---|---|
| 780 039 | $-NHCONHCH_3$ | 216 | 70 | 5Hz) CONHCH$_3$; 4.1, t (J = 6Hz); 3.75, t, (J = 6Hz) and 2.1 q (J = 6Hz) O⌒⌒Cl Calculated % C = 51.92, H = 5.70, N = 9.32 Obtained % C = 51.68, H = 5.57, N = 9.38 |

2nd step: 1-[3-(4-acetyl-2,3-ethylenedioxy)phenoxy]-propyl-4-(3,4,5-trimethoxycinnamoyl)-piperazine (I)

A mixture of 15.3 g (0.05 mole) of 3,4,5-trimethoxycinnamoyl piperazine, of 13.6 g of 3-(4-acetyl-2,3-ethylenedioxyphenoxy)-1-chloropropane, used in the crude state, and of 20.7 g of potassium carbonate in 100 ml of acetonitrile was brought to reflux for 12 hours. Then, the solvent was filtered and evaporated, the residue was filtered on a silica column, eluted with chloroform and the product obtained was crystallized in ether. 5 g of product was obtained.

Yield: 21%
Melting point: 134° C.
Empirical formula: $C_{29}H_{36}N_2O_8$
Molecular weight: 540.59

| Elementary analysis: | C | H | N |
|---|---|---|---|
| Calculated % | 64.43 | 6.71 | 5.18 |
| Obtained % | 64.10 | 6.77 | 5.00 |

By the same process, but from the corresponding reagents, the compounds of formula I, shown in Table I, and bearing the code numbers 771 163, 771 172 and 780 040 were obtained.

EXAMPLE 4

1-(3-N-methylanilino-2-hydroxy)propyl-4-(3,4,5-trimethoxycinnamoyl)piperazine, hydrated oxalate (I)

Code number: 770 495

1st step: 1-(2,3-epoxypropyl)-4-(3,4,5-trimethoxycinnamoyl)piperazine.

Code number: 770 319

A solution of 61.2 g of 3,4,5-trimethoxycinnamoyl piperazine, 137 g of epibromhydrin and 138 g of potassium carbonate in 300 ml of acetonitrile was brought to reflux for 8 hours. Then, the solvent was evaporated and the residue chromatographed on a silica column. Eluted with chloroform, the product was obtained which was crystallized in ethyl ether. Weight: 26.4 g.

Yield: 36%
Melting point: 126° C.
Empirical formula: $C_{19}H_{36}N_2O_5$
Molecular weight: 362.41

| Elementary analysis: | C | H | N |
|---|---|---|---|
| Calculated % | 62.96 | 7.23 | 7.73 |
| Obtained % | 62.48 | 7.33 | 7.47 |

2nd step: 1-(3-N-methylanilino-2-hydroxy)propyl-4-(3,4,5-trimethoxycinnamoyl)piperazine, hydrated oxalate.

A solution of 3.62 g (0.01 mole) of 1-(2,3-epoxypropyl-4-(3,4,5-trimethoxycinnamoyl)piperazine (IIIh) and 1.07 g (0.01 mole) of N-methylaniline in 20 ml of ethanol was brought to reflux for 93 hours. The solvent was evaporated, the residue was taken up in chloroform, extracted with an aqueous solution of methane sulfonic acid, the aqueous phase was basified with sodium bicarbonate, extracted with chloroform, the solvent was evaporated, the residue was taken up in 40 ml of acetone and 0.75 g of oxalic acid in solution in 10 ml of acetone was added. After filtering, 1.9 g of product were obtained.

Yield: 34%
Melting point: 154° C.
Empirical formula: $C_{29}H_{38}N_3O_{11}$
Molecular weight: 615.427

| Elementary analysis: | C | H | N |
|---|---|---|---|
| Calculated % | 56.54 | 6.42 | 6.83 |
| Obtained % | 56.80 | 6.28 | 6.82 |

EXAMPLE 5 parafluoro cinnamoyl piperazine (IIa)

Code number: 770 125

To a toluene solution of 20 g of parafluoro cinnamoic acid was added 20 cm$^3$ of thionyl chloride and the mixture was brought to 70°-80° C. for 1 hour.

The solvents were evaporated and the residue (14 g) was slowly added to a solution of 13.2 g of piperazine in 150 ml of acetic acid. They were left in contact for 3 days at room temperature, then the solvent was evaporated, the residue was taken up in a mixture of chloroform and dilute hydrochloric acid, decanted and the aqueous phase was basified with a concentrated NaOH solution, extracted with chloroform, washed with water, the solvent was evaporated and the residue filtered on silica. 14.5 g of product were obtained.
Yield: 81%
Melting point: 90° C.
NMR spectrum:

δ ppm=6.82, d, and 7.68, d, (J=16Hz)—CH=CH—
=7.52, m, and 7.08 m, aromatic protons
=3.62, m 2.91, m: and 1.92, s, piperazinic protons.

By the same process but from the corresponding reagents were obtained: 3,4,5-trimethoxycinnamoyl homopiperazine chlorhydrate (IIb) code number: 760 360;
Yield: 73%
Melting point: 164° C.
Empirical formula: $C_{17}H_{25}ClN_2O_4 + H_2O$
Molecular weight: 374.859

Elementary analysis:

|  | C | H | N |
|---|---|---|---|
| Calculated % | 54.47 | 7.26 | 7.47 |
| Obtained % | 54.52 | 7.26 | 7.34 | the compounds of formula (IIa) appearing in Table III below, and the 4-acetoxy-3,5-dimethoxycinnamoyl piperazine (IIa) which is used in the crude state for the synthesis of compound (Ia) used in Example 2.

It was brought to reflux for 2 hours, then washed with chloroform, acidified with concentrated hydrochloric acid and extracted with chloroform. The solvent was evaporated and the oil obtained was crystallized in isopropyl ether.
18.5 g of product were obtained
Yield: 20%
Melting point: 120° C.
NMR spectrum:

δ ppm=6.71, d; and 7.62, d, (J=16Hz):—CHOCH
7.08 s, aromatic protons
3.82, s,: 2 $CH_3O$ By the same process, but from the corresponding reagents, 4-isopropoxy-3,5-dimethoxycinnamoic acid (V) was obtained which was used in the crude state in the synthesis of the compound of formula (IIa), code number 770 623, appearing in Table III.

EXAMPLE 7

1-(4-cyano-2,3-ethylenedioxyphenoxy)-2,3-epoxypropane (III)

Code number: 770 584

A mixture of 31 g of 5-cyano-8-hydroxy-1,4-benzodioxan (VII) (Code number 770 583), 38.35 g of epibromhydrin and 133 g of potassium carbonate in 300 ml of acetonitrile was brought to reflux for 12 hours. The

TABLE III

| Code number | R″— | Form | Empirical Formula | Molecular weight | Melting Point (°C.) | Yield % | ELEMENTARY ANALYSIS | | | |
|---|---|---|---|---|---|---|---|---|---|---|
| | | | | | | | % | C | H | N |
| 770125 | F— | Base | $C_{13}H_{15}FN_2O$ | 234.27 | 90 | 81 | Calc. | 66.65 | 6.45 | 11.96 |
| | | | | | | | Obt. | 66.45 | 6.36 | 11.79 |
| 770137 | (methylenedioxyphenyl) | Base | $C_{14}H_{16}N_2O_3$ | 260.284 | 124 | 58 | Calc. | 64.60 | 6.20 | 10.76 |
| | | | | | | | Obt. | 64.20 | 6.32 | 10.62 |
| 770537 | $CH_3O$, $CH_3O$ | Base | $C_{15}H_{20}N_2O_3$ | 276.326 | Liquid | 31 | 3.8 s ($OCH_3$) δppm: 2.35,s,(N—H)/; 2.9 m and 3.7m: (N—$CH_2$); 6.8,d and 7.6,d (J = 14Hz): (CH=CH); 6.4 to 6.7,m (aromatic) | | | |
| 770339 | $OCH_3$, $C_2H_5O$—, $OCH_3$ | Base | $C_{17}H_{24}N_2O_4$ | 320.378 | 117 | 78 | Calc. | 63.73 | 7.55 | 8.74 |
| | | | | | | | Obt. | 63.42 | 7.64 | 8.77 |
| 770623 | $CH_3O$, isopropoxy, $CH_3O$ | Base | $C_{18}H_{26}N_2O_4$ + 1/6 $H_2O$ | 337.41 | 98 | 27 | Calc. | 64.07 | 7.87 | 8.30 |
| | | | | | | | Obt. | 64.18 | 7.78 | 8.30 |

EXAMPLE 6

4-ethoxy-3,5-dimethoxycinnamoic acid (V)

Code number: 770 431

A solution of 100 g of ethyl ester of sinapic acid, 208 g of ethyl iodide and 184 g of potassium carbonate in 1500 ml of acetonitrile was brought to reflux for 6 hours. The solution was filtered, the filtrate was evaporated and the residue was crystallized which was dissolved in a solution of 36 g of NaOH in 360 ml of water.

mixture was filtered, the product then crystallized in the filtrate, it was filtered out and recrystallized in acetonitrile.

31.6 g of product were obtained.
Yield: 79%
Melting point: 167° C.
Empirical formula: $C_{12}H_{11}NO_4$
Molecular weight: 233.116

| Elementary analysis: | C | H | N |
|---|---|---|---|
| Calculated % | 61.82 | 4.76 | 6.01 |
| Obtained % | 61.92 | 4.76 | 5.95 |

By the same process but from the corresponding reagents, the compounds of formula (III), appearing in Table IV below, were obtained as well as the following compounds of formula III:

- 1-(2-acetyl-3,4,5-trimethoxyphenoxy)-2,3-epoxy-propane
- 1-(4-cyanomethylphenoxy)-2,3-epoxypropane
- 1-(4-n-propylcarbonyl-2,3-ethylenedioxyphenoxy)-2,3-epoxypropane
- 1-(5-acetyl-2,3-ethylenedioxyphenoxy)-2,3-epoxy-propane
- 2,3-epoxy-7-propoxy-4-acetamidoindane which are used in the crude state in the synthesis of the corresponding compounds of formula I, appearing in Table I, following the process used in Example I.

TABLE IV $$\underset{O}{\triangle}\!\!\!-\!X'\!-\!Ar' \quad (III)$$

| Code No. | X' | —Ar' | Empirical Formula | Molecular Weight | Melting Point °C. | Yield % | IR or NMR spectrum or elementary analysis |
|---|---|---|---|---|---|---|---|
| 780 352 | oxygen | 4-COCH$_3$, 3-F phenyl | C$_{11}$H$_{11}$FO$_3$ | 210.19 | Eb = 155/0.3 | 53 | NMR (CDCl$_3$) ppm ($\delta$): 2.5,s, (CH$_3$—CO) 2.9,m,3.4 m, 4.2,m: (O-epoxy); 7,t(J=8Hz) & 7.7, d (J=8Hz): (aromatic) |
| 770 996 | " | 4-COCH$_3$, 3-OCH$_3$ phenyl | C$_{12}$H$_{14}$O$_4$ | 222.23 | 63 | 50 | NMR (CDCl$_3$) ppm ($\delta$): 2.6,s, (CH$_3$—CO) 3.9,s, (OCH$_3$) 2.8,m; 3.4,m; 4.2,m: (O-epoxy); 7,d(10Hz) & 7.55,m: (aromatic) |
| 780 400 | " | 4-COCH$_3$, 3-Cl phenyl | C$_{11}$H$_{11}$ClO$_3$ | 226.65 | 78 | 100 | NMR (CDCl$_3$) ppm ($\delta$) 2.5,s, (CH$_3$CO) 2.9,m; 3.4,m & 4.2,m (O-epoxy) 6.95,d (J=9Hz) & 7.8,m (aromatic) |
| 771 060 | " | 4-NO$_2$, 3-Cl phenyl | C$_9$H$_8$ClNO$_4$ | 229.62 | Eb = 170/0.1 | 83 | C H N<br>Cal. (%) 47.07 3.51 6.10<br>Obt. (%) 46.90 3.46 6.07 |
| 780 447 | " | 4-COC$_2$H$_5$, 3-OCH$_3$ phenyl | C$_{13}$H$_{16}$O$_3$ | 220.26 | >50 | 61 | NMR (CDCl$_3$) ppm ($\delta$): 1.1,t, (J=6Hz): (CH$_3$—CH$_2$—) 2.9, (J=8Hz): (CH$_3$—CH$_2$—CO—); 2.9,m & 3.4,m & 4.2,m: (O-epoxy); 3.95,s,(OCH$_3$); 6.95,d(J=10Hz) & 7.5,m: (aromatic) |
| 770 856 | " | 4-NO$_2$, 3-CH$_3$ phenyl | C$_{10}$H$_{11}$NO$_4$ | 209.20 | 70 | 45 | NMR (CDCl$_3$) ppm ($\delta$): 2.6,s: (CH$_3$—Ar) 2.8,m & 3.4,m & 4.2,m: (O-epoxy) 6.8,m & 8,d (J=10Hz): (aromatic) |
| 770 741 | " | 4-NHCONHCH$_3$, 3-CH$_3$ phenyl | C$_{12}$H$_{15}$N$_2$O$_3$ | 236.26 | 174 | 50 | NMR (CDCl$_3$) ppm ($\delta$): 2.1,s (CH$_3$—Ar); 2.6,d(CH$_3$—N); 2.6,m & 3.15,m & 4,m; (O-epoxy); 3.15,s,: (Ar—NH); 6.1,q (J=4Hz): (NH—CH$_3$); 6.7,m & 7.4, m: (aromatic) |
| 770 934 | " | 4-NHCONHCH$_3$, 2,3-di-OCH$_3$ phenyl | C$_{13}$H$_{18}$N$_2$O$_5$ | 282.29 | 144 | 83 | NMR (CDCl$_3$) ppm ($\delta$): 2.9,d(J= 5Hz):(CH$_3$N—); 2.85,m & 3.4,m & 4.1,m: (O-epoxy); 3.87 & 3.90,s(2-OCH$_3$); 5.6,q (J=5Hz) (NH—CH$_3$); 6.7,d & 7.7,d (J= 9Hz): (aromatic); 7.2,s, (NH—Ar) |

TABLE IV-continued $$\underset{O}{\triangle}\diagdown X'-Ar' \quad (III)$$

| Code No. | X' | —Ar' | Empirical Formula | Molecular Weight | Melting Point °C. | Yield % | IR or NMR spectrum or elementary analysis |
|---|---|---|---|---|---|---|---|
| 780 291 | " | 3,5-Cl₂-4-CH₃-C₆H₂-NHCONHCH₃ | C₁₁H₁₂Cl₂N₂O₃ | 291.14 | 198 | 21 | NMR (CDCl₃), ppm (δ): 2.5,d: (CH₃—NH); 2.6,m & 3.2 m & 4.0,m: (O-epoxide); 6.1,q: (NH—CH₃); 7.4,s,: (aromatic) 8.7,s: (Ar—NH) |
| 780 338 | " | 3,5-Cl₂-4-CH₃-C₆H₂-COCH₃ | C₁₁H₁₀Cl₂O₃ | 261.10 | 68 | 100 | NMR (CDCL₃) ppm (δ): 2.5,s: (CH₃CO—) 2.8,m & 3.4,m & 4.2,m: (O-epoxide) 7.85,s: (aromatic) |
| 780 358 | " | 3,5-(CH₃O)₂-4-CH₃-C₆H₂-COCH₃ | C₁₃H₁₆O₅ | 252.26 | 70 | 100 | NMR (CDCl₃) ppm (δ): 2.5,s (CH₃CO) 2.7,m & 3.3,m & 4.2,m: (O-epoxide) 3.85,s, (OCH₃); 7.2,s (aromatic) |
| 780 360 | " | 3,5-(CH₃O)₂-4-CH₃-C₆H₂-COOEt | C₁₄H₁₈O₆ | 282.28 | 65 | 100 | NMR (CDCl₃) ppm (δ): 1.4,t, (J=7Hz): CH₃—CH₂;4.4,q (J=7Hz): (CH₂—CH₃) 3.9,s,: (OCH₃); 2.7,m & 3.35,m & 4.2,m: (O-epoxide); 7.3,s: (aromatic) |
| 780 356 | " | 3,5-(CH₃O)₂-4-CH₃-C₆H₂-NHCONHCH₃ | C₁₃H₁₈N₂O₅ | 282.29 | 155 | 50 | NMR (CDCl₃) ppm (δ): 2.7,d, (NH—CH₃); 2.7,m & 3.4, & 4.m: (O-epoxide); 3.65,s; (OCH₃); 5.6,q: (NH—CH) 6.6,s=(aromatic); 7.4,s; (NH—Ar) |
| 780 008 | " | benzodioxane-OCH₃ | C₁₂H₁₄O₅ | 238.232 | 110 | 83 | NMR (CDCl₃) δ ppm: 6.5,d(J=10Hz); 6.35d (J=10Hz) & 4.3s (6 benzodioxane protons) 3.8 s OCH₃ 4.1; 3.35 & 2.75,m O-epoxide |
| 780 003 | " | benzodioxane-OCOCH₃ | C₁₃H₁₄O₆ | 266.242 | 160 | 91 | Elementary analysis:<br>      C    H<br>Cal. (%) 58.64 5.30<br>Obt. (%) 58.60 5.43 |
| 770 584 | " | benzodioxane-CN | C₁₂H₁₁NO₄ | 233.116 | 167 | 79 | Elementary analysis:<br>      C    H    N<br>Cal. (%) 61.82 4.76 6.01<br>Obt. (%) 61.92 4.76 5.95 |
| 780 372 | " | benzodioxane-COO—CH(CH₃)₂ | C₁₅H₁₈O₆ | 294.294 | | 65 | NMR (CDCl₃ δ ppm: 7.35,d(J=10Hz); 6.5,d(J=10Hz) & 4.35s (6 benzodioxane protons) 5.15,m; 1.35,d(J=6Hz) COO 4.2;3.35 & 2.8 m O-epoxide |
| 780 368 | " | benzodioxane-COO-C(CH₃)₃ | C₁₆H₁₁O₆ | 305.296 | 57 | 87 | Elementary analysis:<br>      C    H<br>Cal. (%) 62.32 6.54<br>Obt. (%) 62.47 6.66 |

TABLE IV-continued $$\underset{O}{\triangle}\!\!\!\!\!\!\!\!\!\!\!\!\!\!\!\!\!\!\!\!\!\!\!\!\!\!\!\!-X'-Ar' \quad (III)$$

| Code No. | X' | —Ar' | Empirical Formula | Molecular Weight | Melting Point °C. | Yield % | IR or NMR spectrum or elementary analysis |
|---|---|---|---|---|---|---|---|
| 780 300 | " | benzodioxane—COOC$_5$H$_{11}$(n) | C$_{17}$H$_{21}$O$_6$ | 321.338 | 83 | 77 | Elementary analysis:<br>    C    H<br>Cal. (%) 63.24 6.88<br>Obt. (%) 63.21 6.75 |
| 780 332 | " | benzodioxane—COO—cyclohexyl | C$_{18}$H$_{21}$O$_6$ | 333.348 | 79 | 64 | Elementary analysis:<br>    C    H<br>Cal. (%) 64.66 6.63<br>Obt. (%) 64.57 6.46 |
| 770 204 | " | benzodioxane—CONH$_2$ | C$_{12}$H$_{13}$NO$_5$ | 251.232 | 209 | 86.5 | NMR (DMSO) δ ppm: 7.4,d(J=10 Hz); 6.7d (J=10Hz) & 4.35s (6 benzodioxane protons)<br>7.3 m (CONH$_2$)<br>4.2; 3.2 & 2.7m O—epoxide |
| 760 708 | " | benzodioxane—CONHCH$_3$ | C$_{13}$H$_{15}$NO$_5$ | 265.258 | 132.5 | 89 | δ ppm: 7.42,d, (J=10Hz); 6.51, d, (J=10Hz) & 4.32,s, (6 benzodioxane protons)<br>δ=7.40 (m) & 2.92,d, (J=5Hz): CONH—CH$_3$<br>δ=4.30; 3.35 & 2.80m, O—epoxide |
| 770 830 | " | benzodioxane—CONH—cyclohexyl | C$_{18}$H$_{23}$NO$_5$ | 333.372 | 102 | 75 | NMR (DMSO) 7.3,d(J=10Hz); 6.65d (J=10Hz) & 4.35s (6 benzodioxane protons)<br>7.6d; 1.0–2.0, (massive)<br>CONH—cyclohexyl<br>4.3; 3.35 & 2.7m O—epoxide |
| 770 851 | " | benzodioxane—CONH—phenyl | C$_{18}$H$_{17}$NO$_4$ | 327.324 | 190 | 87 | NMR δ ppm 7.3,d(J=10Hz); 6.7d(J=10Hz) & 4.38s (6 benzodioxane protons)<br>7.8,m; 7.4,m; 11,s CONH—phenyl<br>4.3; 3.35 & 2.75 m O—epoxide |
| 770 544 | " | benzodioxane—NHCO Et | C$_{14}$H$_{17}$NO$_5$ | 279.284 | 127 | 75 | NMR (CDCl$_3$)δ ppm: 7.75,d(J=10 Hz); 6.5d (J=10Hz) & 4.28s (6 benzodioxane protons 7.45,s; 2.35,q(J=6Hz); 1.20,t(J=6Hz)<br>—NHCO$_2$Et 4.2; 3.35 & 2.75 m O—epoxide |
| 770 600 | " | benzodioxane—NHCOC$_4$H$_{9n}$ | C$_{16}$H$_{21}$NO$_5$ | 307.336 | 121 | 79 | NMR(CDCl$_3$)δ ppm: 7.8,d(J=10Hz) 6.5d(J=10Hz) & 4.28s (6 benzodioxane protons) 7.5s; 2.4,m; 0.8 & 2.0, massive NHCOC$_4$H$_{9n}$<br>4.2; 3.4 & 2.8 m O—epoxide |
| 770 691 | " | benzodioxane—NHCO—iPr | C$_{15}$H$_{19}$NO$_5$ | 293.310 | 150 | 85 | NMR(CDCl$_3$)δ ppm: 7.82,d(J=10Hz) 6.53d(J=10Hz) & 4.30s (6 benzodioxane protons) 2.5,m; 1.20,<br>d (J=6Hz); 7.5s NH CO—iPr<br>4.25; 3.35 & 2.8 m O—epoxide |
| 770 613 | " | benzodioxane—NHCO—tBu | C$_{16}$H$_{21}$NO$_5$ | 307.336 | 87 | 98 | NMR(CDCl$_3$)δ ppm: 7.8,d(J=10Hz); 6.45,d(J=10Hz) & 4.25,s (6 benzodioxane protons) 7.8,s & 1.25,s NHCO+ 4.3; 3.35<br>& 2.80 m O—epoxide |

TABLE IV-continued (III) structure: benzodioxane-X'—Ar' with epoxide

| Code No. | X' | —Ar' | Empirical Formula | Molecular Weight | Melting Point °C. | Yield % | IR or NMR spectrum or elementary analysis |
|---|---|---|---|---|---|---|---|
| 770 532 | " | benzodioxane-NHCO-cyclohexyl | $C_{18}H_{25}NO_5$ | 333.37 | 143 | 100 | NMR (CDCl$_3$) δ ppm: 7.8,d (J=10Hz); 6.5,d(J=10Hz) & 4.35,s (6 benzodioxane protons) 7.5,s & 1.0 & 2.3 (massive) NHCO—cyclohexyl 4.3; 3.35 & 2.80 m O-epoxide |
| 770 528 | " | benzodioxane-NHCO-phenyl | $C_{18}H_{17}NO_5$ | 327.324 | 153 | 90 | NMR (CDCl$_3$) δ ppm: 7.9,d (J=10Hz); 6.55,d(J=10Hz) & 4.3s (6 benzodioxane protons) 8.2,s; 7.8 & 7.45,m NHCO—phenyl 4.1; 3.35 & 2.8 m O-epoxide |
| 770 306 | " | benzodioxane-NHCONH—Et | $C_{14}H_{18}N_2O_5$ | 294.300 | 196 | 90 | NMR (DMSO) δ ppm: 7.5,d (J=10Hz); 6.5,d(J=10Hz) & 4.3,s (6 benzodioxane protons) 7.6,s; 6.6,m; 3.85,q (J=6Hz) & 1.05,t(J=6Hz) (NH—CONH—C$_2$H$_5$) 4.2; 3.3 & 2.8 m O-epoxide |
| 770 482 | " | benzodioxane-NHCONHC$_3$H$_{7n}$ | $C_{15}H_{20}N_2O_5$ | 308.326 | 176 | 68 | NMR (DMSO) δ ppm: 7.45,d (J=10 Hz); 6.45,d(J=10Hz) & 4.4,s (6 benzodioxane protons) 7.65s 6.7,m; 3.9,m; 1.4,m & 0.9,d (J=6Hz) (NHCONHC$_3$H$_{7n}$) 4.2; 3.1 & 2.8 m O-epoxide |
| 770 629 | " | benzodioxane-NHCONH-iPr | $C_{15}H_{20}N_2O_5$ | 308.326 | 155 | 85 | NMR (DMSO) δ ppm: 7.45,d(J=10 Hz); 6.45,d(J=10Hz) & 4.3 (6 benzodioxane protons) 7.5,s; 6.65,s; 3.75,m; 1.1,d(J=6Hz) (NHCONH—iPr) 4.2; 3.1 & 2.7 m O-epoxide |
| 770 633 | " | benzodioxane-NHCONHC$_4$H$_{9n}$ | $C_{16}H_{22}N_2O_5$ | 322.362 | 186 | 69 | NMR (DMSO) δ ppm: 7.5,d(J=10 Hz); 6.5,d(J=10Hz) & 4.3s (6 benzodioxane protons) 7.65,s; 6.7,m; 3.3m; 3.1m; 1.2,m & 0.95,m (NHCONHC$_4$H$_{9n}$) 4.25; 3.3 & 2.8 m O-epoxide |
| 770 710 | " | benzodioxane-NH—CONH-tBu | $C_{16}H_{22}N_2O_5$ | 322.352 | 146 | 28 | NMR (CDCl$_3$) δ ppm: 7.3,d(J=10 Hz); 6.4,d(J=10Hz) & 4.1 (6 benzodioxane protons) 6.6,s; 5.1,s & 1.15s NHCONH-tBu 4.0; 3.3 & 2.7 m O-epoxide |
| 780 222 | " | benzodioxane-NHCONH-phenyl-OCH$_3$ | $C_{19}H_{20}N_2O_6$ | 372.366 | 220 | 85 | Elementary analysis:<br>        C    H    N<br>Cal. (%) 61.28 5.41 7.52<br>Obt. (%) 61.00 5.45 7.62 |
| 771 232 | " | benzodioxane-NHCON(CH$_3$)$_2$ | $C_{14}H_{18}N_2O_5$ | 294.300 | 160 | 80 | Elementary analysis:<br>        C    H    N<br>Cal. (%) 57.13 6.17 9.52<br>Obt. (%) 56.82 6.25 9.24 |

TABLE IV-continued $$\underset{O}{\triangle}\!\!\!-\!\!X'\!-\!Ar' \quad (III)$$

| Code No. | X' | —Ar' | Empirical Formula | Molecular Weight | Melting Point °C. | Yield % | IR or NMR spectrum or elementary analysis |
|---|---|---|---|---|---|---|---|
| 771 148 | " | benzodioxane-NHCON(morpholine) | $C_{16}H_{20}N_2O_6$ | 336.336 | 164 | 55 | Elementary analysis:<br>　　　　C　　H　　N<br>Cal. (%)　57.13　5.99　8.33<br>Obt. (%)　56.98　6.10　8.33 |
| 771 237 | " | benzodioxane-N(CH$_3$)CONHCH$_3$ | $C_{14}H_{18}N_2O_5$ | 294.300 | oil | 88 | NMR (CDCl$_3$) ppm ($\delta$): 6.75,d (J=10Hz); 6.5,d(J=10Hz) & 4.3,s (6 benzodioxane protons) 7.35,s; 3.1,s & 2.7,d(J=5Hz) (N(CH$_3$)CONHCH$_3$) 4.3; 3.3 & 2.8,m O△O |
| 770 524 | " | benzodioxane-NHCOOEt | $C_{14}H_{17}NO_6$ | 295.284 | 130 | 95 | NMR (CDCl$_3$) ppm ($\delta$): 7.5,d (J=10Hz); 6.5,d(J=10Hz) & 4.25,s (6 benzodioxane protons) 6.8,s; 4.2,q(J=6Hz) & 1.15,t (J=6Hz) (NH CO$_2$Et) 4.15; 3.35 & 2.75,m O△O |
| 770 311 | " | benzodioxane-CH$_2$COOEt | $C_{15}H_{18}O_6$ | 294.294 | 72 | 85 | Elementary analysis:<br>　　　　C　　H<br>Cal. (%)　61.21　6.17<br>Obt. (%)　61.25　6.31 |
| 770 385 | " | benzodioxane-CH$_2$CONH$_2$ | $C_{13}H_{15}NO_5$ | 265.258 | 200 | 60 | NMR (DMSO) ppm ($\delta$): 6.7,d (J=10Hz); 6.5,d(J=10Hz) & 4.2,s (6 benzodioxane protons) 7.1,m; 3.3,s CH$_2$ CO NH$_2$ 4.2; 3.35 & 2.7,m O△O |
| 780 381 | " | benzodioxane-CH$_2$CONHCH$_3$ | $C_{14}H_{17}NO_5$ | 269.284 | 174.6 | 75 | NMR (DMSO) ppm ($\delta$): 6.65,d (J=10Hz); 6.5(J=10Hz) & 4.2,s (6 benzodioxane protons) 7.5,m; 3.3,s; 2.55,d(J=5Hz) (CH$_2$ CO NH CH$_3$) 4.3; 3.4 & 2.8,m O△O |
| 780 454 | S | phenyl-COCH$_3$ | $C_{11}H_{12}O_2S$ | 2o8.27 | <50 | 15 | NMR (CDCl$_3$) ppm ($\delta$): 2.5,s: (CH$_3$—CO); 2.7,m & 3.2,d: (S△O) 7.35,d & 7.8,d (J=8Hz): (aromatic) |
| 780 473 | " | phenyl(OCH$_3$)-COCH$_3$ | $C_{12}H_{14}O_3S$ | 238.30 | <50 | 89 | NMR (CDCl$_3$) ppm ($\delta$): 2.5,s: (CH$_3$—CO); 3.9,s: (O CH$_3$); 2.6,m & 3.2,m: (S△O); 7.4,m: (aromatic) |
| 780 224 | oxygen | benzodioxane-NHCOCH$_3$ | $C_{13}H_{15}NO_5$ | 265.258 | 75 | 63 | NMR (CDCl$_3$) ppm ($\delta$): 7.7,d (10Hz); 6.55,d(10Hz) & 4.25,s (6 benzodioxane protons) 8.3,s; 2.2,s (NH CO CH$_3$) 4.2; 3.3 & 2.9,m O△O |

TABLE IV-continued $$\underset{O}{\triangleleft_O}\!\!-\!\!X'\!-\!Ar' \quad (III)$$

| Code No. | X' | —Ar' | Empirical Formula | Molecular Weight | Melting Point °C. | Yield % | IR or NMR spectrum or elementary analysis |
|---|---|---|---|---|---|---|---|
| 780 307 | " | benzodioxole-COCH₃ | C₁₂H₁₂O₅ | 236.216 | 80 | 85 | Elementary analysis:<br>　　　　C　　H<br>Cal. (%)　61.01　5.12<br>Obt. (%)　60.80　4.81 |
| 780 345 | " | benzodioxole-NHCOCH₃ | C₁₂H₁₃NO₅ | 251.232 | 121 | 95 | NMR (CDCl₃) ppm (δ): 7.3,d (10Hz); 6.5,d(10Hz) & 5.95,s (4 benzodioxole protons) 7.3,s; 2.15,s (NH CO CH₃) 4.4; 3.3 2.8,m O$\triangleleft$O |
| 780 408 | " | benzodioxole-NHCONHCH₃ | C₁₂H₁₄N₂O₅ | 266.248 | 168 | 75 | NMR (DMSO) ppm (δ): 7.3,d (J=10Hz); 6.5,d(J=10Hz) & 6.0,s (4 benzodioxole protons) 7.9,s; 6.2,m & 2.65,d (NH CO NH CH₃) 4.2; 3.35 & 2.8,m O$\triangleleft$O |
| 780 240 | " | benzodioxepine-COCH₃ | C₁₄H₁₅O₅ | 263.260 | 72 | 96 | NMR (CDCl₃) ppm (δ): 7.4,d (J=10Hz); 6.65,d(J=10Hz); 4.3,m & 2.3,m (8 benzodi-oxepine protons) 2.53,s COCH₃ 4.2; 3.4 & 2.8,m O$\triangleleft$O |
| 780 392 | " | benzodioxepine-NHCOCH₃ | C₁₄H₁₇O₅ | 265.276 | 124 | 91 | NMR (CDCl₃) ppm (δ): 7.85,d (J=10Hz); 6.6,d(J=10Hz); 4.25,m & 2.25,m (8 benzodi-oxepine protons) 7.75,s; 2.18,s NH CO CH₃ 4.2; 3.35 & 2.75,m O$\triangleleft$O |
| 780 467 | " | benzodioxepine-NHCONHCH₃ | C₁₄H₁₈N₂O₅ | 294.290 | 178 | 68 | NMR (DMSO) ppm (δ): 7.65,d (J=10Hz); 6.58,d(J=10Hz); 4.08,m & 2.1,m (8 benzodi-oxepine protons) 7.8,s; 6.6,m 2.6,d NH CO NH CH₃ 4.1; 3.3 & 2.75,m O$\triangleleft$O |
| 771 314 | " | naphthalene-COCH₃ | C₁₅H₁₄O₃ | 242.262 | 106 | 54 | Elementary analysis:<br>　　　　C　　H<br>Cal. (%)　74.36　5.83<br>Obt. (%)　74.08　5.91 |
| 771 035 | " | naphthalene-NHCOCH₃ | C₁₅H₁₅NO₃ | 257.278 | 186 | 78 | Elementary analysis:<br>　　　　C　　H　　N<br>Cal. (%)　70.02　5.88　5.44<br>Obt. (%)　69.75　5.60　5.53 |
| 771 030 | " | naphthalene-NHCONHCH₃ | C₁₅H₁₇N₂O₃ | 273.302 | 212 | 68 | NMR (DMSO) ppm (δ): 8.22,m; 7.55,m & 6.9,d (naphthalene protons) 8.3,m; 6.2,m; 2.72,d (NH CO NH CH₃) 4.3; 3.4 & 2.8,m O$\triangleleft$O |
| 771 152 | " | indane-NHCONHCH₃ | C₁₄H₁₈N₂O₃ | 262.300 | 218 | 86 | NMR (DMSO) ppm (δ): 7.42,d; (J = 10Hz); 6.6,d (J = 10Hz); 2.65,m & 2.0,m (indane protons) 7.55,s; 6.1,m; 2.6,d (NH CO NH CH₃) 4.1; 3.25 & 2.7,m O$\triangleleft$O |

TABLE IV-continued $$\underset{O}{\triangle}\diagdown X'-Ar' \quad (III)$$

| Code No. | X' | —Ar' | Empirical Formula | Molecular Weight | Melting Point °C. | Yield % | IR or NMR spectrum or elementary analysis |
|---|---|---|---|---|---|---|---|
| 780 127 | " | (tetrahydronaphthyl)—COCH$_3$ | C$_{15}$H$_{18}$O$_3$ | 246.294 | 80 | 40 | Elementary analysis:<br>　　　　C　　H<br>Cal. (%)　73.14　7.37<br>Obt. (%)　73.02　7.67 |
| 780 043 | " | (tetrahydronaphthyl)—NHCOCH$_3$ | C$_{15}$H$_{19}$NO$_3$ | 261.320 | 172 | 84 | NMR (DMSO) ppm (δ): 7.0,d;<br>(J = 10Hz); 6.65,d (J = 10Hz);<br>2.55,m & 1.65,m (10 tetra-<br>hydronaphthalene protons)<br>9.3,s & 2.0,s (NH CO CH$_3$)<br>4.1; 3.25 & 2.7,m O△O |
| 771 156 | " | (tetrahydronaphthyl)—NHCONHCH$_3$ | C$_{15}$H$_{20}$N$_2$O$_3$ | 276.326 | 224 | 80 | Elementary analysis:<br>　　　　C　　H　　N<br>Cal. (%)　65.19　7.30　10.14<br>Obt. (%)　64.94　7.35　10.59 |
| 780 451 | " | (tetrahydronaphthyl ketone) | C$_{13}$H$_{14}$O$_3$ | 218.24 | Eb = 178/0.4 | 65 | NMR (CDCl$_3$) ppm (δ): 6.8,m<br>& 8,d: (aromatic)<br>2.7,m & 3.4,m & 4.1,m (O△O)<br>2.1,m & 2.8,m (CH$_2$—CH$_2$—CH$_2$—CO) |
| 760 845 | " | (benzodioxane)—CH$_3$ | C$_{12}$H$_{14}$O$_4$ | 222.232 | 66 | 92 | ppm (δ) = 6.63,d(J = 10Hz);<br>　　　　6.42,d(J = 10Hz); &<br>　　　　4.24,s: benzodioxane<br>　　　　protons<br>= 2.16,s: —CH$_3$<br>= 4.21; 3.18 & 2.80,m: O△O |
| 740 454 | " | (benzodioxane)—COCH$_3$ | C$_{13}$H$_{14}$O$_5$ | 250.24 | 128 | | Elementary analysis:<br>　　　　C　　H<br>Cal. (%)　62.39　5.63<br>Obt. (%)　62.15　5.79 |
| 760 698 | " | (benzodioxane)—COOEt | C$_{14}$H$_{16}$O$_6$ | 280.268 | 95 | 100 | ppm (δ) = 7.42 & 6.51,d (J = 10<br>Hz); 4.32,s: benzo-<br>dioxane protons<br>= 4.30,q (J = 7Hz) &<br>1.35,t(J = 7Hz): COOEt<br>= 4.28; 3.28; 2.80,m: O△O |
| 750 568 | " | (benzodioxane)—NHCOCH$_3$ | C$_{13}$H$_{15}$NO$_5$ | 265.26 | 180 | | Elementary analysis:<br>　　　　C　　H　　N<br>Cal. (%)　58.86　5.70　5.28<br>Obt. (%)　58.62　5.13　5.13 |
| 770 609 | " | (benzodioxane)—NHCOC$_3$H$_{7n}$ | C$_{15}$H$_{19}$NO$_5$ | 293.310 | 133 | 76 | NMR (CDCl$_3$) ppm (δ): 7.78,d<br>(J = 10Hz); 6.5,d (J = 10Hz) &<br>4.28,s (benzodioxane protons)<br>7.4,s; 2.3,m; 1.7,m & 0.97,t<br>(NH CO C$_3$H$_{7n}$) 4.1; 3.35 &<br>2.80,m O△O |

TABLE IV-continued $$\text{(III)} \quad \underset{O}{\diagdown}\!\!\diagup\!\!-\!\!X'\!-\!Ar'$$

| Code No. | X' | —Ar' | Empirical Formula | Molecular Weight | Melting Point °C. | Yield % | IR or NMR spectrum or elementary analysis |
|---|---|---|---|---|---|---|---|
| 770 080 | " | benzodioxane-NHCONH-cyclohexyl | $C_{18}H_{24}N_2O_5$ | 348.388 | 220 | 70 | ppm ($\delta$) = 7.50 & 6.45,d (J = 10Hz); 4.23,s: benzodioxane protons<br>= 7.54 & 6.70,m: —NH—CO—NH—<br>= 1.5,m: cyclohexyl<br>= 4.20; 3.60; 2.64;m: $O\diagdown\diagup O$ |
| 770 084 | " | benzodioxane-NHCONH-$\phi$ | $C_{18}H_{18}N_2O_5$ | 342.34 | 208 | 75 | ppm ($\delta$) = 7.60 & 6.55,d (J = 10Hz); 4.32,s: benzodioxane protons<br>= 8.10 & 6.70,m: —NH—CONH—<br>= 7.30,m: phenyl<br>= 4.20; 3.40; & 2.72,m: $O\diagdown\diagup O$ |
| 770 076 | " | benzodioxane-NHCONHCH₃ | $C_{13}H_{16}N_2O_5$ | 280.274 | 235 | 40 | ppm ($\delta$) = 7.50 & 6.51,d (J = 10Hz); 4.30,s: benzodioxane protons<br>= 7.68,s & 6.55,m: —NH—CO—NH—<br>= 2.62,d (J = 5Hz): —CH₃<br>= 4.02, 3.32; & 2.70,m: $O\diagdown\diagup O$ |
| 760 703 | " | benzodioxane-CH₂OH | $C_{12}H_{14}O_5$ | 238.38 | oil | 93 | Elementary analysis:<br>　　　　C　　H<br>Cal. (%)　60.50　5.92<br>Obt. (%)　60.78　5.82 |
| 770 186 | " | benzodioxane-CH₂CN | $C_{13}H_{13}NO_4$ | 247.242 | 138 | 86 | ppm ($\delta$) = 6.85; & 6.52;d (J = 10Hz) & 4.32,s: benzodioxane protons<br>= 3.60,s: —CH₂—CN<br>= 4.18; 3.22 & 2.90,m: $O\diagdown\diagup O$ |
| 780 388 | S | benzodioxane | $C_{11}H_{12}O_3S$ | 224.272 | oil | 85 | Elementary analysis:<br>　　　　C　　H<br>Cal. (%)　58.91　5.39<br>Obt. (%)　58.50　5.20 |
| 780 383 | S | benzodioxane-COCH₃ | $C_{13}H_{15}O_4S$ | 266.308 | 72 | 97 | Elementary analysis:<br>　　　　C　　H<br>Cal. (%)　58.63　5.30<br>Obt. (%)　58.77　5.53 |

EXAMPLE 8

2-methyl-4-N-methylcarbamoylaminophenol (VIIa)

Code number: 770 702

To a suspension of 2-methyl-4-hydroxy aniline (12.3 g) in 300 cm³ of chloroform was slowly added 59.cm³ of methyl isocyanate. They were left in contact for 3 hours at room temperature, then the solvent was evaporated and the residue crystallized in ethanol.

5.5 g of product were obtained.
Yield: 30%
Melting point: 198° C.
Empirical formula: $C_9H_{12}N_2O_2$
Molecular weight: 182.20

| Elementary analysis: | C | H | N |
|---|---|---|---|
| Calculated % | 59.98 | 6.71 | 15.55 |

-continued

| Elementary analysis: | C | H | N |
|---|---|---|---|
| Obtained % | 59.57 | 6.70 | 15.96 |

By the same process, but from the corresponding reagents, compounds of formula (VIIa), code numbers 770 920, 780 290, 780 355, the compound of formula (VIIb) code number 771 029 and the compounds of formula (VIIc), code numbers 771 151 and 771 155, shown in Table V below, were obtained.

EXAMPLE 9

4-acetamido-7-hydroxy indane (VIId)

Code number: 771 304

A mixture of 25 g of 7-hydroxy-4-amino indane and of 8 ml of acetic anhydride in 400 ml of iced water was stirred for 30 minutes. After filtering, the precipitate was washed with water and ethyl ether and was recrystallized in isopropanol.

25 g of product were obtained.
Yield: 78%
Melting point: 220° C.
Empirical formula: $C_{11}H_{13}NO_2$
Molecular weight: 191.22

| Elementary analysis: | C | H | N |
|---|---|---|---|
| Calculated % | 69.09 | 6.85 | 7.33 |
| Obtained % | 69.17 | 7.08 | 7.08 |

By the same process, but from the corresponding reagents, the compound of formula (VIId) of code number 700 042 and shown in Table V below, was obtained.

EXAMPLE 10

2-methoxy-4-acetyl thiophenol (VIIe)

Code Number: 780 472
1st step: 1-N,N-dimethylthiocarbamoyloxy-2-methoxy-4-acetylbenzene (X)
Code Number: 780 470

A solution of 3.3 g of acetovanillone, of 2.9 g of dimethyl thiocarbamoyl and of 8.2 g of potassium carbonate in 80 cm³ of acetonitrile was brought to 70° C. for 30 minutes. After filtering, the solvent was evaporated and the residue recrystallized in ethanol. 3.3 g of product were obtained.
Yield: 66%
Melting point: 130° C.
NMR spectrum:
δ ppm=7.54, m & 7.11, d, (J=9 Hz):aromatic protons
=3.82, s —OCH₃
=3.21, s, and 3.15, s,:

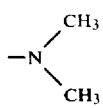

=2.56, s,: COCH₃
By the same process, but from the corresponding reagents, the following compounds of formula (Xa) were obtained:
5-N,N-dimethylthiocarbamoyloxy-1,4-benzodioxane Code Number: 780 385
Yield: 98%
Melting point: 98° C.
Empirical form.: $C_{11}H_{13}NO_3S$
Molecular weight: 239.39

| Elementary analysis: | C | H | N |
|---|---|---|---|
| Calculated (%) | 55.21 | 5.48 | 5.85 |
| Obtained (%) | 55.10 | 5.40 | 5.62 |

5-N,N-dimethylthiocarbamoyloxy-8-acetyl-1,4-benzodioxane
Code Number: 780 380
Yield: 75%
Melting point: 149° C.
Empirical formula: $C_{13}H_{15}NO_4S$
Molecular weight: 281.32

| Elementary analysis: | C | H | N |
|---|---|---|---|
| Calculated (%) | 55.50 | 5.37 | 4.98 |
| Obtained (%) | 55.34 | 5.21 | 4.68 |

2nd step: 1-N,N-dimethylcarbamoylthio-2-methoxy-4-acetylbenzene (IX)
Code Number: 780 471

Under a flow of argon, 13 g of 1-N,N-dimethylthiocarbamoyloxy-2-methoxy-4-acetylbenzene, obtained in the preceding step were heated for 35 minutes at 250° C. Then, the residue was chromatographed on a silica column. After elution with chloroform 6 g of product were obtained.
Yield: 46%
Melting point: 116° C.
NMR spectrum:
δ ppm=7.57, s, aromatic protons
=3.91, s,: —OMe
=3.03, s,:

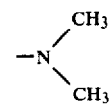

=2.52, s,: COCH₃
By the same process, but from the corresponding reagents, the following compounds of formula (IXa) were obtained:
5-N,N-dimethylcarbamoylthio-1,4-benzodioxane
Code Number: 780 386
Yield: 59%
Melting point: 78° C.
NMR spectrum:
δ ppm=6.98, m; and 4.22, s: benzodioxane protons
=3.02, s,

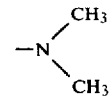

IR spectrum: band at 1640 cm⁻¹

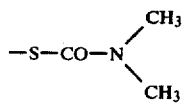

5-N,N-dimethylcarbamoylthio-8-acetyl-1,4-benzodioxane
 Code Number: 780 381
 Yield: 39%
 Melting point: 155° C.
 Empirical formula: $C_{13}H_{15}NO_4S$
 Molecular weight: 281.32

Elementary analysis:

|  | C | H | N |
|---|---|---|---|
| Calculated (%) | 55.50 | 5.37 | 4.98 |
| Obtained (%) | 55.73 | 5.54 | 5.05 |

3rd step: 2-methoxy-4-acetylthiophenol (VIIe)
 Code Number: 780 472

A solution of 5.6 g of 4-N,N-dimethylthiocarbamoyloxy-3-methoxy acetophenone obtained in the previous step, 2.6 g of soda (NaOH) in 210 ml of methanol and 60 ml of water was brought to reflux for two hours. Then, the solvents were evaporated, the residue was taken up in water, washed with ethyl acetate, the aqueous phase was acidified with concentrated hydrochloric acid, extracted with chloroform which was dried and the solvent was evaporated. 3.5 g of product were obtained.
 Yield: 87%
 Melting point: 50° C.
 NMR spectrum:
 δ ppm = 7.20, m: aromatic protons
 = 4.16, s: —SH
 = 3.96, s,: —OMe
 = 2.57, s,: —COCH₃

By the same process, but from the corresponding reagents, the compounds of formula (VIIf), code numbers 780 387 and 780 382, shown in Table V below, were obtained.

EXAMPLE 11

5-hydroxy-8-N-cyclohexyl carboxamido-1,4-benzodioxane (VIIk)

Code Number: 770 829

A solution of 34.5 g of 5-benzyloxy-8-N-cyclohexyl-carboxamido-1,4-benzodioxane (XIId), code number 770 828, in presence of 6.8 g of palladium on 5% charcoal was hydrogenolysed in an autoclave at room pressure and temperature. Once the absorption of hydrogen was completed, and after filtration, the filtrate was evaporated.
 Yield: 92%
 Melting point: 182° C.
 NMR spectrum:
 δ ppm = 7.24, d; 6.48, d, (J = 10 Hz) and 4.18 s,: benzodioxane protons
 = 7.62, d, (J = 7 Hz): —COHN—
 = 10.1, m,: —OH
 = 3.78, m and 1.5, m,:

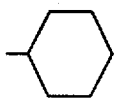

By the same process, but from the corresponding reagents, the compounds of formula (VII), corresponding to formula (VIIk) shown in Table V below, were obtained.

EXAMPLE 12

5-hydroxy-8-n-propylcarbonyl-1,4-benzodioxane (VIII)

Code Number: 750 769

A solution of 44.4 g (0.2 mole) of 8-n-propyl carbonyloxy-1,4-benzodioxane in 240 ml of nitrobenzene was cooled to a temperature of less than 10° C. and 40 g (0.3 mole) of aluminum chloride were slowly added. It was left for 48 hours at room temperature, diluted with water, the organic phase was decanted, the solvent was evaporated, and the residue was chromatographed on a silica column. With toluene-chloroform mixtures, 27 g (61%) of 5-hydroxy-6-n-propylcarbonyl-1,4-benzodioxane were eluted. Then, with a 90% chloroform-10% methanol mixture, 5 g of 5-hydroxy-8-n-propylcarbonyl-1,4-benzodioxane were eluted.
 Yield: 11%
 Melting point: 84° C.
 Empirical formula: $C_{12}H_{14}O_4$
 Molecular weight: 222.23

Elementary analysis:

|  | C | H |
|---|---|---|
| Calculated (%) | 64.87 | 6.35 |
| Obtained (%) | 64.84 | 6.24 |

EXAMPLE 13

5-hydroxy-8-acetamido-1,4-benzodioxane (VIIm)

Code number: 750 548

1st step: 5-hydroxy-8-acetyl-1,4-benzodioxane oxime (XIII)
 Code number: 750 527

A solution of 19.4 g (0.1 mole) of 5-hydroxy 8-acetyl-1,4-benzodioxane (VIIi) and 10.4 g (0.15 mole) of hydroxylamine hydrochloride in 50 ml of pyridine and 50 ml of ethanol was brought to reflux for 7 hours. Then, the solvents were evaporated and the residue crystallized in water. 12 g of product were obtained.
 Yield: 55%
 Melting point: 145° C.
 Empirical form.: $C_{10}H_{11}NO_4 \cdot \tfrac{1}{2} H_2O$
 Molecular weight: 218.20

Elementary analysis:

|  | C | H | N |
|---|---|---|---|
| Calculated (%) | 55.04 | 5.54 | 6.42 |
| Obtained (%) | 55.24 | 5.68 | 6.31 |

2nd step: 5-hydroxy-8-acetamido-1,4-benzodioxane 250 ml of acetic acid were saturated with gaseous hydrochloric acid, then 20.9 g (0.1 mole) of 5-hydroxy-8-acetyl-1,4-benzodioxane oxime, obtained in the previous step, were added. It was brought to reflux for 5 hours, then the solvents were evaporated, the residue was crystallized in water and recrystallized in ethanol. 7 g of product were obtained.
Yield: 33%
Melting point: 170° C.
Empirical formula: $C_{10}H_{11}NO_4$
Molecular weight: 209.20

| Elementary analysis: | C | H | N |
|---|---|---|---|
| Calculated (%) | 57.41 | 5.30 | 6.70 |
| Obtained (%) | 57.17 | 5.31 | 6.54 |

EXAMPLE 14

5-hydroxy-8-methyl-1,4-benzodioxane (VIIn)

Code number: 760 844

A solution of 14.7 g (0.05 mole) of 5-benzyloxy-8-hydroxymethyl-1,4-benzodioxane (XIp) code number 760 701, crude, non-crystallized, in 300 ml of absolute alcohol was hydrogenolysed at room pressure and temperature, in the presence of 3 g of palladium on 5% charcoal. Once the absorption of hydrogen was completed, the catalyst was filtered and the solvent was evaporated. A liquid was obtained.

NMR spectrum:

δ ppm = 8.90, s, 1 phenolic proton
= 6.42 and 6.21, d, (J = 10 Hz)
= 4.17, s,: benzodioxane protons
= 1.98, s,: —CH$_3$

EXAMPLE 15

5-benzyloxy-8-methoxy-1,4-benzodioxane (XIa)

Code number: 780 006

1st step: 5-benzyloxy-8-acetyl-1,4-benzodioxane (XV)
Code Number: 760 694

A suspension of 97 g (0.5 mole) of 5-hydroxy-8-acetyl-1,4-benzodioxane (VIIi), of 127 g (1 mole) of benzyl chloride and 155 g (1.12 mole) of potassium carbonate in 150 ml of absolute alcohol was brought to reflux for 24 hours. After filtration the solvent was evaporated, the residue was taken up in chloroform, washed with a solution of soda (NaOH) 1 N, the solvent was evaporated and the product was crystallized in alcohol, 135 g of product expected were obtained.
Yield: 95%
Melting point: 133° C.
Empirical formula: $C_{17}H_{16}O_4$
Molecular weight: 284.29

| Elementary analysis: | C | H |
|---|---|---|
| Calculated (%) | 71.82 | 5.67 |
| Obtained (%) | 71.76 | 5.76 |

2nd step: 5-benzyloxy-8-acetoxy-1,4-benzodioxane (XIb)
Code Number: 780 001

To a solution of 58 g of 5-benzyloxy-8-acetyl-1,4-benzodioxane (XV) obtained in the previous step, in 300 ml of formic acid, were added, at −5° C., 25 g of a 36% solution of hydrogen peroxide in 100 ml of formic acid. The mixture was left at 0° C. for 72 hours then poured on a mixture of water and ice, the precipitate formed was filtered, washed in water and recrystallized in a mixture of ethyl acetate and isopropyl ether.

Yield: 89%
Melting point: 104° C.
Empirical formula: $C_{17}H_{16}O_5$
Molecular weight: 300.39

| Elementary analysis: | C | H |
|---|---|---|
| Calculated (%) | 67.97 | 5.37 |
| Obtained (%) | 68.15 | 5.55 |

3rd step: 5-benzyloxy-8-hydroxy-1,4-benzodioxane (XIV)
Code Number: 780 005

To a solution of 58.3 g of 5-benzyloxy-8-acetoxy-1,4-benzodioxane obtained in the previous step, in 400 ml of methanol, are added 75 g of potassium carbonate, at room temperature. Then, after 30 minutes, the solution was filtered, the solvent evaporated, and the residue was taken up in water and acidified in concentrated hydrochloric acid. The precipitate obtained was filtered and recrystallized in alcohol: 47.3 g of the product were obtained.
Yield: 94%
Melting point: 131° C.
Empirical formula: $C_{15}H_{14}O_4$
Molecular weight: 258.25

| Elementary analysis: | C | H |
|---|---|---|
| Calculated (%) | 69.75 | 5.46 |
| Obtained (%) | 69.83 | 5.39 |

4th step: 5-benzyloxy-8-methoxy-1,4-benzodioxane (XIa)
Code Number: 780 006

To a solution of 45 g of 5-benzyloxy-8-hydroxy-1,4-benzodioxane obtained in the preceding step and 52 g of potassium carbonate in 500 ml of acetone, there was slowly added 33.5 g of dimethylsulfate then 20 ml of a 10% solution of methanolic caustic potash. The solution was then brought to reflux for 2 hours and 30 minutes, filtered, the solvents were evaporated, the residue was taken up in ethyl ether, washed with water, dried and the solvent was evaporated. 47 g of product were obtained.
Yield: 98%
Melting point: 70° C.
NMR Spectrum:

δ ppm = 7.36, d, and 6.47, d, (J = 2 Hz) and 4.23, s, benzodioxane protons
= 7.35, m and 5.03, s: —CH$_2$—φ
= 3.78, s,: —OCH$_3$

EXAMPLE 16

5-benzyloxy-8-isopropoxycarbonyl-1,4-benzodioxane (XIc)

Code Number: 780 370

1st step: (5-benzyloxy-1,4-benzodioxane)yl-8-carboxylic acid (XVI)
Code Number: 760 695

To a solution of 29 g (0.1 mole) of 5-benzyloxy-8-acetyl-1,4-benzodioxane (XV) obtained in the first step of Example 15, in 150 ml of pyridine were added 25.8 g (0.1 mole) of iodine. Then, the mixture was brought to 100° C. for 1 hour, the excess of pyridine was driven off, the residue was taken up in water, filtered and the precipitate obtained was put in solution in 450 ml of a 50/50 alcohol-water mixture. A solution of 70 g of soda (NaOH) in 200 ml of water was slowly added, then, washing with chloroform was carried out and the precipitate formed was filtered and dissolved in an aqueous solution of soda (NaOH). Acidification was carried out up to pH≃1 by means of hydrochloric acid, then it was concentrated and filtered. 25 g of product were obtained.

Yield: 35%
Melting point: ≃200° C.
Empirical formula: $C_{16}H_{14}O_5$
Molecular weight: 286.27

Elementary analysis:

|  | C | H |
|---|---|---|
| Calculated (%) | 67.12 | 4.93 |
| Obtained (%) | 66.91 | 5.00 |

2nd step: 5-benzyloxy-8-isopropoxycarbonyl-1,4-benzodioxane

To a toluene solution of 31 g of (5-benzyloxy-1,4-benzodioxane)yl-8-carboxylic acid obtained in the previous step, 50 ml of thionyl chloride were added and the mixture was brought to 70°–80° C. for 2 hours. Then, the solvents were evaporated, the residue was dissolved in 200 ml of tetrahydrofuran, and 15 cm³ of isopropyl alcohol and 70 cm³ of triethylamine were added. The mixture was brought to 60° C. for 3 hours, then the precipitate formed was filtered, the filtrate evaporated and the residue chromatographed on a silica column and eluted with chloroform. 20 g of product were obtained which was recrystallized in isopropyl ether.

Yield: 71%
Melting point: 96° C.
NMR spectrum:

δ ppm = 7.38 (d), and 6.57, d, (J = 10 Hz) and 4.23, s, benzodioxane protons
= 7.28, s, and 5.08 s: $CH_2-\phi$
= 5.09, quintet, and 1.14, d (J = 6 Hz) —COO<
IR spectrum: 1710 and 1200 cm⁻¹ band: COO<

With the same method, but from the corresponding reagents, the compounds of formula XIc was prepared, given in Table VI and bearing code numbers 780 366, 780 298 and 780 330.

EXAMPLE 17

(5-benzyloxy-1,4-benzodioxane)yl-8-ethyl carboxylate (XIc)

Code Number: 760 696

A solution of 25 g (0.095 mole) of (5-benzyloxy-1,4-benzodioxane)yl-8-carboxylic acid obtained in the first step of Example 16, in 500 ml of alcohol and 50 ml of a solution of hydrochloric acid in 4.4 N ethanol was brought to reflux for 4 hours. Then, the solvent was evaporated, the residue was taken up in chloroform, washed with a solution of sodium bicarbonate, with water, then it was dried, and the solvent was evaporated. 26 g of ester were obtained.

Yield: 90%
IR spectrum: band at 1708 and 1200 cm⁻¹ (COOEt)
NMR spectrum:

δ ppm = 7.22, d; 6.51, d; (J = 10 Hz) and 4.38, s,: benzodioxane protons
= 7.18, s: benzylic aromatic protons
= 5.20, s: $O-CH_2-\phi$
= 4.35, q, and 1.35, t, (J = 8 Hz): COOEt.

EXAMPLE 18

5-benzyloxy-8-N-cyclohexyl carboxamido-1,4-benzodioxane (XId)

Code Number: 770 828

To a toluene solution of 30 g of (5-benzyloxy-1,4-benzodioxane)yl-8-carboxylic acid obtained in the first step of Example 16, were added 30 cm³ of thionyl chloride and it was brought to 70°–80° C. for 2 hours. Then, the solvents were evaporated, the residue was dissolved in 200 ml of tetrahydrofuran and 24 ml of triethylamine and 19 ml of cyclohexylamine were added. The mixture was brought to 60° C. for 3 hours and after filtration the filtrate was evaporated and the residue recrystallized in a mixture of ethyl acetate and hexane.

Yield: 82.5%
Melting point: 117° C.
Empirical formula: $C_{22}H_{25}NO_4$
Molecular weight: 367.49

Elementary analysis:

|  | C | H | N |
|---|---|---|---|
| Calculated (%) | 71.91 | 6.86 | 3.81 |
| Obtained (%) | 71.99 | 6.78 | 3.69 |

With the same method, but from the corresponding reagents, the compounds of formula XId were obtained, given in Table VI and bearing the following code numbers 770 202 and 770 849.

EXAMPLE 19

5-benzyloxy-8-N-methylcarboxamido-1,4-benzodioxane (XId)

Code Number: 760 706

To a solution cooled below 0° C. of 20 g (0.07 mole) of (5-benzyloxy-1,4-benzodioxane)yl-8-carboxylic acid obtained in the 1st step of Example 16, in 200 ml of anhydrous tetrahydrofuran, 11 ml of triethylamine were added, then 6.9 ml of ethyl chloroformate. It was stirred at 0° C. for 2 hours, then a gaseous flow of methylamine was passed for 90 minutes. Then, the solution was left for one hour at room temperature, the tetrahydrofuran was evaporated, the residue was taken up in chloroform, then it was washed with water, the solvent was evaporated and recrystallized in alcohol. 18 g of product were obtained.

Yield: 80%
NMR spectrum:

δ ppm = 7.70, d; 6.60, d, (J = 10 Hz) and 4.32, s,: benzodioxane protons
= 7.35, s,: benzylic aromatic protons
= 5.18, s,: $O-CH_2-\phi$
= 7.36, m, —NH—CO—
= 2.91, d, (J = 6 Hz); $CH_3$—CO—N<

EXAMPLE 20

5-benzyloxy-8-propionamido-1,4-benzodioxane (XIe)

Code Number: 770 542

To a solution of 30 g of 5-benzyloxy-8-amino-1,4-benzodioxane (XX); code number 760 727, in 250 ml of chloroform and 21.3 ml of triethylamine, cooled to 0° C., 12.1 cm³ of propionyl chloride were slowly added. Then, it was stirred for 17 hours, washed with a solution of diluted hydrochloric acid, with water, with an aqueous solution of sodium bicarbonate, then with water, the organic phase was evaporated and the residue recrystallized in ethyl acetate.

Yield: 73%
Melting point: 139° C.
NMR spectrum:
δ ppm=7.42, d; 6.51, d, (J=10 Hz) and 4.20, s: benzodioxane protons
 =7.78, d, (J=9 Hz): —NH—CO—
 =7.35, s and 5.03, s: CH$_2$—φ
 =2.17, q, and 1.11, t (J=7 Hz): CO—CH$_2$—CH$_3$
IR spectrum: bands at 3400, 1670 and 1510 cm$^{-1}$: —NH—CO—

With the same method, but from the corresponding reagents, the compounds of formula XIe were obtained, appearing in Table VI and bearing code numbers 770 689; 770 598; 770 611; 770 530; 770 526 and 770 607.

EXAMPLE 21

4-benzyloxy-2,3-methylene dioxy aniline (XXa) Code Number: 780 405

A solution of 34 g of 4-benzyloxy-2,3-methylene dioxy acetanilide (XIh), code number 780 343, in 120 ml of methanol was treated with 34 g of potassium hydroxide, for 1½ hour at reflux. Then, the precipitate formed was filtered and recrystallized in isopropyl alcohol. 13.4 g of product were obtained.

Yield: 50%
Melting point: 59° C.
NMR spectrum:
δ ppm=6.22, q, (J=9 Hz) aromatic protons of the benzodioxole group
 =5.84, s,

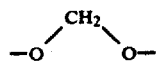

=7.36, s and 5.03, s,: —CH$_2$—φ
 =3.17, s, —NH$_2$

With the same method, but from the corresponding reagents, were obtained the compounds of formula (XXa), code number 780 464: 6-amino-9-benzyloxy-1,5-benzodioxepine.

Yield: 82%
Melting point: 92° C.
Empirical formula: C$_{16}$H$_{17}$NO$_3$
Molecular weight: 217.29

| Elementary analysis: | C | H | N |
|---|---|---|---|
| Calculated (%) | 70.89 | 6.32 | 5.16 |
| Obtained (%) | 70.72 | 6.39 | 5.13 | as well as the compound of formula (XX), code number 760 727: 5-benzyloxy-8-amino-1,4-benzodioxane:

Yield: 78%
Melting point: 130° C.
Empirical formula: C$_{15}$H$_{15}$NO$_3$
Molecular weight: 257.28

| Elementary analysis: | C | H | N |
|---|---|---|---|
| Calculated (%) | 70.02 | 5.88 | 5.44 |

| -continued Elementary analysis: | C | H | N |
|---|---|---|---|
| Obtained (%) | 69.73 | 5.94 | 5.24 |

EXAMPLE 22

4-benzyloxy-2,3-methylene dioxy acetanilide (XIh)

Code Number: 780 343

To a suspension of 100 g of 4-benzyloxy-2,3-methylene dioxy acetophenone oxime (XXII), code number 780 342, in 500 ml of acetic acid, 500 ml of acetic anhydride were slowly added, then a gaseous flow of hydrochloric acid was passed at 10° C., for 1 hour. Then, the solution was brought to 40°-50° C. for 5 hours, the solvents were evaporated, the residue was taken up with chloroform, then it was washed with water, the solvent was evaporated and the residue recrystallized in ethyl acetate.

Yield: 84%
Melting point: 148° C.
NMR spectrum:
δ ppm=7.18, m and 5.18 s: —CH$_2$φ
 =7.18, m (aromatic protons of the benzodioxole nucleus and of CH$_2$φ)
 =5.95, s,:

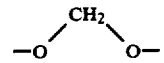

=2.09, s, CH$_3$—CO—N—
 =6.51 d, (J=9 Hz): NH—CO—
IR spectrum: 3260, 1650 cm$^{-1}$: band —NH—CO—

With the same method but from the corresponding reagents, the compound of formula (XIh) was obtained, code number 780 463, appearing in Table VI.

EXAMPLE 23

4-benzyloxy-2,3-methylene dioxy acetophenone oxime (XXII)

Code Number: 780 342

A solution of 192 g of 4-benzyloxy-2,3-methylene dioxy acetophenone (XIi); code number 780 305 and of 64 g of hydroxylamine hydrochloride in 500 ml of pyridine and 500 ml of ethanol were brought to reflux for 2 hours. Then, the solvents were evaporated, the residue was taken up in water and the precipitate formed was filtered.

Yield: 98%
Melting point: 168° C.
Empirical formula: C$_{16}$H$_{15}$NO$_4$
Molecular weight: 285.29

| Elementary analysis: | C | H | N |
|---|---|---|---|
| Calculated (%) | 67.36 | 5.30 | 4.91 |
| Obtained (%) | 67.31 | 5.30 | 4.91 |

With the same method, but from the corresponding reagents, 6-acetyl-9-benzyloxy-1,5-benzodioxepine oxime (XXII) was obtained, code number 780 390.

Yield: 90%
Melting point: 134° C.
NMR Spectrum:

δ ppm=13.00, m, =N—OH
 =6.51, d; 6.88, d, (J=10 Hz); 4.10, m; and 2.08, m: benzodioxepine protons
 =5.17 s and 7.19, s: CH$_2$—φ
 =2.20, s: —CH$_3$

EXAMPLE 24

5-benzyloxy-8-acetamido-1,4-benzodioxane (XIh)

Code Number: 760 606

Following the working method described in the first step of Example 15, but from 5-hydroxy-8-acetamido-1,4-benzodioxane (VIIm), code number 750 548, 91% of product was obtained.

Melting point: 148° C.

NMR spectrum:

δ ppm=7.35, d; 6.56, d, (J=10 Hz) and 4.24, s, benzodioxane protons
 =7.36, s, and 5.07, s,: CH$_2$—φ
 =7.76, d, (J=9 Hz): NH—CO—
 =2.17, s,: CH$_3$ IR spectrum: bands at 3270, and 1660 cm$^{-1}$: —NH—CO—CH$_3$

EXAMPLE 25

5-benzyloxy-8-N-ethyl carbamoyl amino-1,4-benzodioxane (XIf)

Code Number: 770 304

For 20 hours a mixture of 25 g of 5-benzyloxy-8-amino-1,4-benzodioxane, code number 760 727, and 8 ml of ethyl isocyanate in 300 ml of chloroform was maintained at reflux. Then, the solvents were evaporated in a vacuum and the residue recrystallized in ethanol.

Yield: 80%

Melting point: 188° C.

NMR spectrum:

δ ppm=7.41, d; 6.56, d, (J=10 Hz) and 4.19, s, benzodioxane protons
 =7.38, s, and 4.97, s,: —CH$_2$—φ
 =6.60, m and 7.40, m: NH—CO—NH
 =3.02, q and 1.00, t, (J=7 Hz): —CH$_2$—CH$_3$—

With the same method, but from the corresponding reagents, the compounds of formula (XIf) were obtained, appearing in Table VI and bearing the code numbers 770 074, 770 480, 770 627, 770 631, 770 708, 770 078, 770 082, 770 220, 780 406 and 780 465.

EXAMPLE 26

5-benzyloxy-8-ethoxy carbonylamino-1,4-benzodioxane (XIg)

Code Number: 770 522

To a solution of 30 g of 5-benzyloxy-8-amino-1,4-benzodioxane (XX), code number 760 727, in 250 ml of chloroform, 21.3 ml of triethylamine, then slowly, at 0° C., 15.2 g of ethyl chloroformate were added. The solution was stirred for 7 hours, filtered and the filtrate was washed with a diluted hydrochloric acid solution, with water, with a solution of sodium bicarbonate and with water. The solvent was evaporated and the residue recrystallized in ethyl acetate.

Yield: 74%

Melting point: 108° C.

NMR spectrum:

δ ppm=6.52, d; 7.41, d, (J=10 Hz) and 4.22, s,: benzodioxane protons
 =7.38, s and 5.08, s: CH$_2$—φ
 =4.10, q, and 1.14, t, (J=7 Hz): CH$_2$—CH$_3$
 =6.80, s, —NH—

IR spectrum: 3315 and 1692 cm$^{-1}$=NHCOOEt

EXAMPLE 24

4-benzyloxy-2,3-methylene dioxy acetophenone (XIi)

Code Number: 780 305

A mixture of 140 g of 4-benzyloxy-2,3-dihydroxy acetophenone (XXIV), code number 780 304, 295 g of diiodomethane and 300 g of potassium carbonate in 1200 ml of dimethyl formamide was brought to reflux for 5 hours. After filtering, the filtrate was evaporated, the residue was taken up in a 50/50 mixture of ethyl acetate and ether, then it was washed with water, the organic phase was evaporated and the residue was crystallized in ethanol.

Yield: 93%

Melting point: 101° C.

NMR spectrum:

δ ppm=6.55, d; 7.35, d, (J=10 Hz): aromatic protons of the benzodioxole nucleus
 =6.00, s,

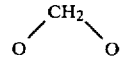

=7.38, s and 5.18, s,: CH$_2$—φ
=2.44 s,: —CH$_3$

IR spectrum: 1670 cm$^{-1}$: —CO—CH$_3$

With the same method, but from the corresponding reagents, the compound (XIi), code number 780 238, given in Table VI, was obtained.

EXAMPLE 28

4-benzyloxy-2,3-dihydroxy acetophenone (XXIV)

Code Number: 780 304

A mixture of 349 g of gallacetophenone, 1750 g of sodium bicarbonate and 260 g of benzyl chloride in 4000 ml of acetone was stirred for 2 hours at room temperature. Then the mixture was brought to reflux for 36 hours, filtered, the solvent was evaporated and the residue was taken up in ethyl acetate and diluted in isopropyl ether. 58% of crystallized product were obtained.

Melting point: 128° C.

Empirical formula: C$_{15}$H$_{14}$O$_4$

Molecular weight: 258.26

| Elementary analysis: | C | H |
|---|---|---|
| Calculated (%) | 69.75 | 5.46 |
| Obtained (%) | 69.48 | 5.60 |

EXAMPLE 29

5-benzyloxy-8-N,N'-dimethyl carbamoyl amino-1,4-benzodioxane (XIj)

Code Number: 771 235

First step: 5-benzyloxy-8-N-methylamino-1,4-benzodioxane (XXV)

Code Number: 771 234

A mixture of 40 g of 5-benzyloxy-8-amino-1,4-benzodioxane (XX), code number 760 727, 120 ml of formaldehyde (at 38% in an aqueous solution) and 29 g of 5,5-dimethylhydantoin in 300 ml of ethanol was brought to reflux for 12 hours. Then the solvent was evaporated, the residue was taken up in chloroform and washed by means of a diluted hydrochloric acid solution. The organic phase was evaporated and the residue dissolved in 90 ml of dimethylsulfoxide. 23 g of sodiumborohydride were slowly added, and brought to 100° C. for 30 minutes. Then it was diluted in 1500 ml of water, extracted with chloroform, washed with water and the solvent evaporated. The residue was chromatographed on a silica column. Eluted with chloroform, 34% of product was obtained.

Melting point: 62° C.
Empirical formula: $C_{16}H_{17}NO_3$
Molecular weight: 271.30

Elementary analysis:

|  | C | H | N |
|---|---|---|---|
| Calculated (%) | 70.83 | 6.32 | 5.16 |
| Obtained (%) | 70.70 | 6.29 | 4.90 |

Second step: 5-benzyloxy-8-N,N'-dimethyl carbamoyl amino-1,4-benzodioxane

A mixture of 22.4 g of 5-benzyloxy-8-N-methyl amino-1,4-benzodioxane, obtained from the preceding step, and 10 ml of methyl isocyanate in 100 ml of chloroform were brought to reflux for 2 hours, then the solvent was evaporated and the residue recrystallized in alcohol:

Yield: 74%
Melting point: 140° C.
Empirical formula: $C_{18}H_{20}N_2O_4$
Molecular weight: 328.36

Elementary analysis:

|  | C | H | N |
|---|---|---|---|
| Calculated (%) | 65.84 | 6.14 | 8.53 |
| Obtained (%) | 65.71 | 6.07 | 8.62 |

EXAMPLE 30

5-benzyloxy-8-morpholinocarbonylamino-1,4-benzodioxane (XIk)

Code Number: 771 146

A mixture of 38 g of 5-benzyloxy-8-ethoxycarbonylamino-1,4-benzodioxane (XIg), code number 770 522, and 300 ml of morpholine was brought to reflux for 16 hours, in the presence of a pinch of ammonium chloride. Then the morpholine in excess was evaporated and the residue was recrystallized in 96° ethanol.

Yield: 72%
Melting point: 184° C.
Empirical formula: $C_{20}H_{22}N_2O_5$
Molecular weight: 370.39

Elementary analysis:

|  | C | H | N |
|---|---|---|---|
| Calculated (%) | 64.85 | 5.67 | 7.56 |
| Obtained (%) | 64.85 | 5.95 | 7.74 |

EXAMPLE 31

5-benzyloxy-8-N,N-dimethylcarbamoyl amino-1,4-benzodioxane (XIl)

Code Number: 771 230

To a solution of 100 g of 5-benzyloxy-8-amino-1,4-benzodioxane (XX), code number 760 727, and 100 ml of triethylamine, in 1000 ml of chloroform were slowly added 47 ml of dimethylcarbamoyl chloride, at room temperature, then it was brought to reflux for 48 hours. After filtering, the filtrate was evaporated and the residue was recrystallized in ethanol. 60 g of product were obtained.

Yield: 47%
Melting point: 142° C.
Empirical formula: $C_{18}H_{20}N_2O_4$
Molecular weight: 328.36

Elementary analysis:

|  | C | H | N |
|---|---|---|---|
| Calculated (%) | 65.84 | 6.14 | 8.53 |
| Obtained (%) | 65.67 | 6.35 | 8.25 |

EXAMPLE 32

5-benzyloxy-8-cyanomethyl-1,4-benzodioxane (XIm)

Code Number: 770 119

First step: 5-benzyloxy-8-chloromethyl-1,4-benzodioxane (XXVI)

Code Number: 770 188

To a solution, cooled to −10° C., of 10 g (0.037 mole) of 5-benzyloxy-8-hydroxymethyl-1,4-benzodioxane (XIp), code number 760 701, in 100 ml of chloroform were slowly added 4.6 g (0.039 mole) of thionyl chloride. They were left in contact for 15 minutes, then the solvents were evaporated, the residue was taken up in chloroform, washed with a solution of sodium bicarbonate, dried and the solvent was evaporated. 10.4 g of unstable product were obtained which, after checking by chromatography on a thin silica layer, was used in the synthesis of the compound of formula (XIm), code number 770 119.

Second step: 5-benzyloxy-8-cyanomethyl-1,4-benzodioxane

A solution of 99 g (0.34 mole) of 5-benzyloxy-8-chloromethyl-1,4-benzodioxane, obtained in the previous step, 19 g (0.4 mole) of sodium cyanide and 0.5 g of sodium iodide in 1000 ml of anhydrous dimethylformamide was brought to 60° C. for 45 minutes. Then the solvent was driven off in a vacuum, the residue was taken up in 600 ml of a saturated solution of sodium bicarbonate and 300 ml of chloroform, the organic phase was decanted, dried and the solvent evaporated. 85 g of product were obtained.

Yield: 89%
Melting point: 95° C.
Empirical formula: $C_{17}H_{15}NO_3$
Molecular weight: 281.29

Elementary analysis:

|  | C | H | N |
|---|---|---|---|
| Calculated (%) | 72.58 | 5.18 | 4.98 |
| Obtained (%) | 72.15 | 5.47 | 4.84 |

EXAMPLE 33

5-benzyloxy-8-carboxamidomethyl-1,4-benzodioxane (XIn)

Code Number: 770 383

To a solution of 50 g of 5-benzyloxy-8-cyanomethyl-1,4-benzodioxane, obtained in the process of Example 32, in 250 ml of t-butanol were slowly added 39 g of pulverized potassium hydroxide, then it was brought to reflux for 20 minutes. Then the mixture was poured into 500 ml of an aqueous solution of sodium chloride, extracted with chloroform, washed with water, the solvent was evaporated and the residue recrystallized in ethanol.

Yield: 90%
Melting point: 166° C.
NRM spectrum:

δ ppm = 6.51, d; 6.72, d; (J = 10 Hz) and 4.30, s,: benzodioxane protons
= 7.37, s, and 5.16, s = $CH_2$—φ
= 5.76 m: —$COCH_2$
= 3.43, s,: —$CH_2$—CO—

EXAMPLE 34

5-benzyloxy-8-N-methylcarboxamidomethyl-1,4-benzodioxane (XIo)

Code Number: 770 379

First step: 2-[(5-benzyloxy-1,4-benzodioxane)yl-5] acetic acid (XXVII)

Code Number: 770 308

To a solution of 57 g of sodium hydroxide in 1 l of 50% aqueous ethanol, cooled to 0° C., were added 200 g of 5-benzyloxy-8-cyanomethyl-1,4-benzodioxane, obtained with the process of Example 32, then the ethanol was distilled; a solution of hydrochloric acid was added up to acid pH, it was washed with chloroform, acidified up to pH = 3 and filtered.

Yield: 78%
Melting point: 150° C.
NMR spectrum:

δ ppm = 6.43, d; 6.65, d, and 4.23, s,: benzodioxane protons
= 7.38, s, and 5.08, s,: —$CH_2$—φ
= 3.58, s,: —$CH_2$—COO—
= 9.20, m, —COOH Second step: 5-benzyloxy-8-N-methylcarboxamidomethyl-1,4-benzodioxane To a solution of 80 g of 2-[(5-benzyloxy-1,4-benzodioxane)yl-5] acetic acid obtained in the preceding step, in 500 ml of dimethyl formamide, cooled to 0° C., 50 ml of triethylamine were added, then 31 ml of ethyl chloroformate. Then a gaseous flow of methylamine was passed and the reaction was checked by chromatography on a thin silica layer. Then it was poured into iced water, the precipitate formed was filtered and taken up in chloroform. The organic phase as washed with a diluted hydrochloric acid solution, the organic phase was evaporated and the residue recrystallized in ethyl acetate. 70 g of product were obtained.

Yield: 85%
Melting point: 160° C.
NMR spectrum:

δ ppm = 6.02, d, 6.23, d (J = 9 Hz) and 3.82, s,: benzodioxane protons
= 6.94, s and 4.63, s,: —$CH_2$—φ
= 3.02, s,: $CH_2$—CO—
= 2.30, d, (J = 5 Hz): —$CH_3$
= 5.12, m, —NH—

IR spectrum: 3295 and 1640 cm$^{-1}$: —CONH—

EXAMPLE 35

5-benzyloxy-8-hydroxymethyl-1,4-benzodioxane (XIp)

Code Number: 760 701

A solution of 12.8 g (0.04 mole) of (5-benzyloxy-1,4-benzodioxane)yl-5-ethyl carboxylate, obtained according to the method of Example 17, in 50 ml of anhydrous tetrahydrofuran was added to a suspension of 1.54 g (0.04 mole) of lithium hydride and aluminum in 150 ml of tetrahydrofuran and left at room temperature for 30 minutes. Then it was hydrolyzed with an aqueous solution of sodium sulfate then with a saturated aqueous solution of sodium sulfate, filtered, the solvent was evaporated and the residue recrystallized in benzene. 11 g of product were thus obtained.

Yield: 97%
Melting point: 106° C.
NMR spectrum:

δ ppm = 6.78, d; 6.51, d; (J = 10 Hz) and 4.24, s,: benzodioxane protons
= 7.32, s, and 5.12, s;: —$CH_2$—φ
= 4.60 m, and 2.20 m,: —$CH_2OH$

EXAMPLE 36

5-benzyloxy-8-cyano-1,4-benzodioxane (XIq)

Code Number: 770 582

To a solution of 84.5 g of 5-benzyloxy-8-carboxamido-1,4-benzodioxane (XId), code number 770 202, obtained by the method of Example 18, in 1000 ml of benzene, were added 80 g of phosphorous pentachloride. The temperature rises to 40° C. after 45 minutes, the solvent was evaporated, and the residue was taken up in toluene, washed with water and the solvent was evaporated. The residue was recrystallized in ethyl acetate.

Yield: 62%
Melting point: 145° C.
NMR spectrum:

δ ppm = 6.50, d, 7.01, d, (J = 10 Hz) and 4.25, s,: benzodioxane protons
= 7.38 s, and 5.05 s,: $CH_2$—φ

IR spectrum: 2210 cm$^{-1}$: band —CN

EXAMPLE 37

5-benzyloxy-8-ethoxycarbonylmethyl-1,4-benzodioxane (XIr)

Code Number: 770 309

To a solution of 72 g of 2-[(5-benzyloxy-1,4-benzodioxane)yl-8] acetic acid, obtained by the method of the first step of Example 34, in 200 ml of ethanol, were added 100 ml of hydrochloric acid in ethanol 7.5 N, then it was brought to reflux for 30 minutes. The solvent was evaporated, the residue was taken up in chloroform, then it was washed with a saturated sodium bicarbonate solution, with water, and the solvent was evaporated. 98% of crystallized product was obtained.

Melting point: 86° C.
NMR spectrum:

δ ppm = 6.40, d; 6.61, d (J = 10 Hz) and 4.18, s,: benzodioxane protons
= 7.36, m, and 5.03, s: —$CH_2$—φ
= 3.37, s: —$CH_2$—COO
= 4.18, q and 1.10, t, (J = 8 Hz): —COO—$CH_2$—$CH_3$ Table VI, in which are shown the different compounds of formula (XI), is given below.

TABLE V

| Code Number | X' | —Ar' | H—X'—Ar' (VII) Empirical Formula | Molecular Weight | Melting Point °C. | Yield % | IR or NMR spectrum or elementary analysis |
|---|---|---|---|---|---|---|---|
| 770 702 | oxygen | 2-CH₃-phenyl-NHCONHCH₃ | $C_9H_{12}N_2O_2$ | 180.20 | 198 | 30 | Cal. (%) C 59.98 H 6.71 N 15.55; Obt. (%) C 59.57 H 6.70 N 15.96 |
| 770 920 | oxygen | 2,6-(OCH₃)₂-phenyl-NHCONHCH₃ | $C_{10}H_{14}N_2O_4$ | 226.23 | 118 | 51 | NMR (DMSO)ppm (δ): 2.6,d, (J=4Hz): (CH₃—NH); 3.8,s, (CH₃O) 6.5,d & 7.6,d(J=8Hz): (aromatic) 6.5,s, 7.6,s & 8.8,s: (NH & OH exchangeable) |
| 780 290 | oxygen | 2,6-Cl₂-phenyl-NHCONHCH₃ | $C_8H_8Cl_2N_2O_2$ | 235.07 | 212 | 97 | NMR (DMSO)ppm (δ): 2.6,d, (J=4Hz): (CH₃—NH) 7.4,s, (aromatic) 6.s & 8.5,s & 9.4,s: (NH & OH exchangeable) |
| 780 355 | oxygen | 2,6-(OCH₃)₂-phenyl-NHCONHCH₃ | $C_{10}H_{14}N_2O_4$ | 226.23 | 126 | 100 | NMR (DMSO)ppm (δ): 2.6,d, (J=5Hz): (CH₃—NH—) 3.7,s: (CH₃O—) 6.7,s: (aromatic) 5.8,q(J=4Hz)& 7.7,s & 8.2,s (NH & OH exchangeable) |
| 771 029 | oxygen | naphthyl-NHCONHCH₃ | $C_{12}H_{12}N_2O_2$ | 216.232 | 220 | 95 | NMR (DMSO)δppm 7.86,d(J=10Hz) 7.15,d(J=10Hz) & 7.7,m (6 naphthalene protons) 8.45,s (OH) 6.35,m & 2.75,d (NHCONHCH₃) |
| 771 151 | oxygen | indanyl-NHCONHCH₃ | $C_{11}H_{14}N_2O_2$ | 206.238 | 203 | 94 | NMR(DMSO)δppm 7.23,d(J=10Hz); 6.52,d(J=10Hz); 2.7,m & 2.0, m (indane protons) 8.7,s OH 7.5 s; 6.05,m & 2.7,d (NHCONHCH₃) |
| 771 155 | oxygen | tetrahydronaphthyl-NHCONHCH₃ | $C_{12}H_{16}N_2O_2$ | 220.264 | 228 | 99 | NMR(DMSO) 7.05,d(J=10Hz); δppm: 6.52,d(J=10Hz) 2.52,m & 1.65m (10 tetrahydronaphthalene protons) 8.83,s (OH) 7.25,s; 5.95,m & 2.62,d(NHCONHCH₃) |
| 771 304 | oxygen | indanyl-NHCOCH₃ | $C_{11}H_{13}NO_2$ | 191.222 | 220 | 78 | Elementary analysis: Cal. (%) C 69.09 H 6.85 N 7.33; Obt. (%) C 69.15 H 7.08 N 7.08 |
| 780 042 | oxygen | tetrahydronaphthyl-NHCOCH₃ | $C_{12}H_{15}NO_2$ | 205.248 | 190 | 50 | NMR(DMSO) 6.9,d(J=10Hz); 6.55,d(J=10Hz) 2.55,m & 1.67, m (10 tetrahydronaphthalene protons) 9.1,s (OH) 8.8,s; 2.0,s NHCOCH₃ |
| 780 472 | S | 2-OCH₃-phenyl-COCH₃ | $C_9H_{10}O_2S$ | 182.236 | <50 | 87 | NMR (CDCl₃) ppm (δ): 2.5,s,: (COCH₃) 3.9,s,: (OCH₃) 4.1,s,: (SH, exchangeable) & 7.4,m: (aromatic) |
| 780 387 | S | benzodioxin | $C_8H_8O_2S$ | 168.210 | oil | 85 | NMR (CDCl₃) 6.68,m 3 aromatic protons 4.18,s 4 dioxane protons 3.78, s SH |
| 780 382 | S | benzodioxin-COCH₃ | $C_{10}H_{10}O_3S$ | 210.246 | 78 | 90 | Elementary analysis Calc. % C 57.12 H 4.79; Obt. % C 57.15 H 4.66 |
| 760 707 | oxygen | benzodioxin-CONHCH₃ | $C_{10}H_{11}NO_4$ | 209.196 | 200 | 92 | Elementary analysis Calc. % C 57.41 H 5.30 N 6.70; Obt. % C 57.32 H 5.39 N 6.65 |

TABLE V-continued

| Code Number | X' | —Ar' | Empirical Formula H—X'—Ar' (VII) | Molecular Weight | Melting Point °C. | Yield % | IR or NMR spectrum or elementary analysis |
|---|---|---|---|---|---|---|---|
| 780 002 | oxygen | benzodioxane—OCOCH₃ | C₁₀H₁₀O | 210.18 | oil | 100 | NMR (CDCl₃) 6.41,s & 4.17,s (6 benzodioxane protons) δppm 5.55, s (OH) 2.23, s (OCOCH₃) |
| 770 583 | oxygen | benzodioxane—CN | C₉H₇NO₃ | 177.154 | 165 | 95.5 | NMR (CDCl₃) 7.08,d(J=10Hz); δppm 6.5,d(J=10Hz) & 4.35,s (6 benzodioxane protons) 9.35,s OH |
| 770 523 | oxygen | benzodioxane—NHCOOC₂H₅ | C₁₁H₁₃NO₅ | 239.22 | 123 | 70 | Elementary analysis<br>       C    H    N<br>Calc. % 55.22 5.48 5.86<br>Obt. % 55.27 5.17 5.95 |
| 780 371 | oxygen | benzodioxane—COO—iPr | C₁₂H₁₅O₅ | 238.232 | 125 | 87 | NMR (CDCl₃) 7.4,d(J=10Hz); δppm 6.5,d(J=10Hz) & 4.45,s (6 benzodioxane protons) 6.8 s OH 5.2, q(J=6Hz); 1.35,d (J=6Hz) COO—iPr |
| 780 367 | oxygen | benzodioxane—COO—tBu | C₁₃H₁₆O₅ | 252.288 | 156 | 94 | NMR (CDCl₃) 7.4,d(J=10Hz); δppm 6.5,d(J=10Hz) & 4.3,s (6 benzodioxane protons) 6.35 s OH 1.57 s COO+ |
| 780 299 | oxygen | benzodioxane—COOC₅—H₁₁n | C₁₄H₁₈O₅ | 266.284 | 45 | 100 | NMR (CDCl₃) 7.38,d(J=10Hz); δppm 6.48,d(J=10Hz) & 4.22,s (6 benzodioxane protons) 0.75 to 2.0 massive (COOC₅H₁₁n) |
| 780 331 | oxygen | benzodioxane—COO—cyclohexyl | C₁₅H₁₈O₅ | 278.294 | 114 | 100 | NMR (CDCl₃) 7.4,d(J=10Hz); δ ppm 6.48,d(J=10Hz) & 4.26,s (6 benzodioxane protons) 6.45 s OH 1.2 to 2.2 massive COO—cyclohexyl |
| 770 203 | oxygen | benzodioxane—CONH₂ | C₉H₉NO₄ | 195.17 | 220 | 97.5 | NMR (DMSO) 7.45,d(J=10Hz); δppm 6.5,d(J=10Hz) & 4.38,s (6 benzodioxane protons) 7.4,s CONH₂ |
| 770 829 | oxygen | benzodioxane—CONH—cyclohexyl | C₁₅H₁₉NO₄ | 277.310 | 182 | 92 | NMR (DMSO) 7.31,D(J=10Hz); δppm 6.45,d(J=10Hz) & 4.39,s (6 benzodioxane protons) 10.0 s (OH) 7.6,d & 1.0 to 2.0 massive CONH—cyclohexyl |
| 770 850 | oxygen | benzodioxane—CONH—phenyl | C₁₅H₁₃NO₄ | 271.262 | 163 | 100 | NMR (DMSO) 7.4,m & 6.45d δ ppm (aromatic protons) 4.35 m (4 dioxane protons) 9.83 s (OH) |
| 770 543 | oxygen | benzodioxane—NH—COEt | C₁₁H₁₃NO₄ | 223.222 | 190 | 90 | NMR (DMSO) 7.08,d(J=10Hz); δ ppm 6.3,d(J=10Hz) & 4.24,s (6 benzodioxane protons) 9.3,s & 8.9 s OH & NH 2.32q(J=7Hz) & 1.09,d (J=7Hz) CO Et |

TABLE V-continued

| Code Number | X' | —Ar' (H—X'—Ar') | Empirical Formula (VII) | Molecular Weight | Melting Point °C. | Yield % | IR or NMR spectrum or elementary analysis |
|---|---|---|---|---|---|---|---|
| 770 608 | oxygen | benzodioxane-NH—CO—C$_3$H$_7$ (n) | C$_{12}$H$_{15}$NO$_4$ | 237.248 | 118 | 94 | NMR (DMSO) 7.1,d(J=10Hz); δ ppm 6.3,d(J=10Hz) & 4.2,s (6 benzodioxane protons) 9.0 s & 8.8 s OH & NH 2.3 m; 1.4 m & 0.92,t (J=6Hz) COC$_3$H$_7$n |
| 770 599 | oxygen | benzodioxane-NHCOC$_4$H$_9$ (n) | C$_{13}$H$_{17}$NO$_4$ | 251.284 | 80 | 100 | NMR (DMSO) 7.15,d(J=10Hz); δ ppm 6.35,d(J=10Hz) & 4.2 s (6 benzodioxane protons) 9.0 s OH & NH 2.35 m; 0.8 to 1.8 massive COC$_4$H$_9$n |
| 770 690 | oxygen | benzodioxane-NH—CO—iPr | C$_{12}$H$_{15}$NO$_4$ | 237.248 | 55 | 100 | NMR (DMSO) 7.1,d(J=10Hz); δ ppm 6.32,d(J=10Hz) & 4.2,s (6 benzodioxane protons) 9.1,s & 8.7,s OH & NH 2.65,m & 1.05,d (J=7Hz) CO—iPr |
| 770 612 | oxygen | benzodioxane-NH—CO+ | C$_{13}$H$_{17}$NO$_4$ | 251.284 | 54 | 90 | NMR (DMSO) 7.02,d(J=10Hz); δ ppm 6.35,d(J=10Hz) & 4.22,s (6 benzodioxane protons) 9.7 s & 8.2,s OH & NH 1.20,s CO+ |
| 770 531 | oxygen | benzodioxane-NH—CO—cyclohexyl | C$_{15}$H$_{19}$NO$_4$ | 277.31 | 68 | 100 | NMR (DMSO) 7.12,d(J=10Hz); δ ppm 6.35,d(J=10Hz) & 4.21,s (6 benzodioxane protons) 9.0 s & 8.7,s OH & NH 1.0 to 2.0, massive CO—cyclohexyl |
| 770 527 | oxygen | benzodioxane-NH—CO—phenyl | C$_{15}$H$_{13}$NO$_4$ | 271.262 | 84 | 95 | NMR (DMSO) 6.95,d(J=10Hz); δ ppm 6.42,d(J=10Hz) 4.23,s (6 benzodioxane protons) 10.6,s & 9.65,s OH & NH 7.95,m & 7.5 m CO—phenyl |
| 770 305 | oxygen | benzodioxane-NH—CONH—Et | C$_{11}$H$_{14}$N$_2$O$_4$ | 238.238 | 170 | 98 | NMR (DMSO) 7.3,d(J=10Hz); δ ppm 6.32,d(J=10Hz) & 4.25,s (6 benzodioxane protons) 8.7,s (OH) 7.45,s; 6.55,m, 3.1,m & 1.05,t (J=7Hz) NHCONH Et |
| 770 481 | oxygen | benzodioxane-NHCONHC$_3$H$_7$ (n) | C$_{12}$H$_{16}$N$_2$O$_4$ | 252.264 | 186 | 85 | NMR (DMSO) 7.3,d(J=10Hz); δ ppm 6.3,d(J=10Hz) & 4.21,s (6 benzodioxane protons) 8.83,s (OH) 7.5,s; 6.55,m; 3.05m & 1.1,m NHCONHC$_3$H$_7$n |
| 770 628 | oxygen | benzodioxane-NHCONH—iPr | C$_{12}$H$_{16}$N$_2$O$_4$ | 252.264 | 189 | 77 | NMR (DMSO) 7.3,d(J=10Hz); δ ppm 6.3,d(J=10Hz) & 4.22,s (6 benzodioxane protons) 8.7,s (OH) 7.4,s; 6.42, m; 3.75m & 1.1,d(J=7Hz) NHCONH—iPr |
| 770 632 | oxygen | benzodioxane-NHCONHC$_4$H$_9$ (n) | C$_{18}$H$_{18}$N$_2$O$_4$ | 266.290 | 195 | 98 | NMR (DMSO) 7.32,d(J=10Hz); δ ppm 6.28,d(J=10Hz) & 4.25,s (6 benzodioxane protons) 9.1,s (OH) 7.42,s; 6.52,s 3.05,m; 1.38,m & 0.9,m NHCONHC$_4$H$_9$n |
| 770 709 | oxygen | benzodioxane-NHCONH+ | C$_{18}$H$_{18}$N$_2$O$_4$ | 266.290 | 199 | 99 | NMR (DMSO) 7.32,d(J=10Hz); δ ppm 6.3,d(J=10Hz) & 4.23,s (6 benzodioxane protons) 7.4,s; 6.5,s & 1.27,s NHCONH+ |
| 780 221 | oxygen | | C$_{16}$H$_{16}$N$_2$O$_5$ | 316.304 | 232 | 87 | Elementary analysis C H N |

TABLE V-continued

| Code Number | X' | —Ar' | Empirical Formula H—X'—Ar' (VII) | Molecular Weight | Melting Point °C. | Yield % | IR or NMR spectrum or elementary analysis |
|---|---|---|---|---|---|---|---|
| | | benzodioxane-NHCONH-C₆H₄-OCH₃ | | | | | Calc. % 60.75 5.10 8.86<br>Obt. % 60.65 5.17 8.61 |
| 771 231 | oxygen | benzodioxane-NHCON(CH₃)₂ | $C_{11}H_{14}N_2O_4$ | 238.238 | 176 | 75 | Elementary analysis<br>      C    H    N<br>Cal. % 55.45 5.92 11.76<br>Obt. % 55.61 5.75 11.84 |
| 771 147 | oxygen | benzodioxane-NHCON(morpholine) | $C_{13}H_{16}N_2O_5$ | 280.274 | 172–4 | 83 | NMR (CDCl₃) 7.38,d(J=10Hz);<br>δ ppm 6.48,d(J=10Hz) & 4.32,s<br>(6 benzodioxane protons)<br>7.3,s & 6.5,s OH & NH<br>3.75,m & 3.5,m —N(morpholine) |
| 771 236 | oxygen | benzodioxane-N(CH₃)CONHCH₃ | $C_{11}H_{14}N_2O_4$ | 238.238 | 235 | 70 | Elementary analysis<br>      C    H    N<br>Calc. (%) 55.45 5.92 11.76<br>Obt. (%) 55.41 6.28 11.82 |
| 770 310 | oxygen | benzodioxane-CH₂COOEt | $C_{12}H_{14}O_5$ | 238.232 | oil | 98 | NMR (CDCl₃) 6.65,d(J=10Hz);<br>δ ppm 6.40,d(J=10Hz) & 4.20,s<br>(6 benzodioxane protons)<br>7.32,s (OH)4.18,q (J=<br>6Hz); 3.51,s & 1.12,t<br>(J=6Hz) CH₂ CO₂ Et |
| 770 384 | oxygen | benzodioxane-CH₂CONH₂ | $C_{10}H_{11}NO_4$ | 209.196 | 190 | 95 | NMR (DMSO) 6.52,d(J=10Hz);<br>δ ppm 6.3,d(J=10Hz) & 4.18,s<br>(6 benzodioxane protons)<br>6.65 to 7.2 massive<br>CONH₂ 3.20,s - CH₂CO |
| 770 380 | oxygen | benzodioxane-CH₂CONHCH₃ | $C_{11}H_{13}NO_4$ | 223.222 | 170-5 | 98 | NMR (DMSO) 6.6,d(J=10Hz);<br>δ ppm 6.35,d(J=10Hz) & 4.22,s<br>(6 benzodioxane protons)<br>8.15,s & 7.55 m OH&NH<br>3.3,s CH₂CO<br>2.6,d(J=5Hz) CONHCH₃ |
| 780 306 | oxygen | benzodioxole-COCH₃ | $C_9H_8O_4$ | 180.184 | 191 | 100 | Elementary analysis<br>      C    H<br>Calc. (%) 60.00 4.48<br>Obt. (%) 60.30 4.66 |
| 780 344 | oxygen | benzodioxole-NHCOCH₃ | $C_9H_9NO_4$ | 195.170 | 212 | 100 | Elementary analysis<br>      C    H    N<br>Calc. (%) 55.38 4.65 7.18<br>Obt. (%) 55.17 4.47 7.10 |
| 780 407 | oxygen | benzodioxole-NHCONHCH₃ | $C_9H_{10}N_2O_4$ | 210.186 | 236 | 92.5 | Elementary analysis<br>      C    H    N<br>Calc. (%) 51.43 4.79 13.33<br>Obt. (%) 51.19 4.65 13.40 |
| 780 239 | oxygen | | $C_{11}H_{12}O_4$ | 208.206 | 121 | 43 | Elementary analysis<br>      C    H |

TABLE V-continued

| Code Number | X' | —Ar' | H—X'—Ar' Empirical Formula | (VII) Molecular Weight | Melting Point °C. | Yield % | IR or NMR spectrum or elementary analysis |
|---|---|---|---|---|---|---|---|
| | | —⟨benzodioxepine⟩—COCH₃ | | | | | Calc. (%) 63.45 5.81<br>Obt. (%) 63.54 5.89 |
| 780 391 | oxygen | —⟨benzodioxepine⟩—NHCOCH₃ | C₁₁H₁₃NO₄ | 223.222 | 177 | 51 | NMR (DMSO) 7.32,d(J=10Hz);<br>δ ppm 6.43,d(J=10Hz) 4.05,m &<br>2.105,m (8 benzodioxepine protons) 8.15,b; &<br>7.3,b OH & NH 2.05,s COCH₃ |
| 780 466 | oxygen | —⟨benzodioxepine⟩—NHCONHCH₃ | C₁₁H₁₄N₂O₄ | 238.228 | 182 | 95 | NMR (DMSO) 7.5,d(J=10Hz);<br>δ ppm 6.45,d(J=10Hz) 4.05,m &<br>2.1m (8 benzodioxepine protons) 8.3,b; 7.63,s<br>& 6.55,m OH & NHCONH<br>2.65,d(J=4Hz) CH₃ |
| 760 697 | oxygen | —⟨benzodioxane⟩—COOEt | C₁₁H₁₂O₅ | 224.206 | | 100 | δ ppm =7.40; 6.50; d; (J=10Hz)<br>& 4.28,s benzodioxane protons<br>=6.35m; —OH<br>=4.31,q,&1.34,t,(J=8Hz): COOEt<br>IR: bands at 1710 & 1200 cm−1 (COOEt |
| 770 075 | oxygen | —⟨benzodioxane⟩—NHCONH—CH₃ | C₁₀H₁₂N₂O₄ | 224.212 | 218 | 85 | δ ppm=7.30; 6.30; d,(J=10Hz);<br>4.22,s,: benzodioxane protons<br>=7.60,s,&6.43,d(J=5Hz):<br>—NHCONH—<br>=2.60,d,(J=5Hz): —CH₃ |
| 770 079 | oxygen | —⟨benzodioxane⟩—NHCONH—⟨cyclohexyl⟩ | C₁₅H₂₀N₂O₄ | 292.326 | 235 | 90 | δ ppm=7.32, 6.38; d,(J=10Hz);<br>4.30,s: benzodioxane protons<br>=7.43,s,&6.52,d,(J=5Hz):<br>—NH—CO—NH—<br><br>=1.5,m,—⟨cyclohexyl⟩ |
| 770 083 | oxygen | —⟨benzodioxane⟩—NHCONH—⟨phenyl⟩ | C₁₅H₁₅N₂O₄ | 286.27 | 215 | 93 | δ ppm=7.32; & 6.38; d,(J=10 Hz); 4.32,s,: benzodioxane protons<br>=9.01,s,&7.82,s,—NH—CO—NH—<br><br>=7.6 a 6.8,m,:—⟨phenyl⟩ |
| 760 702 | oxygen | —⟨benzodioxane⟩—CH₂OH | C₉H₁₁O₄ | 182.17 | 136 | 96.5 | δ ppm=6.72,6.50,d,(J=10Hz);<br>4.20s: benzodioxane protons<br>=4.38,s,: —CH₂—OH<br>=5.50,m,: —OH |
| 770 185 | oxygen | —⟨benzodioxane⟩—CH₂—CN | C₁₀H₁₀NO₃ | 191.180 | oil | 94 | δ ppm=6.72,6.52d,(J=10Hz),<br>4.23,s,: benzodioxane protons<br>=3.45,s,—CH₂—CN |

TABLE VI (XI): R''₇ = R''₈ = H

| Code No. | p | —R''₉ | | Empirical Formula | Molecular Weight | Melting Point °C. | Yield % | IR or NRM spectrum or elementary analysis |
|---|---|---|---|---|---|---|---|---|
| 780 366 | 2 | —COO+ | XI$_c$ | C$_{20}$H$_{22}$O$_5$ | 342.376 | 90 | 58 | NMR (CDCl$_3$) δ ppm = 7.35,d (J = 10Hz) 6.48,d(J = 10Hz) & 4.35,s (6 benzodioxane protons) 7.38,s & 5.18,s O—CH$_2$—⌬ 1.55,s COO+ |
| 780 298 | 2 | —COO—C$_5$H$_{11}$(n) | XI$_c$ | C$_{21}$H$_{24}$O$_5$ | 356.402 | 50 | 94 | NMR (CDCl$_3$) δ ppm = 7.35,d (J = 10Hz); 6.45,d(J = 10Hz) & 4.27,s (6 benzodioxane protons) 7.38,s & 5.12,s O—CH$_2$—⌬ 0.8 – 1.9, massive COOC$_5$H$_{11}$n |
| 780 330 | 2 | —COO—⌬ | XI$_c$ | C$_{22}$H$_{24}$O$_5$ | 368.412 | 102 | 58 | NMR (CDCl$_3$) δ ppm = 7.35,d (J = 10Hz); 6.45,d(J = 10Hz) & 4.3,s (6 benzodioxane protons) 7.32,s & 5.15,s O—CH$_2$—⌬ |
| 770 202 | 2 | —CONH$_2$ | XI$_d$ | C$_{16}$H$_{15}$NO$_4$ | 285.288 | 136 | 92 | Elementary analysis<br>C H N<br>Cal. % 67.36 5.30 4.91<br>Obt. % 67.13 5.37 4.76 |
| 770 849 | 2 | —CONH—⌬ | XI$_d$ | C$_{22}$H$_{19}$NO$_4$ | 361.38 | 196 | 84 | NMR (DMSO) δ ppm = 7.0 – 7.9, massive; 6.8,d (J = 10Hz) (11 aromatic protons) 5.1, s (OCH$_2^-$); 4.4,s (4 dioxane protons) 8.7,s. NH |
| 770 598 | 2 | —NH—CO—C$_4$—H$_9$(n) | XI$_e$ | C$_{20}$H$_{23}$NO$_4$ | 341.392 | 157 | 72 | (J = 10Hz); 6.47, d(10Hz) & 4.26, s (6 benzodioxane protons) 7.38, s & 5.08, s O—CH$_2$—⌬ 2.35, m; 0.8 to 2.0, massive COC$_4$H$_9$(n) |
| 770 689 | 2 | —NH—CO—⟨ | XI$_e$ | C$_{19}$H$_{21}$NO$_4$ | 327.366 | 155 | 74 | NMR(CDCl$_3$)δppm = 7.8, d(J = 10 Hz); 6.5, d (J = 10Hz) & 4.25 s (6 benzodioxane protons) 7.35,s & 5.08,s O—CH$_2$—⌬ 2.5,m & 1.07,d (J = 6Hz) CO—⟨ 7.7,s NH |
| 770 530 | 2 | —NH—CO—⌬ | XI$_e$ | C$_{22}$H$_{25}$NO$_4$ | 367.43 | 145 | 70 | NMR (CDCl$_3$)δppm = 7.82,d(J = 10 Hz); 6.50,Hz); 6.50,d(J = 10Hz) & 4.3 s (6 benzodioxane protons) 7.38,s & 4.10 s O—CH$_2$—⌬ 1.2, to 2.4, massive CO—⌬ |
| 770 526 | 2 | —NH—CO—⌬ | XI$_e$ | C$_{22}$H$_{19}$NO$_4$ | 361.38 | 155 | 96 | NMR(CDCl$_3$)δppm = 7.9,m; 7.4m & 6.52,d(J d(J = 10Hz) (aromatic protons) 5.08,s O—CH$_2$ 4.22 s dioxane protons 8.20 s NH |
| 770 607 | 2 | —NH—COC$_3$H$_7$n | XI$_e$ | C$_{19}$H$_{21}$NO$_4$ | 327.366 | 134.5 | 70 | NMR(CDCl$_3$)δppm = 7.75,d (J = 10Hz) 6.47,d(J d(J = 10Hz) & 4.22,s (6 benzodioxane protons) 7.35 s & 5.08 s: O—CH$_2$⌬ 2.25, m; 1.70 m & 0.98, t(J = 6Hz) COC$_3$H$_7$n) |
| 770 074 | 2 | —NHCONH—CH$_3$ | XI$_f$ | C$_{17}$H$_{18}$N$_2$O$_4$ | 314.330 | 220 | 98 | δppm = 7.30,d; 7.52,d; (J = |

TABLE VI-continued (XI): $R''_7 = R''_8 = H$

| Code No. | p | $-R''_9$ | Empirical Formula | Molecular Weight | Melting Point °C. | Yield % | IR or NRM spectrum or elementary analysis |
|---|---|---|---|---|---|---|---|
| | | | | | | | 10Hz) & 4.20,s;(benzodiozane protons) = 7.64,s; 7.50,m; NH—CONH = 7.20,s & 5.00,s: O—CH$_2$—C$_6$H$_5$ |
| 780 220 | 2 | —NHCONH—C$_6$H$_4$—OCH$_3$ | XI$_f$ C$_{23}$H$_{22}$N$_2$O$_5$ | 406.422 | 240 | 89 | NMR(DMSO)δppm = 7.4 m; 6.7, m (aromatic protons) 5.0s: O—CH$_2$; 4.3,s dioxane proton)3.7,s: O—CH$_3$ 8.8 s; 8.0 s NHCONH |
| 780 406 | 1 | —NHCONHCH$_3$ | XI$_f$ C$_{16}$H$_{16}$N$_2$O$_4$ | 300.304 | 200 | 100 | (DMSO) δppm=7.25,d(J=10Hz); 6.55,d(J = 10Hz) & 5.95,s (4 benzodioxol protons) 7.40,s & 5.10,s O—CH$_2$—C$_6$H$_5$ 7.8,s & 6.15, m NHCONH 2.65,d(J = 5Hz) —CH$_3$ |
| 780 238 | 3 | —COCH$_3$ | XI$_i$ C$_{18}$H$_{18}$O$_4$ | 298.324 | 78 | 43 | Elementary analysis: C H Cal.(%) 72.46 6.08 Obt.(%) 72.33 6.15 |
| 780 463 | 3 | —NHCOCH$_3$ | XI$_h$ C$_{18}$H$_{19}$NO$_4$ | 313.340 | 142 | 52 | NMR(DMSO ppm = 7.38,s; 6.66, d(J = 10Hz) (aromatic protons 5.0 O—CH$_2$ 4.05,m & 2.0,s O—(CH$_2$)$_3$—O & COCH$_3$ 9.1,s NH |
| 780 465 | 3 | —NHCONHCH$_3$ | XI$_f$ C$_{18}$H$_{20}$N$_2$O$_4$ | 328.346 | 140 | 78 | Elementary analysis C H N Cal.(%) 65.84 6.14 8.53 Obt.(%) 65.54 6.10 8.23 |
| 770 611 | 2 | —NH—CO+ | XI$_c$ C$_{20}$H$_{23}$NO$_4$ | 341.392 | 113 | 73 | NMR(CDCl$_3$)δppm = 7.8,d(J = 10Hz) 6.5 d(J = 10Hz) & 4.3 s (6 benzodioxane protons) 7.4,s & 5.1 s O—CH$_2$—C$_6$H$_5$ 1.3,s CO+ |
| 770 480 | 2 | —NHCONHC$_3$H$_{7n}$ | XI$_f$ C$_{19}$H$_{22}$N$_2$O$_4$ | 342.382 | 180 | 75 | Elementary analysis C H N Cal.(%) 66.65 6.48 8.18 Obt.(%) 66.28 6.49 8.27 |
| 770 627 | 2 | —NH—CO—NH—CH(CH$_3$)$_2$ | XI$_f$ C$_{19}$H$_{22}$N$_2$O$_4$ | 342.382 | 182-4 | 80 | NMR(DMSO)δppm = 7.35,d(J = 10Hz); 6.34,d(J = 10Hz) & 4.28 s (6 benzodioxane protons) 7.45,s; 5.05,s OCH$_2$—C$_6$H$_5$ 7.8,s; 6.65 m; 3.8 m; 1.1 d (J = 7Hz) NHCONH—CH(CH$_3$)$_2$ |

The compounds of formula I were studied on laboratory animals and showed an antiangorous activity, as well as activities on the peripheral and cerebral circulation.

Antiangorous activity

The antiangorous activity was tested on an anaesthetized dog (sodium pentobarbital 30 mg/kg/i.v.).

The consumption of oxygen in the left ventricule was estimated by the product of the coronary venous flow and the coronary arteriovenous difference in oxygen (% volume).

The coronary venous flow was measured at the coronary venous sinus by means of a modified Morawitz cannula, introduced under radioscopic control.

The arterial and coronary venous oxygenation was measured with a blood gas analyzer (IL meter 213).

The cardiac effort was estimated according to KATZ's index, by the product of the average arterial pressure and the cardiac frequency.

The cardiac frequency was estimated from the electrocardiogram recorded with $D_2$ derivation.

The systemic arterial pressure was measured at the femoral artery with a pressure sensor (SANBORN 267-BC).

The results obtained by injecting the compounds of formula I and the following reference products: LIDOFLAZINE and AMIODARONE, are given in Table VII below. It should be noted that the compounds tested were injected intravenously with slow perfusion.

TABLE VII

| Tested Compound Code No. | Toxicity* (Mortality) (mg/kg/i.v.) | $O_2$ Dose (mg/kg/i.v.) | Diminution in consumption of effort (IK) in % | in time (in min.) | Diminution in the cardiac in % | in time (in min.) |
|---|---|---|---|---|---|---|
| 760 382 | 260 | 2.5 | 40 | 30 | 24 | 30 |
| 760 385 | 351 (10%) | 2.2 | 65 | 15 | 16 | 15 |
| 760 389 | 245 | 4.5 | 70 | 60 | 55 | 60 |
| 760 390 | 227 | 9.1 | 64 | 53 | 60 | 45 |
| 760 392 | — | 2.5 | 31 | 30 | 11 | 30 |
| 760 393 | 319 | 2.5 | 47 | 15 | 5 | 15 |
| 760 394 | 214 | 2.1 | 60 | 60 | 46 | 45 |
| 760 455 | 255 (50%) | 2.5 | 45 | 15 | 24 | 30 |
| 760 476 | 185 | 2.3 | 70 | 23 | 5 | 15 |
| 760 501 | — | 2.3 | 75 | 45 | 4 | 15 |
| 760 506 | 182 | 2.3 | 67 | 60 | 26 | 60 |
| 760 507 | 185 | 4.6 | 68 | 60 | 32 | 30 |
| 760 519 | 218 | 2.5 | 51 | 15 | 11 | 15 |
| 760 520 | 157 | 2.3 | 45 | 40 | 13 | 30 |
| 760 529 | 115 | 2.3 | 53 | 30 | 19 | 15 |
| 760 538 | 185 (10%) | 2.3 | 48 | 15 | 37 | 30 |
| 760 542 | 400 (0%) | 2.5 | 64 | 45 | 32 | 50 |
| 760 580 | 294 | 2.3 | 19 | 30 | 26 | 15 |
| 760 619 | 158 | 2.3 | 55 | 30 | 44 | 30 |
| 760 620 | 285 | 2.5 | 22 | 30 | 10 | 30 |
| 760 700 | 367 (0%) | 0.6 | 59 | 45 | 47 | 60 |
| 760 705 | 400 (20%) | 1.25 | 51 | 38 | 26 | 75 |
| 760 710 | 345 (70%) | 0.54 | 64 | 60 | 36 | 30 |
| 760 781 | 377 (0%) | 2.4 | 70 | 90 | 15 | 45 |
| 760 784 | 372 | 2.3 | 44 | 30 | 12 | 30 |
| 760 847 | 169 (20%) | 2.5 | 47 | 60 | 14 | — |
| 760 852 | — | 2.5 | 44 | 30 | 23 | 45 |
| 760 866 | 360 (30%) | 0.6 | 54 | 30 | 20 | 30 |
| 760 868 | 215 (40%) | 0.12 | 33 | 30 | 18 | 30 |
| 760 892 | 400 (40%) | 2.5 | 74 | 60 | 22 | 45 |
| 760 939 | 400 (20%) | 1.25 | 27 | 30 | 11 | 23 |
| 760 986 | 218 | 2.5 | 61 | 60 | 27 | 60 |
| 770 056 | 160 | 0.625 | 49 | 15 | 22 | 15 |
| 770 058 | 315 | 2.5 | 36 | 30 | 35 | 30 |
| 770 059 | 91 | 5 | 64 | 15 | 12 | 15 |
| 770 060 | 195 | 2.3 | 58 | 23 | 35 | 30 |
| 770 073 | 158 | 0.12 | 24 | 30 | 16 | 15 |
| 770 077 | 400 (0%) | 0.15 | 44 | 20 | 28 | 30 |
| 770 081 | 148 | 0.14 | 58 | 53 | 20 | 15 |
| 770 085 | p.o.: 1855 (0%) | 0.15 | 44 | 60 | 14 | 60 |
| 770 112 | 224 | 2.3 | 34 | 23 | 7 | 15 |
| 770 135 | 400 (0%) | 1.25 | 40 | 30 | 28 | 30 |
| 770 142 | 116 | 1.1 | 29 | 30 | — | — |
| 770 188 | 219 | 2.5 | | | | |
| 770 199 | 328 | 1.02 | 29 | 15 | 5 | 15 |
| 770 274 | 336 (30%) | 2.5 | 41 | 30 | 10 | 15 |
| 770 276 | 248 | 2.5 | 59 | 23 | — | — |
| 770 307 | 367 (10%) | 0.15 | 43 | 30 | 11 | 30 |
| 770 312 | 259 | 0.14 | 30 | 30 | 9 | — |
| 770 382 | 400 (30%) | 0.625 | 36 | 15 | 16 | 15 |
| 770 386 | 400 (20%) | 0.625 | 41 | 30 | 20 | 30 |
| 770 458 | 250 | 2.5 | 72 | 23 | 25 | 15 |
| 770 483 | p.o.: 2000 (0%) | 0.15 | 74 | 45 | 16 | 30 |
| 770 487 | 400 (30%) | 2.5 | 47 | 60 | 14 | — |
| 770 488 | 225 | 2.5 | 78 | 30 | 17 | 15 |
| 770 495 | 175 | 2.5 | 74 | 45 | 43 | 30 |
| 770 504 | 145 | 2.5 | 52 | 15 | 10 | — |
| 770 525 | 325 | 0.625 | 66 | 60 | 43 | 60 |
| 770 529 | p.o.: 2000 (22%) | 0.625 | 56 | 30 | 29 | 30 |
| 770 533 | p.o.: 2000 (10%) | 0.625 | 30 | 25 | 28 | 25 |
| 770 538 | 198 | 2.5 | 54 | 15 | 28 | 25 |
| 770 545 | 400 (40%) | 0.625 | 61 | 30 | 16 | 15 |

TABLE VII-continued

| Tested Compound Code No. | Toxicity* (Mortality) (mg/kg/i.v.) | O₂ Dose (mg/kg/i.v.) | Diminution in consumption of effort (IK) in % | in time (in min.) | Diminution in the cardiac in % | in time (in min.) |
|---|---|---|---|---|---|---|
| 770 585 | p.o.: 2000 (0%) | 2.5 | 75 | 30 | 41 | 30 |
| 770 590 | 290 | 2.5 | 60 | 45 | 33 | 45 |
| 770 601 | p.o.: 2000 (22%) | 0.625 | 69 | 30 | 25 | 30 |
| 770 610 | p.o.: 2000 (0%) | 0.625 | 56 | 60 | 34 | 45 |
| 770 614 | p.o.: 2000 (11%) | 0.625 | 49 | 30 | 45 | 30 |
| 760 622 | 400 (40%) | 1.25 | 20 | 30 | 17 | 15 |
| 770 630 | 400 (40%) | 0.15 | 58 | 60 | 32 | 60 |
| 770 634 | 400 (30%) | 0.15 | 69 | 30 | 27 | 30 |
| 770 692 | 200 (60%) | 0.625 | 60 | 15 | 45 | 30 |
| 770 727 | 130 | 2.5 | 57 | 15 | 27 | 30 |
| 770 738 | 400 (40%) | 2.5 | 63 | 45 | 48 | 45 |
| 770 831 | p.o.: 2000 (0%) | 1.25 | 45 | 30 | 27 | 45 |
| 770 844 | 400 (0%) | 2.5 | 58 | 23 | 35 | 30 |
| 770 848 | 400 (10%) | 0.15 | 41 | 30 | 5 | — |
| 770 854 | 300 (20%) | 2.5 | 41 | 40 | 18 | 40 |
| 770 855 | 260 | 2.5 | 60 | 60 | 45 | 60 |
| 770 858 | 260 | 0.15 | 16 | 30 | 15 | 30 |
| 770 859 | 150 | 2.5 | 30 | 30 | 52 | 60 |
| 770 898 | 400 (0%) | 2.5 | 45 | 45 | 36 | 38 |
| 770 963 | 190 | 2.5 | 58 | 30 | 66 | 30 |
| 770 966 | — | 2.5 | 7 | — | 46 | 30 |
| 770 992 | 400 (0%) | 2.5 | 77 | 40 | 36 | 30 |
| 770 993 | 10 — | 2.5 | 53 | 23 | 15 | 13 |
| 771 014 | 140 | 2.5 | 66 | 30 | 11 | 15 |
| 771 031 | — | 0.15 | 20 | 30 | 25 | 30 |
| 771 036 | — | 2.5 | 15 | — | 25 | 15 |
| 771 076 | 400 (0%) | 2.5 | 16 | 15 | 22 | 30 |
| 771 077 | 400 (10%) | 2.5 | 61 | 45 | 39 | 30 |
| 771 124 | 270 | 2.5 | 34 | 15 | 13 | 23 |
| 771 149 | — | 0.15 | 12 | 30 | 14 | 30 |
| 771 153 | — | 2.5 | 31 | 23 | 63 | 40 |
| 771 157 | 210 | 2.5 | 53 | 30 | 46 | 30 |
| 771 163 | — | 0.625 | 61 | 30 | 20 | 40 |
| 771 172 | — | 2.5 | 25 | 15 | 29 | 23 |
| 771 233 | 310 | 0.15 | 29 | 15 | 9 | 15 |
| 771 238 | 400 (0%) | 1.25 | 40 | 30 | 38 | 30 |
| 771 281 | — | 2.5 | 23 | 30 | 44 | 30 |
| 771 306 | — | 1.25 | 58 | 15 | 38 | 30 |
| 771 309 | — | 2.5 | 63 | 45 | 31 | 15 |
| 771 315 | — | 1.25 | 11 | — | 29 | 15 |
| 771 318 | — | 2.5 | 63 | 60 | 31 | 15 |
| 771 348 | — | 2.5 | 59 | 30 | 42 | 30 |
| 780 004 | 400 (10%) | 1.25 | 22 | 30 | 14 | 15 |
| 780 009 | — | 1.25 | 48 | 35 | 20 | 30 |
| 780 040 | 400 (30%) | 2.5 | 59 | 15 | 9 | — |
| 780 044 | 400 (10%) | 2.5 | 49 | 30 | 36 | 15 |
| 780 120 | 340 | 2.5 | 65 | 30 | 29 | 15 |
| 780 128 | — | 2.5 | 57 | 23 | 17 | 23 |
| 780 138 | 150 | 2.5 | 46 | 45 | 19 | 30 |
| 780 150 | 162 | 2.5 | 54 | 45 | 19 | 15 |
| 780 189 | — | 2.5 | 63 | 30 | 30 | 45 |
| 780 223 | — | 2.5 | 62 | 90 | 35 | 90 |
| 780 269 | — | 2.5 | 34 | 30 | 40 | 60 |
| 780 272 | — | 2.5 | 40 | 90 | 51 | 90 |
| 780 292 | — | 2.5 | 59 | 90 | 34 | 45 |
| 780 301 | — | 0.15 | 40 | 30 | 28 | 60 |
| 780 333 | — | 0.15 | 51 | 30 | 21 | 23 |
| 780 339 | — | 2.5 | 74 | 45 | 42 | 40 |
| 780 369 | — | 0.625 | 37 | 15 | 4 | 15 |
| 780 373 | — | 2.5 | 66 | 30 | 25 | 30 |
| 780 374 | — | 2.5 | 39 | 30 | 31 | 15 |
| 780 384 | — | 0.15 | 43 | 30 | 25 | 40 |
| 780 389 | — | 2.5 | 32 | 15 | 15 | 30 |
| 770 545 | 400 (40%) | 0.625 | 61 | 30 | 16 | 15 |
| 770 771 | p.o.: 2000 (0%) | po 12.5 | — | — | 32 | — |
| 780 225 | — | 2.5 | 36 | 30 | 22 | 30 |
| 780 241 | — | 0.15 | 30 | 23 | 13 | 23 |
| 780 267 | — | 2.5 | 27 | 30 | 8 | — |
| 780 302 | — | 2.5 | 46 | 30 | 14 | 30 |
| 780 308 | 400 (10%) | 2.5 | 49 | 45 | 37 | 45 |
| 780 329 | — | 2.5 | 21 | 30 | 13 | 30 |
| 780 346 | — | 0.15 | 43 | 30 | 2 | — |
| 780 353 | — | 2.5 | 46 | 15 | 16 | 15 |
| 780 357 | — | 2.5 | 43 | 15 | 21 | 15 |
| 780 359 | — | 0.625 | 60 | 45 | 32 | 30 |
| 780 361 | — | 2.5 | 68 | 30 | 38 | 45 |
| 780 393 | 400 (10%) | 0.625 | 24 | 30 | 45 | 30 |

TABLE VII-continued

| Tested Compound Code No. | Toxicity* (Mortality) (mg/kg/i.v.) | O₂ Dose (mg/kg/i.v.) | Diminution in consumption of effort (IK) in % | Diminution in consumption of effort (IK) in time (in min.) | Diminution in the cardiac in % | Diminution in the cardiac in time (in min.) |
|---|---|---|---|---|---|---|
| 780 401 | — | 2.5 | 64 | 30 | 6 | — |
| 780 409 | 400 (20%) | 2.5 | 54 | 90 | 43 | 90 |
| 780 415 | 305 | 2.5 | 29 | 30 | 10 | 30 |
| 780 456 | — | 0.625 | 13 | 15 | 32 | 30 |
| 780 404 | — | 2.5 | 69 | 15 | 44 | 30 |
| LIDOFLAZINE | 25 (50%) | 1.5 | 48 | 30 | 40 | 15 |
| AMIODARONE | 180 (50%) | 10 | 11 | 15 | 22 | 15 |

*LD₅₀ or percentage of mortality which is given between brackets

Activity on the cerebral circulation

The activity on the cerebral circulation was tested on an anaesthetized dog (sodium pentobarbital 30 mg/kg/i.v.). The vertebral artery flow was measured by means of an electromagnetic perivascular or ultrasonic Doppler effect probe.

The intracerebral vascular resistance was estimated by the back pressure of the internal carotid artery.

The systemic arterial pressure was measured at the femoral artery with a pressure sensor (SANBORN 267-BC).

The increase in the extraction of cerebral oxygen was estimated by the following equation:$(A-V)/A$ in which:

A represents the volume of oxygen in the arterial blood (% volume) measured by hemoreflectometry (KIPP and ZONEN's apparatus) and quantity determination of the haemoglobin (DRABKIN's method).

V represents the volume of oxygen in the cerebral venous blood (internal maxillary vein).

The results obtained by injecting the compounds of formula I and the following reference compounds: papaverine, naphtidrofuryl, and cinnarizine are given in Table VIII below.

It should be noted that the compounds tested were injected intravenously (rapid injection).

TABLE VIII

| Compound Tested Code No. | Dose mg/kg/i.v. | Vertebral artery flow in % | Vertebral artery flow in time (min) | Internal carotid artery back pressure in % | Internal carotid artery back pressure in time (min) | Systemic average arterial pressure in % | Systemic average arterial pressure in time | Increase of the extraction of cerebral oxygen in % |
|---|---|---|---|---|---|---|---|---|
| 760 392 | 2 | +186 | <30 | −79 | >30 | −39 | 30 | — |
| 760 390 | 5 | +177 | 30 | −22 | 5 | −13 | <10 | — |
| 760 393 | 5 | +150 | <2 | −62 | 10 < <50 | −33 | 30 | — |
| 760 455 | 5 | +120 | 6 | −90 | 20 | −39 | 30 | — |
| 770 458 | 2,5 | — | — | −11 | 15 | −10 | 15 | +35 |
| 770 495 | 2,5 | + 60 | 60 | −17 | 60 | −20 | 20 | +188 |
| 760 518 | 5 | +180 | 5 | −48 | 5 | −15 | 5 | — |
| 760 505 | 5 | +113 | 10 | −38 | 10 | −11 | 20 | — |
| 760 388 | 5 | +225 | 50 | −65 | 50 | −44 | 50 | — |
| Papaverine | 2,5 | +100 | 6 | −45 | 5 | — | — | 0 |
| Naphtidrofuryl | 2,5 | +100 | 5 | −26 | 5 | −50 | 2 | −50 |
| Cinnarizine | 5 | +130 | 30 | −25 | 30 | −20 | 15 | 0 |

Activity on the peripheral circulation

The activity on the peripheral circulation was studied on an anaesthetized dog (sodium pentobarbital 30 mg/kg/i.v.). The femoral artery flow was measured by means of an electromagnetic or ultrasonic perivascular Doppler effect probe.

The systemic arterial pressure was measured at the femoral artery with a pressure sensor (SANBORN-267 BC).

The results obtained by injecting the compounds of formula I and the following reference compounds: papaverine, naphtidrofuryl and cinnarizine are given in Table IX below (intravenous injection with slow perfusion).

TABLE IX

| Compound tested Code No. | Dose mg/kg/i.v. | Femoral artery flow in % | Femoral artery flow in time (min) | Average arterial pressure in % | Average arterial pressure in time (min) |
|---|---|---|---|---|---|
| 760 392 | 10 | +56 | 45 | −28 | 38 |
| 760 501 | 5 | +61 | 23 | −22 | 35 |
| 760 502 | 5 | +190 | 35 | −22 | 15 |
| 760 505 | 5 | +24 | 15 | −21 | 23 |
| 760 521 | 5 | +34 | 15 | −19 | 30 |
| 760 503 | 5 | +87 | 15 | −6 | 15 |
| 760 504 | 5 | +49 | 15 | −23 | 10 |
| Papaverine | 2 | +100 | 1 | — | — |
| Naphtidrofuryl | 2,5 | +100 | 5 | −50 | 2 |
| Cinnarizine | 5 | +100 | 30 | −20 | 15 |

It is evident from the preceeding results that the difference between therapeutic doses and toxic doses is sufficiently great to allow the compounds of formula I to be used in the treatment of disturbances in the cardiovascular systems, particularly as antiangorous agents and as agents active on the cerebral and peripheral circulation.

They will be administered intravenously in the form of injectable ampoules containing 60 to 120 mg of active constituent or orally in the form of tablets, pills or capsules containing 20 to 200 mg of active constituent (1 to 3 per day).

What is claimed is:

1. A compound having the formula

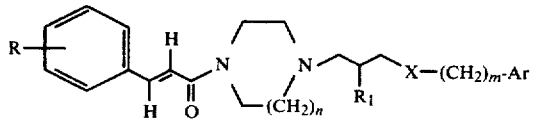

in which

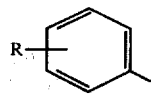

is selected from the group consisting of

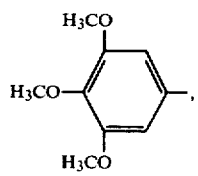

4-fluorophenyl, 3,5-dimethoxyphenyl, 3,4-methylenedioxyphenyl,

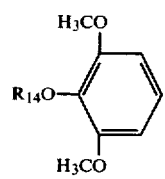

in which $R_{14}$ is hydrogen or linear or branched alkyl having 2 or 3 carbon atoms, and

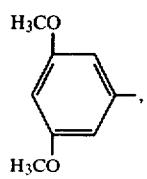

and in which
I. when

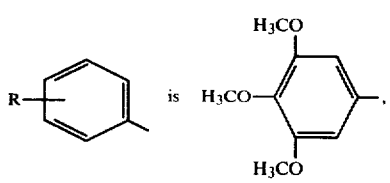

the parameters (n, $R_1$, X, m) are selected from the group consisting of (1, OH, oxygen, zero), (2, OH, Oxygen, zero), (1, H, oxygen, zero), (1, OH, S, zero),

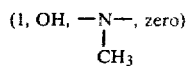

and (1, OH, oxygen, 1), and in which

A. when (n, $R_1$, X, m) is (1, OH, oxygen, zero), Ar is selected from the group consisting of

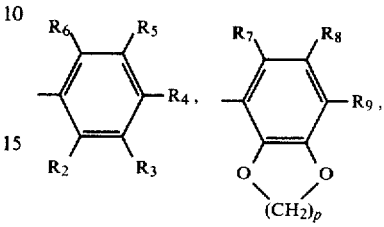

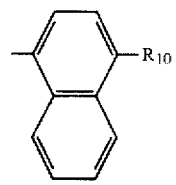

in which $R_{10}$ is acetyl, acetamido or N-methylcarbamoylamino,

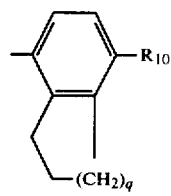

in which q is 1 or 2 and $R_{10}$ has the same meaning as defined above,

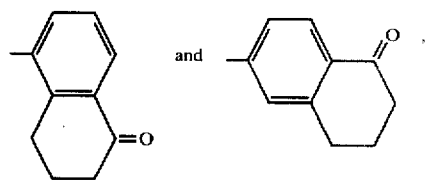

and in which
1. when Ar is

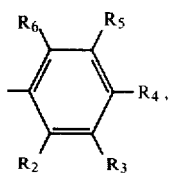

$R_2$, $R_3$, $R_4$, $R_5$ and $R_6$ are selected from the group consisting of a. $R_3=R_4=R_5=R_6=H$, and $R_2$ is chloro, fluoro, acetamido, acetyl, cyano, methoxy, methyl, allyl or allyloxy, b. $R_2=R_4=R_5=R_6=H$, and $R_3$ is acetamido, methyl, acetyl, cyano, methoxy or chloro, c. $R_2=R_3=R_5=R_6=H$, and $R_4$ is chloro, cyano, nitro, methylthio, benzoyl, ethyl carboxylate, methyl, linear or branched alkyl having from 3 to 5 carbon atoms, cyclohexyl, alkanoyl in which alkyl has from 1 to 3 carbon atoms, alkanoylamino in which alkyl has from 1 to 3 carbon atoms, carboxamido, N-methylcarboxamido, cyanomethyl, carboxamidomethyl or N-methylcarbamoylamino, d. $R_3=R_5=R_6=H$, $R_2$ is fluoro and $R_4$ is acetyl, e. $R_3=R_5=R_6=H$, $R_2$ is chloro and $R_4$ is nitro, acetyl, or N-methylcarbamoylamino, f. $R_3=R_5=R_6=H$, $R_2$ is methyl and $R_4$ is chloro, acetyl, acetamido or N-methylcarbamoylamino, g. $R_3=R_5=R_6=H$, $R_2$ is methoxy and $R_4$ is acetyl, propionyl, formyl, cyano, acetamido, or N-methylcarboxamido, h. $R_4=R_5=R_6=H$, and $R_2$ and $R_3$ are methoxy, i. $R_3=R_4=R_5=H$, and $R_2$ and $R_6$ are methoxy, j. $R_2=R_4=R_6=H$, and $R_3$ and $R_5$ are methoxy, k. $R_2=R_5=R_6=H$, and $R_3$ and $R_4$ together are methylenedioxy, l. $R_2=R_5=R_6=H$, $R_3$ is methyl and $R_4$ is nitro, acetamido or N-methylcarbamoylamino, m. $R_2=R_6=H$, and $R_3$, $R_4$ and $R_5$ are methoxy, n. $R_2=R_6=H$, $R_3$ and $R_5$ are methyl, and $R_4$ is chloro, o. $R_5=R_6=H$, $R_2$ and $R_3$ are methoxy and $R_4$ is N-methylcarbamoylamino, p. $R_3=R_5=H$, $R_2$ and $R_6$ are chloro, and $R_4$ is acetyl or N-methylcarbamoylamino, q. $R_3=R_5=H$, $R_2$ and $R_6$ are methoxy and $R_4$ is acetyl, ethyl carboxylate or N-methylcarbamoylamino, and r. $R_6=H$, $R_3$, $R_4$ and $R_5$ are methoxy and $R_2$ is acetyl, and in which 2. when Ar is

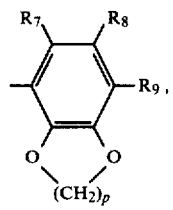

p, $R_7$, $R_8$ and $R_9$ are selected from the group consisting of a. p=2, $R_7=R_8=H$, and $R_9$ is hydrogen, hydroxy, acetoxy, methoxy, methyl, ethyl, cyano, acetyl, n-butyroyl, alkoxy carbonyl in which the alkoxy is linear or branched and has from 2 to 5 carbon atoms, cyclohexyloxycarbonyl, carboxamido, N-methylcarboxamido, N-cyclohexylcarboxamido, N-phenylcarboxamido, alkanoylamino in which the alkyl is linear or branched and has from 1 to 5 carbon atoms, cyclohexylcarbonylamino, benzoylamino, N-alkylcarbamoylamino in which the alkyl is linear or branched alkyl and has from 1 to 5 carbon atoms, N-cyclohexylcarbamoylamino, N-phenylcarbamoylamino, N-(paramethoxy-phenyl)-carbamoylamino, N-N-dimethylcarbamoylamino, morpholinocarbonylamino, N-N′-dimethylcarbamoylamino, ethoxycarbonylamino, hydroxymethyl, cyanomethyl, ethyl acetate, carboxamidomethyl or N-methylcarboxamidomethyl, b. p=2, $R_7=R_9=H$, and $R_8$ is acetyl, c. p=2, $R_8=R_9=H$, and $R_7$ is acetamido, d. p=1 or 3, $R_7=R_8=H$, and $R_9$ is hydrogen, acetyl, acetamido or N-methylcarbamoylamino, B. when (n, $R_1$, X, m) is (2, OH, oxygen, zero), Ar is selected from the group consisting of phenyl,

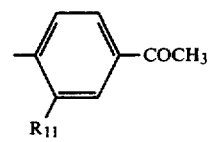

in which $R_{11}$ is hydrogen or methoxy, and

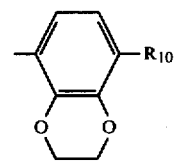

in which $R_{10}$ has the same meaning as previously, c. when (n, $R_1$, X, m) is (1, H, oxygen, zero), Ar is

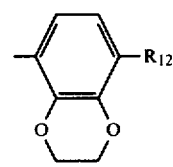

in which $R_{12}$ is acetyl, acetamido, N-methylcarboxamido or N-methylcarbamoylamino, D. when (n, $R_1$, X, m) is (1, OH, S, O), Ar is phenyl, metamethoxyphenyl, paratolyl,

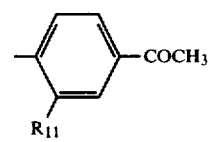

in which $R_{11}$ is hydrogen or methoxy, or

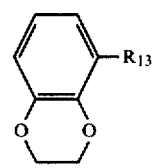

in which $R_{13}$ is hydrogen or acetyl,

E. when (n, $R_1$, X, m) is

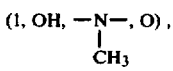

Ar is phenyl, and
F. when (n, R₁, X, m) is (1, OH, oxygen, 1), Ar is phenyl,

II. when

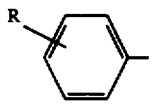

is 4-fluorophenyl, 3,5-dimethoxyphenyl, 3,4-methylenedioxyphenyl, or

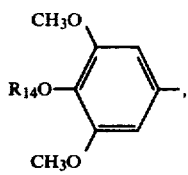

the parameters (n, R₁, X, m) are (1, OH, oxygen, zero) and Ar is

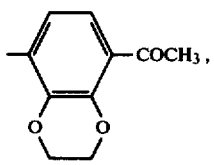

III. when

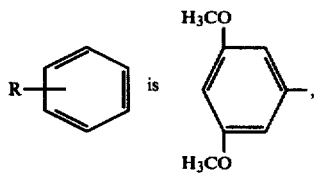

the parameters (n, R₁, X, m) are (1, OH, oxygen, zero) and Ar is

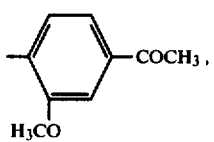

and the pharmacologically acceptable salts thereof.

2. A compound according to claim 1, having the formula

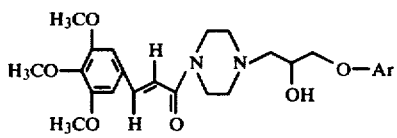

wherein Ar is selected from the group consisting of

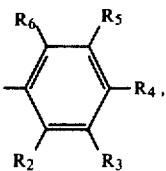

in which the combination of R₂, R₃, R₄, R₅ and R₆ is selected from the group consisting of (1-a) R₃, R₄, R₅ and R₆ are hydrogen, and R₂ is chloro, fluoro, acetamido, acetyl, cyano, methoxy, methyl, allyl or allyloxy, (1-b) R₂, R₄, R₅ and R₆ are hydrogen, and R₃ is acetamido, methyl, acetyl, cyano, methoxy or chloro, (1-c) R₂, R₃, R₅ and R₆ are hydrogen, and R₄ is chloro, cyano, nitro, methylthio, benzoyl, ethyl carboxylate, methyl, linear or branched alkyl having 3 to 5 carbon atoms, cyclohexyl, alkanoyl in which the alkyl group contains 1 to 3 carbon atoms, alkanoylamino in which the alkyl group contains 1 to 3 carbons, carboxamido, N-methylcarboxamido, cyanomethyl, carboxamidomethyl or N-methylcarbamoylamino, (1-d) R₃, R₅ and R₆ are hydrogen, R₂ is fluoro and R₄ is acetyl, (1-e) R₃, R₅ and R₆ are hydrogen, R₂ is chloro and R₄ is nitro, acetyl or N-methylcarbamoylamino, (1-f) R₃, R₅ and R₆ are hydrogen, R₂ is methyl and R₄ is chloro, acetyl, acetamido or N-methylcarbamoylamino, (1-g) R₃, R₅ and R₆ are hydrogen, R₂ is methoxy and R₄ is acetyl, propionyl, formyl, cyano, acetamido or N-methylcarboxamido, (1-h) R₄, R₅ and R₆ are hydrogen and R₂ and R₃ are methoxy, (1-i) R₃, R₄ and R₅ are hydrogen and R₂ and R₆ are methoxy, (1-j) R₂, R₄ and R₆ are hydrogen and R₃ and R₅ are methoxy, (1-k) R₂, R₅ and R₆ are hydrogen and R₃ and R₄ together are methylenedioxy, (1-l) R₂, R₅ and R₆ are hydrogen, R₃ is methyl and R₄ is nitro, acetamido or N-methylcarbamoylamino, (1-m) R₂ and R₆ are hydrogen and R₃, R₄ and R₅ are methoxy, (1-n) R₂ and R₆ are hydrogen, R₃ and R₅ are methyl and R₄ is chloro, (1-o) R₅ and R₆ are hydrogen, R₂ and R₃ are methoxy and R₄ is N-methylcarbamoylamino, (1-p) R₃ and R₅ are hydrogen, R₂ and R₆ are chloro and R₄ is acetyl or N-methylcarbamoylamino, (1-q) R₃ and R₅ are hydrogen, R₂ and R₆ are methoxy and R₄ is acetyl, ethyl carboxylate or N-methylcarbamoylamino, (1-r) R₅ is hydrogen, R₃, R₄ and R₆ are methoxy and R₂ is acetyl,

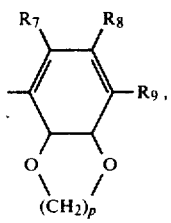

in which the combination of p, $R_7$, $R_8$ and $R_9$ is selected from the group consisting of (2-a) p is 2, $R_7$ and $R_8$ are hydrogen and $R_9$ is hydrogen, hydroxy, acetoxy, methoxy, methyl, ethyl, cyano, acetyl, n-butyroyl, alkoxycarbonyl wherein the alkoxy is linear or branched and contains 2 to 5 carbon atoms, cyclohexyloxycarbonyl, carboxamido, N-methylcarboxamido, N-cyclohexylcarboxamido, N-phenylcarboxamido, alkanoylamino in which the alkyl is linear or branched and has from 1 to 5 carbon atoms, cyclohexylcarbonylamino, benzoylamino, N-alkylcarbamoylamino wherein the alkyl is linear or branched and has from 1 to 5 carbon atoms, N-cyclohexylcarbamoylamino, N-phenylcarbamoylamino, N-(paramethoxyphenyl)-carbamoylamino, N,N-dimethylcarbamoylamino, morpholinocarbonylamino, N,N'-dimethylcarbamoylamino, ethoxycarbonylamino, hydroxymethyl, cyanomethyl, ethylacetate, carboxamidomethyl or N-methylcarboxamidomethyl, (2-b) p is 2, $R_7$ and $R_9$ are hydrogen and $R_8$ is acetyl, (2-c) p is 2, $R_8$ and $R_9$ are hydrogen and $R_7$ is acetamido, and (2-d) p is 1 or 3, $R_7$ and $R_8$ are hydrogen and $R_9$ is hydrogen, acetyl, acetamido or N-methylcarbamoylamino, (3)

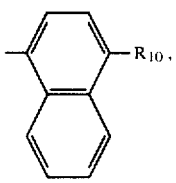

in which $R_{10}$ is acetyl, acetamido or N-methylcarbamoylamino, (4)

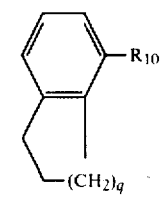

in which q is 1 or 2 and $R_{10}$ is the same as defined above, (5)

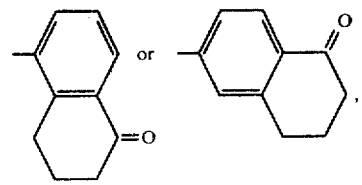

and the pharmacologically acceptable salts thereof.

3. A compound according to claim 2 in which Ar is (1).

4. A compound according to claim 3 in which the combination of $R_2$, $R_3$, $R_4$, $R_5$ and $R_6$ is (1-a).

5. A compound according to claim 3 in which the combination of $R_2$, $R_3$, $R_4$, $R_5$ and $R_6$ is (1-b).

6. A compound according to claim 3 in which the combination of $R_2$, $R_3$, $R_4$, $R_5$ and $R_6$ is (1-c).

7. A compound according to claim 3 in which the combination of $R_2$, $R_3$, $R_4$, $R_5$ and $R_6$ is (1-d).

8. A compound according to claim 3 in which the combination of $R_2$, $R_3$, $R_4$, $R_5$ and $R_6$ is (1-e).

9. A compound according to claim 3 in which the combination of $R_2$, $R_3$, $R_4$, $R_5$ and $R_6$ is (1-f).

10. A compound according to claim 3 in which the combination of $R_2$, $R_3$, $R_4$, $R_5$ and $R_6$ is (1-g).

11. A compound according to claim 3 in which the combination of $R_2$, $R_3$, $R_4$, $R_5$ and $R_6$ is (1-h).

12. A compound according to claim 3 in which the combination of $R_2$, $R_3$, $R_4$, $R_5$ and $R_6$ is (1-i).

13. A compound according to claim 3 in which the combination of $R_2$, $R_3$, $R_4$, $R_5$ and $R_6$ is (1-j).

14. A compound according to claim 3 in which the combination of $R_2$, $R_3$, $R_4$, $R_5$ and $R_6$ is (1-k).

15. A compound according to claim 3 in which the combination of $R_2$, $R_3$, $R_4$, $R_5$ and $R_6$ is (1-l).

16. A compound according to claim 3 in which the combination of $R_2$, $R_3$, $R_4$, $R_5$ and $R_6$ is (1-m).

17. A compound according to claim 3 in which the combination of $R_2$, $R_3$, $R_4$, $R_5$ and $R_6$ is (1-n).

18. A compound according to claim 3 in which the combination of $R_2$, $R_3$, $R_4$, $R_5$ and $R_6$ is (1-o).

19. A compound according to claim 3 in which the combination of $R_2$, $R_3$, $R_4$, $R_5$ and $R_6$ is (1-p).

20. A compound according to claim 3 in which the combination of $R_2$, $R_3$, $R_4$, $R_5$ and $R_6$ is (1-q).

21. A compound according to claim 3 in which the combination of $R_2$, $R_3$, $R_4$, $R_5$ and $R_6$ is (1-r).

22. A compound according to claim 2 in which Ar is (2).

23. A compound according to claim 22 in which the combination of p, $R_7$, $R_8$ and $R_9$ is (2-a).

24. A compound according to claim 22 in which the combination of p, $R_7$, $R_8$ and $R_9$ is (2-b).

25. A compound according to claim 22 in which the combination of p, $R_7$, $R_8$ and $R_9$ is (2-c).

26. A compound according to claim 22 in which the combination of p, $R_7$, $R_8$ and $R_9$ is (2-d).

27. A compound according to claim 2 in which Ar is (3).

28. A compound according to claim 2 in which Ar is (4).

29. A compound according to claim 2 in which Ar is (5).

30. A compound according to claim 1, having the formula

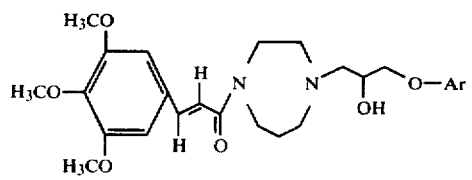

wherein Ar is selected from the group consisting of phenyl,

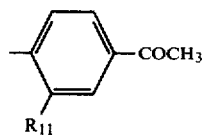

in which $R_{11}$ is hydrogen or methoxy and

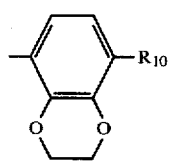

in which $R_{10}$ is acetyl, acetamido or N-methylcarbamoylamino, and the pharmacologically acceptable salts thereof.

31. A compound according to claim 1, having the formula

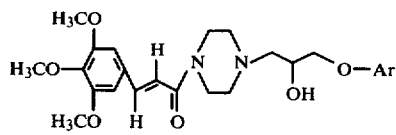

wherein Ar is

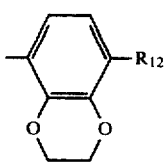

in which $R_{12}$ is acetyl, acetamido, N-methylcarboxamido or N-methylcarbamoylamino, and the pharmacologically acceptable salts thereof.

32. A compound according to claim 1, having the formula

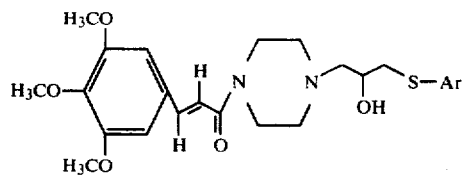

wherein Ar is selected from the group consisting of phenyl, metamethoxyphenyl, para-tolyl,

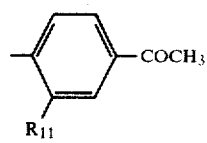

in which $R_{11}$ is hydrogen or methoxy, and

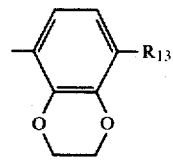

in which $R_{13}$ is hydrogen or acetyl, and the pharmacologically acceptable salts thereof.

33. A compound according to claim 1, having the formula

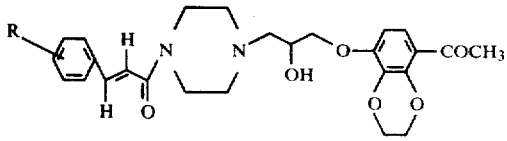

and the pharmacologically scceptable salts thereof.

34. A compound according to claim 1, having the formula

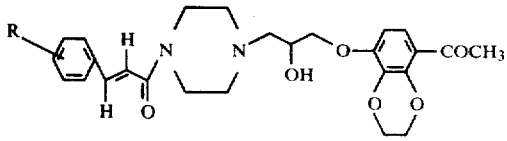

and the pharmacologically acceptable salts thereof.

35. A compound according to claim 1, having the formula

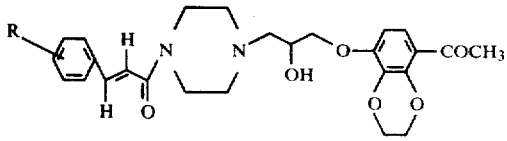

wherein

is selected from the group consisting of 4-fluorophenyl, 3,5-dimethoxyphenyl, 3,4-methylenedioxy or

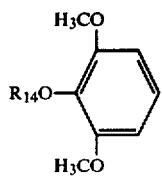

in which $R_{14}$ is hydrogen or linear or branched alkyl having 2 or 3 carbon atoms, and the pharmacologically acceptable salts thereof.

36. A compound according to claim 1, having the formula

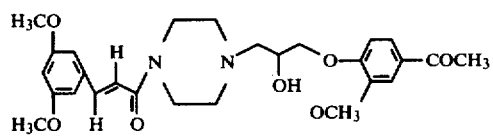

and the pharmacologically acceptable salts thereof.

37. A process for preparing a compound having the formula

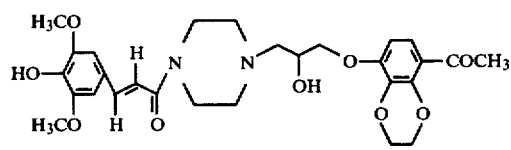

which comprises hydrolyzing a compound having the formula

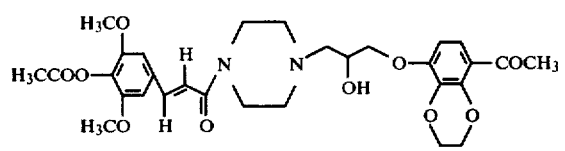

with an alcoholic solution of sodium bicarbonate.

38. A process for preparing a compound having the formula

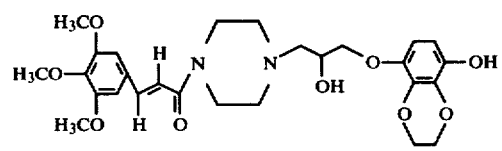

which comprises hydrolyzing a compound having the formula

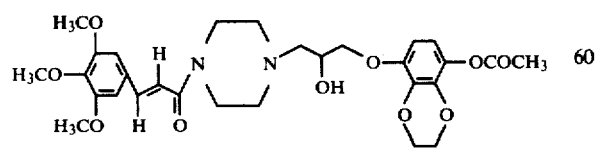

with an alcoholic solution of sodium bicarbonate.

39. A process for preparing a compound having the formula

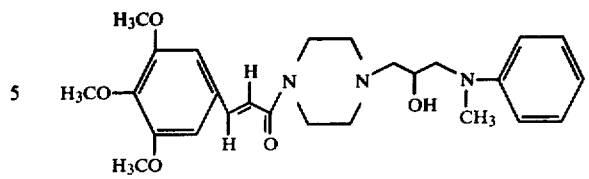

which comprises condensing a compound of the formula

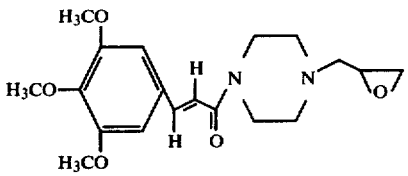

with N-methylaniline in an alcohol medium.

40. A process for preparing a compound having the formula

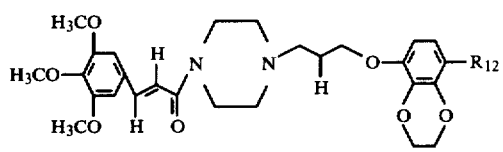

wherein $R_{12}$ is acetyl, acetamido, N-methylcarboxamido or N-methylcarbamoylamino which comprises condensing a compound of the formula

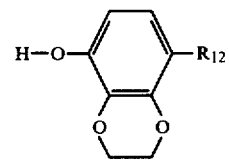

with 1-bromo-3-chloropropane to obtain a compound of the formula

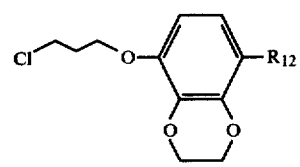

and then reacting the latter compound with a compound of the formula

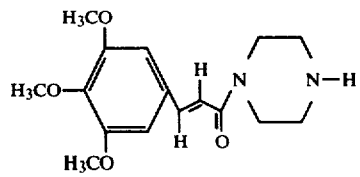

in solution in acetonitrile, in the presence of potassium carbonate.

* * * * *